United States Patent
Peled et al.

(10) Patent No.: US 11,129,824 B2
(45) Date of Patent: Sep. 28, 2021

(54) SMALL MOLECULES FOR INHIBITING CHEMOKINE ACTIVITY AND/OR CANCER CELLS GROWTH

(71) Applicant: Biokine Therapeutics Ltd., Nes Ziona (IL)

(72) Inventors: Amnon Peled, Tel-Aviv (IL); Michal Abraham, Mevasseret Zion (IL); Orly Eizenberg, Rechovot (IL)

(73) Assignee: Biokine Therapeutics Ltd., Nes Ziona (IL)

( * ) Notice: Subject to any disclaimer, the term of this patent is extended or adjusted under 35 U.S.C. 154(b) by 548 days.

(21) Appl. No.: 16/063,279

(22) PCT Filed: Dec. 15, 2016

(86) PCT No.: PCT/IL2016/051347
§ 371 (c)(1),
(2) Date: Jun. 17, 2018

(87) PCT Pub. No.: WO2017/103932
PCT Pub. Date: Jun. 22, 2017

(65) Prior Publication Data
US 2019/0336492 A1  Nov. 7, 2019

Related U.S. Application Data

(60) Provisional application No. 62/268,586, filed on Dec. 17, 2015.

(51) Int. Cl.
| | | |
|---|---|---|
| *C07D 215/30* | (2006.01) | |
| *A61K 31/4704* | (2006.01) | |
| *A61P 35/02* | (2006.01) | |
| *A61K 45/06* | (2006.01) | |

(52) U.S. Cl.
CPC .......... *A61K 31/4704* (2013.01); *A61P 35/02* (2018.01); *A61K 45/06* (2013.01)

(58) Field of Classification Search
CPC . A61K 31/4704; C07D 215/24; C07D 215/22
See application file for complete search history.

(56) References Cited

U.S. PATENT DOCUMENTS

| | | | |
|---|---|---|---|
| 5,116,964 A | 5/1992 | Capon et al. | |
| 5,541,196 A * | 7/1996 | Fournet | A61P 33/10 514/311 |
| 6,002,008 A | 12/1999 | Wissner et al. | |
| 9,493,557 B2 | 11/2016 | Abraham et al. | |
| 10,646,465 B2 | 5/2020 | Peled et al. | |
| 2008/0299130 A1 | 12/2008 | Ambati | |
| 2011/0027643 A1 | 2/2011 | Li et al. | |
| 2012/0087921 A1 | 4/2012 | Abraham et al. | |
| 2013/0345212 A1* | 12/2013 | Daugan | A61P 9/00 514/230.5 |
| 2014/0154249 A1 | 6/2014 | Abraham et al. | |
| 2017/0015708 A1 | 1/2017 | Abraham et al. | |
| 2017/0226157 A1 | 8/2017 | Peled | |
| 2019/0240188 A1 | 8/2019 | Peled et al. | |
| 2020/0268709 A1 | 8/2020 | Peled et al. | |
| 2020/0369617 A1 | 11/2020 | Peled et al. | |

FOREIGN PATENT DOCUMENTS

| | | |
|---|---|---|
| EA | 003933 | 10/2003 |
| JP | 2003-512011 | 4/2003 |

(Continued)

OTHER PUBLICATIONS

Notice of Reason for Rejection dated Dec. 8, 2020 From the Japan Patent Office Re. Application No. 2018-531613. and Its Translation Into English. (5 Pages).

(Continued)

*Primary Examiner* — Shobha Kantamneni

(57) ABSTRACT

Compounds capable of, or usable in, inducing death of cancer cells and/or modulating a biological activity of a chemokine e.g., cell migration, and/or treating diseases and disorders associated with a biological activity of a chemokine and/or cell migration, and/or inhibiting a kinase and/or in treating a disease or disorder associated with an activity of a kinase, such as cancer and inflammatory diseases and disorders, are provided herein. The compounds are collectively represented by Formulae Ia or Ib:

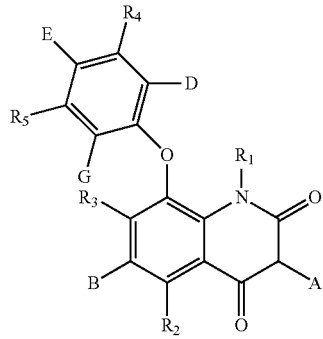

Formula Ia

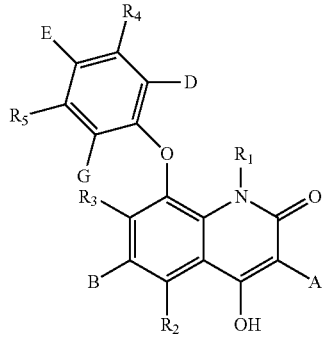

Formula Ib wherein A, B D, E, G and $R_1$-$R_5$ are as defined in the specification.

21 Claims, 46 Drawing Sheets
(44 of 46 Drawing Sheet(s) Filed in Color)

(56) References Cited

FOREIGN PATENT DOCUMENTS

| | | |
|---|---|---|
| JP | 2003-530318 | 10/2003 |
| WO | WO 92/20642 | 11/1992 |
| WO | WO 95/15758 | 6/1995 |
| WO | WO 95/21613 | 8/1995 |
| WO | WO 97/30035 | 8/1997 |
| WO | WO 99/61428 | 12/1999 |
| WO | WO 00/10981 | 3/2000 |
| WO | WO 00/24782 | 5/2000 |
| WO | WO 00/56720 | 9/2000 |
| WO | WO 01/21598 | 3/2001 |
| WO | WO 02/42248 | 5/2002 |
| WO | WO 03/072599 | 9/2003 |
| WO | WO 2007/052173 | 5/2007 |
| WO | WO 2007/094005 | 8/2007 |
| WO | WO 2008/115870 | 9/2008 |
| WO | WO 2010/143168 | 12/2010 |
| WO | WO 2010/146584 | 12/2010 |
| WO | WO 2016/092544 | 6/2016 |
| WO | WO 2017/103931 | 6/2017 |
| WO | WO 2017/103932 | 6/2017 |
| WO | WO 2020/230144 | 11/2020 |
| WO | WO 2020/230144 A8 | 1/2021 |

OTHER PUBLICATIONS

Advisory Action Before the Filing of an Appeal Brief dated Sep. 23, 2013 From the US Patent and Trademark Office Re. U.S. Appl. No. 13/378,063.
Communication Pursuant to Article 94(3) EPC dated May 7, 2014 From the European Patent Office Re. Application No. 10735337.7.
Communication Pursuant to Article 94(3) EPC dated Dec. 14, 2012 From the European Patent Office Re. Application No. 10735337.7.
Communication Relating to the Results of the Partial International Search dated Feb. 26, 2017 From the International Searching Authority Re. Application No. PCT/IL2016/051346. (20 Pages).
Examination Report dated Feb. 18, 2014 From the Instituto Mexicano de la Propiedad Industrial Re. Application No. MX/a/2011/013457 and Its Translation Into English.
International Preliminary Report on Patentability dated Jun. 22, 2017 From the International Bureau of WIPO Re. Application No. PCT/IL2015/051190. (8 Pages).
International Preliminary Report on Patentability dated Dec. 29, 2011 From the International Bureau of WIPO Re. Application No. PCT/IL2010/000473.
International Search Report and the Written Opinion dated Mar. 19, 2017 From the International Searching Authority Re. Application No. PCT/IL2016/051347. (10 Pages).
International Search Report and the Written Opinion dated Oct. 22, 2010 From the International Searching Authority Re. Application No. PCT/IL2010/000473.
International Search Report and the Written Opinion dated Mar. 28, 2016 From the International Searching Authority Re. Application No. PCT/1L2015/051190.
International Search Report and the Written Opinion dated Mar. 29, 2017 From the International Searching Authority Re. Application No. PCT/IL2016/051346. (33 Pages).
Notice of Preliminary Rejection dated Feb. 8, 2017 From the Korean Intellectual Property Office Re. Application No. 2012-7000920. (6 Pages).
Notice of Reason for Rejection dated Oct. 17, 2014 From the Japanese Patent Office Re. Application No. 2012-515627 and Its Translation Into English.
Notification of Office Action dated Oct. 31, 2013 From the State Intellectual Property Office of the People's Republic of China Re. Application No. 201080036127.9 and Its Translation Into English.
Office Action dated Jul. 8, 2013 From the Israel Patent Office Re. Application No. 216978 and Its Translation Into English.
Office Action dated Mar. 26, 2015 From the Israel Patent Office Re. Application No. 216978 and Its Translation Into English.
Official Action dated Jul. 1, 2013 From the US Patent and Trademark Office Re. U.S. Appl. No. 13/378,063.
Official Action dated Jul. 7, 2015 From the US Patent and Trademark Office Re. U.S. Appl. No. 14/178,301.
Official Action dated Jan. 8, 2013 From the US Patent and Trademark Office Re. U.S. Appl. No. 13/378,063.
Official Action dated Feb. 9, 2016 From the US Patent and Trademark Office Re. U.S. Appl. No. 14/178,301.
Official Action dated Aug. 21, 2017 From the US Patent and Trademark Office Re. U.S. Appl. No. 15/326,512. (42 pages).
Official Action dated Aug. 28, 2017 From the US Patent and Trademark Office Re. U.S. Appl. No. 15/285,492. (31 pages).
Requisition by the Examiner dated May 25, 2016 From the Canadian Intellectual Property Office Re. Application No. 2,765,188.
Requisition by the Examiner dated Jun. 27, 2017 From the Canadian Intellectual Property Office Re. Application No. 2,765,188. (8 Pages).
Restriction Official Action dated Mar. 10, 2015 From the US Patent and Trademark Office Re. U.S. Appl. 14/178,301.
Restriction Official Action dated Aug. 23, 2012 From the US Patent and Trademark Office Re. U.S. Appl. No. 13/378,063.
Translation of Notice of Preliminary Rejection dated Feb. 8, 2017 From the Korean Intellectual Property Office Re. Application No. 2012-7000920. (4 Pages).
Translation of Office Action dated May 2, 2013 From the State Intellectual Property Office of the People's Republic of China Re. Application No. 201080036127.9.
Translation of Search Report dated May 2, 2013 From the State Intellectual Property Office of the People's Republic of China Re. Application No. 201080036127.9.
Baggiolini et al. "Cc Chemokines in Allergic Inflammation", Immunology Today, 15(3): 127-133, 1994.
Bork "Powers and Pitfalls in Sequence Analysis: The 70% Hurdle", Genome Research, 10: 398-400, 2000.
Cocchi et al. "Identification of RANTES, MIP-1[Alpha], and MIP-1[Beta] as the Major HIV-Suppressive Factors Produced by CD8+ T Cells", Science, 270(5243): 1811-1815, Dec. 15, 1995.
Debnath et al. "Small Molecule Inhibitors of CXCR4", Theranostics, 3(1): 47-75, Jan. 15, 2013. Abstract, Figs.
Doercks et al. "Protein Annotation: Detective Work for Function Prediction", Trends in Genetics, TiG, 14(6): 248-250, Jun. 1998.
Duan et al. "Inhaled P38[Alpha] Mitogen-Activated Protein Kinase Antisense Oligonucleotide Attenuates Asthma in Mice", American Journal of Respiratory and Critical Care Medicine, 171: 571-578, Originally Published Nov. 19, 2004.
Elix et al. "Annelated Furans. XvIII. The Photocyclization of 2-Methoxyphenyl Phenyl Ethers", Australian Journal of Chemistry, 28(7): 1559-1582, Dec. 31, 1975. p. 1562, Compounds 11, 12, 14.
Epifano et al. "Auraptene and Its Effects on the Re-Emergence of Colon Cancer Stem Cells", Phytotherapy Research, 27(5): 784-786, Epub Jul. 4, 2012.
Escott et al. "Effect of the P38 Kinase Inhibitor, SB 203580, on Allergic Airway Inflammation in the Rat", British Journal of Pharmacology, 131(2): 173-176, Sep. 2000.
Haddad et al. "Role of P38 MAP Kinase in LPS-Induced Airway Inflammation in the Rat", British Journal of Pharmacology, 132(8): 1715-1724, Apr. 2001.
Hu et al. "Design, Synthesis, and Biological Evaluation of Novel Quinazoline Derivatives as Anti-Inflammatory Agents Against Lipopolysaccharide-Induced Acute Lung Injury in Rats", Chemical Biology & Drug Design, 85(6): 672-684, Published Online Nov. 6, 2014. Schemes 1, p. 7, Compounds 6a, 6b, 6c, 6d, 6g, 6i, Schemes 1, p .7, 6o, 6p, 6q, Scheme 2, p. 7.
Huang et al. "Anticancer Activities of Polyynes From the Root Bark of *Oplopanax horridus* and Their Acetylated Derivatives", Molecules, 19: 6142-6162, May 14, 2014.
Joulain et al. "Lichen Extracts as Raw Materials in Perfumery. Part 2: Treemoss", Flavour and Fragrance Journal, 24(3): 105-116, Mar. 11, 2009. p. 5, Fig.4, Compounds 32-33.
Kasuga et al. "Sensitization of Human Glioblastomas to Tumor Necrosis Factor-Related Apoptosis-Inducing Ligand (TRAIL) by NF-KB Inhibitors", Cancer Science, 95(10): 840-844, Oct. 2004.

(56) References Cited

OTHER PUBLICATIONS

Kim et al. "Isolation and Characterization of Antitumor Agents From Dictamnus Albus", Saengyak Hakhoe Chi, 28(4): 209-214, Dec. 28, 1997. Abstract. Abstract.
Kioi et al. "Inhibition of Vasculogenesis, But Not Angiogenesis, Prevents the Recurrence of Glioblastoma After Irradiation in Mice", The Journal of Clinical Investigation, 120(3): 694-705, Mar. 2010.
Kryczek et al. "Stroma-Derived Factor (SDF-1/CXCL12) and Human Tumor Pathogenesis", American Journal of Physiology, Cell Physiology, 292(3): C987-C995, First Published Aug. 30, 2006.
Lee et al. "Ocular Neovascularization: An Epidemiologic Review", Survey of Ophthalmology, 43(3): 245-269, Nov.-Dec. 1998.
Lo et al. "High Level Expression and Secretion of Fc-X Fusion Proteins in Mammalian Cells", Protein Engineering, 11(6): 495-500, Jun. 1998.
Luhmann et al. The Relevance of Chemokine Signalling in Modulating Inherited and Age-Related Retinal Degenerations:, Retinal Degenerative Diseases, Chap.54: 427-433, Mar. 25, 2014.
Ma et al. "Impaired B-Lymphopoiesis, Myelopoiesis, and Derailed Cerebellar Neuron Migration in CXCR4- and SDF-1-Deficient Mice", Proc. Natl. Acad. Sci. USA, 95(16): 9448-9453, Aug. 1998.
Mathebula "A Review of Ocular Genetics and Inherited Eye Diseases", African Vision and Eye Health, 71(4): 179-189. 2012.
Niu et al. "New Polyphenols From a Deep sea *Spiromastix* Sp. Fungus, and Their Antibacterial Activities", Marine Drugs, 13(4): 2526-2540, Apr. 22, 2015. Fig.1, Compound 9, p. 2527.
Nomura et al. "Effects of Oakmoss and Its Components on Biofilm Formation of Legionella Pneumophila", Biological and Pharmaceutical Bulletin, 36(5): 833-837, May 2013. Compounds 14, 17, 20, p. 834.
Nomura et al. "The Antibacterial Activity of Compounds Isolated From Oakmoss Against *Legionella pneumophila* and Other *Legionella* Spp.", Biological & Pharmaceutical Bulletin, 35(9): 1560-1567, Jun. 2012. p. 1562-1563, Fig.1, Table 1, Compounds 14, 17, 20.
Reeck et al. "'Homology' in Proteins and Nucleic Acids: A Terminology Muddle and a Way Out of It", Cell, 50(5): 667, Aug. 28, 1987.
Rutar et al. "Small Interfering RNA-Mediated Suppression of Ccl2 in Mueller Cells Attenuates Microglial Recruitment and Photoreceptor Death Following Retinal Degeneration", Journal of Neuroinflammation, 9(221): 1-15, Published Online Sep. 19, 2012.
Skolnick et al. "From Genes to Protein Structure and Function: Novel Applications of Computational Approaches in the Genomic Era", Trends in Biotechnology. TiBTech, 18(1): 34-39, Jan. 2000.
Smith et al. "CXCR4 Regulates Growth of Both Primary and Metastatic Breast Cancer", Cancer Research, 64: 8604-8612, Dec. 1, 2004.
Stedman "Allograft Rejection", Stedman's Online, Lippincott Williams and Wilkins, Jun. 23, 2015.
Stedman "Malignant", Stedman's Online, Lippincott Williams and Wilkins, Jun. 23, 2015.
Stedman "Myasthenia Gravis", Stedman's Online, Lippincott Williams and Wilkins, Jun. 23, 2015.
Stedman "Systemic Lupus Erythematosus" Stedman's Online, Lippincott Williams and Wilkins, Jun. 23, 2015.
Strieter et al. "The Functional Role of the ELR Motif in CXC Chemokine-Mediated Angiogenesis", The Journal of Biological Chemistry, 270(45): 27348-27357, Nov. 10, 1995.
Sulaiman et al. "In Vitro and In Silico Studies of Lunacridine From Lunasia Amara Blanco as Anticancer", Journal of Life Sciences, 5(8): 639-645, Published Online Aug. 30, 2011. Abstract.
Tannock et al. "The Basic Science of Oncology", Third Edition, New York: McGraw-Hill; p. 357-358, 1998.
Tokuriki et al. "Stability Effects of Mutations and Protein Evolvability", Current Opinion in Structural Biology, 19: 596-604, 2009.
Toyooka et al. "CD28 Co-Stimulatory Signals Induce IL-2 Receptor Expression on antigen-Stimulated Virgin T Cells by an IL-2-Independent Mechanism", International Immunology, 8(2): 159-169, Feb. 1996.
Underwood et al. "SB 239063, A P38 MAPK Inhibitor, Reduces Neutrophilia, Inflammatory Cytokines, MMP-9, and Fibrosis in Lung", American Journal of Physiology, Lung Cellular and Molecular Physiology, 279(5): L895-L902, Nov. 2000.
Underwood et al. "SB 239063, A Potent P38 MAP Kinase Inhibitor, Reduces Inflammatory Cytokine Production, Airways Eosinophil Infiltration, and Persistence", The Journal of Pharmacology and Experimental Therapeutics, 293(1): 281-288, Apr. 2000.
Vaddi et al. "Regulation of Monocyte Integrin Expression by Beta-Family Chemokines", The Journal of Immunology, 153(10): 4721-4732, Nov. 15, 1994.
Wallace et al. "The Role of Chemokines and Their Receptors in Ocular Disease", Progress in Retinal and Eye Research, 23(4): 435-448, Jul. 2004. p. 446, Pont No. 10.
Wang et al. "Identification of Potential Anticancer Compounds From Oplopanax Horridus", Phytomedicine, 20(11): 999-1006, Aug. 15, 2013.
Wells "Additivity of Mutational Effects in Proteins", Biochemistry, 29(37): 8509-8517, Sep. 18, 1990.
Wilson et al. "CXCR4 Signaling Mediates Morphine-Induced Tactile Hyperalgesia", Brain, Behavior, and Immunity, 25(3): 565-573, Epub Dec. 28, 2010.
Zheng et al. "Migration of Endothelial Progenitor Cells Mediated by Stromal Cell-Derived Factor-1[Alpha]/CXCR4 Via PI3K/Akt/eNOS Signal Transduction Pathway", Journal of Cardiovascular Pharmacology, 50(3): 274-280, Sep. 2007.
Request for Examination dated Oct. 2, 2020 From the (ROSPATENT), Federal Government Institution of Industrial Property of the Federal Service of Intellectual Property, Patents and Trademark of the Russian Federation Re. Application No. 2018125293 and Its Translation Into English. (10 Pages).
Supplementary Partial European Search Report and the European Provisional Opinion dated Aug. 5, 2019 From the European Patent Office Re. Application No. 16875066.9. (18 Pages).
Carreras Puigvert et al. "Targeting DNA Repair, DNA Metabolism and Replication Stress as Anti-Cancer Strategies", The FEBS Journal, XP055607460, 283(2): 232-245, Published Online Oct. 28, 2015.
Williams et al. "Depsides Isolated From the Sri Lankan Lichen Parmotrema Sp. Exhibit Selective Plkl Inhibitory Activity", Pharmaceutical Biology, XP055607658, 49(3): 296-301, Feb. 1, 2011.
Restriction Official Action dated Jul. 2, 2019 From the US Patent and Trademark Office Re. U.S. Appl. No. 16/063,278. (7 pages).
International Preliminary Reort on Patentability dated Jun. 28, 2018 From the International Bureau of WIPO Re. Application No. PCT/IL2016/051346. (11 Pages).
International Preliminary Report on Patentability dated Jun. 28, 2018 From the International Bureau of WIPO Re. Application No. PCT/IL2016/051347. (7 Pages).
Communication Pursuant to Article 94(3) dated Sep. 4, 2020 From the European Patent Office Re. Application No. 16875066.9. (6 Pages).
Examination Report dated Aug. 13, 2020 From the Instituto Mexicano de la Propiedad Industrial, IMPI, Secretario de Economia, Direccion Divisional de Patentes Re. Application No. MX/a/2018/007361. (3 Pages).
Communication Pursuant to Article 94(3) EPC dated Jun. 3, 2019 From the European Patent Office Re. Application No. 16875067.7. (3 Pages).
Supplementary European Search Report and the European Search Opinion dated Sep. 19, 2018 From the European Patent Office Re. Application No. 16875067.7.
Kim et al. "Isolation and Characterization of Antitumor Agents From Dictamnus Albus", Saengyak Hakhoe Chi, 28(4): 209-214, Dec. 28, 1997.
Office Action dated Jun. 11, 2020 From the Israel Patent Office Re. Application No. 260081 and Its Translation Into English. (5 Pages).
Official Action dated Jun. 15, 2020 from the US Patent and Trademark Office Re. U.S. Appl. No. 16/868,558. (9 pages).
Examination Report dated Aug. 19, 2019 From the Australian Government, IP Australia Re. Application No. 2016371466. (2 Pages).

(56) References Cited

OTHER PUBLICATIONS

Official Action dated Sep. 20, 2019 From the US Patent and Trademark Office Re. U.S. Appl. No. 16/063,278. (25 pages).
Request for Examination and Search Report dated Apr. 3, 2020 From the Federal Government Institution, Federal Institute of Industrial Property of the Federal Service of Intellectual Property, Patents and Trademarks of the Russian Federation, FIPS Re. Application No. 2018125293 and Its Translation Into English. (11 Pages).
European Search Report and the European Search Opinion dated Aug. 21, 2020 From the European Patent Office Re. Application No. 20185763.8. (7 Pages).
International Search Report and the Written Opinion dated Jul. 30, 2020 From the International Searching Authority Re. Application No. PCT/IL2020/050535. (11 Pages).
Examination Report Under Sections 12 & 13 of the Patents Act, 1970 and the Patents Rules, 2003 dated Apr. 26, 2020 From the Government of India, Intellectual Property India, Patents, Designs, Trade Marks, Geographical Indications, The Patent Office Re. Application No. 201837025290. (5 Pages).
Notification of Office Action and Search Report dated Nov. 20, 2020 From the State Intellectual Property Office of the People's Republic of China Re. Application No. 201680081132.9 and Its Translation of Office Action Into English. (10 Pages).
Sechi et al. "Design and Synthesis of Novel Dihydroquinoline-3-Carboxylic Acids as HIV-1 Integrase Inhibitors", Bioorganic & Medicinal Chemistry, 17(7): 2925-2935, Available Online Nov. 6, 2008.
Office Action dated Nov. 17, 2019 From the Israel Patent Office Re. Application No. 260082 and Its Translation Into English. (7 Pages).
Supplementary European Search Report and the European Search Opinion dated Nov. 7, 2019 From the European Patent Office Re. Application No. 16875066.9. (13 Pages).
Examination Report dated Jan. 11, 2021 From the Servico Publico Federal, Ministerio da Economia, Instituto Nacional da Propriedade Industrial do Brasil Re Application No. BR1120180123064 and Its Translationsh into English. (7 Pages).
Office Action dated Mar. 11, 2021 From the Israel Patent Office Re. Application No. 277261 and Its Translation Into English. (5 Pages).

* cited by examiner

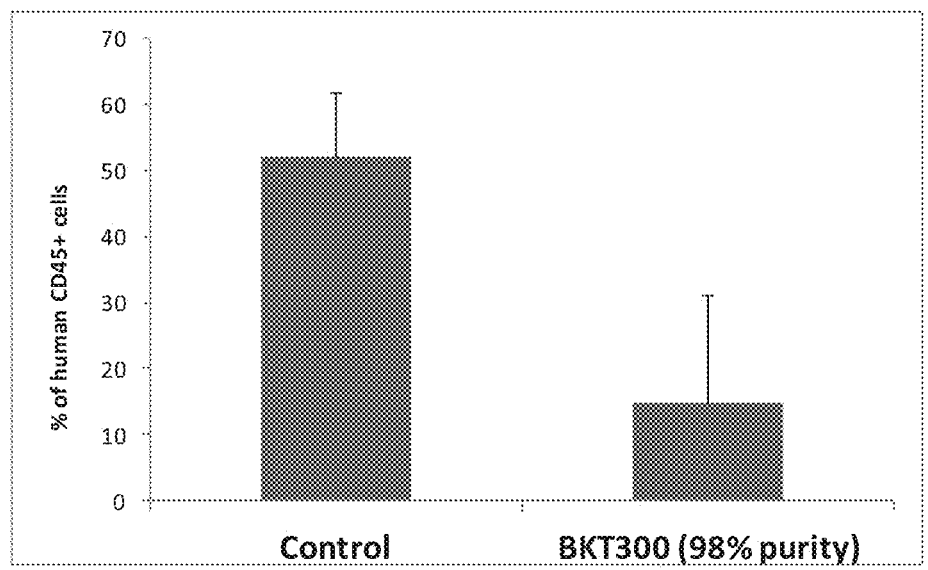
FIG. 12A
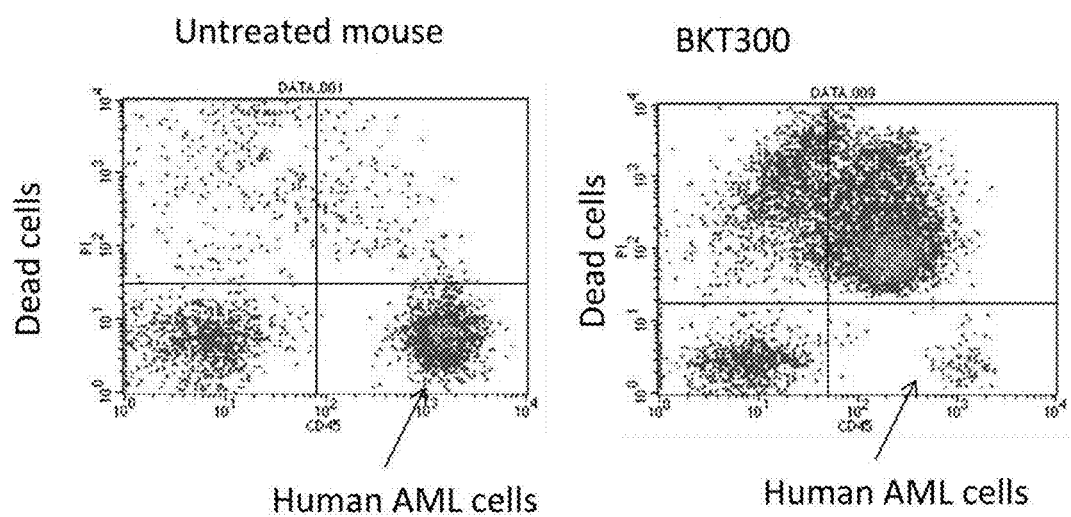
FIG. 12B
FIG. 12C

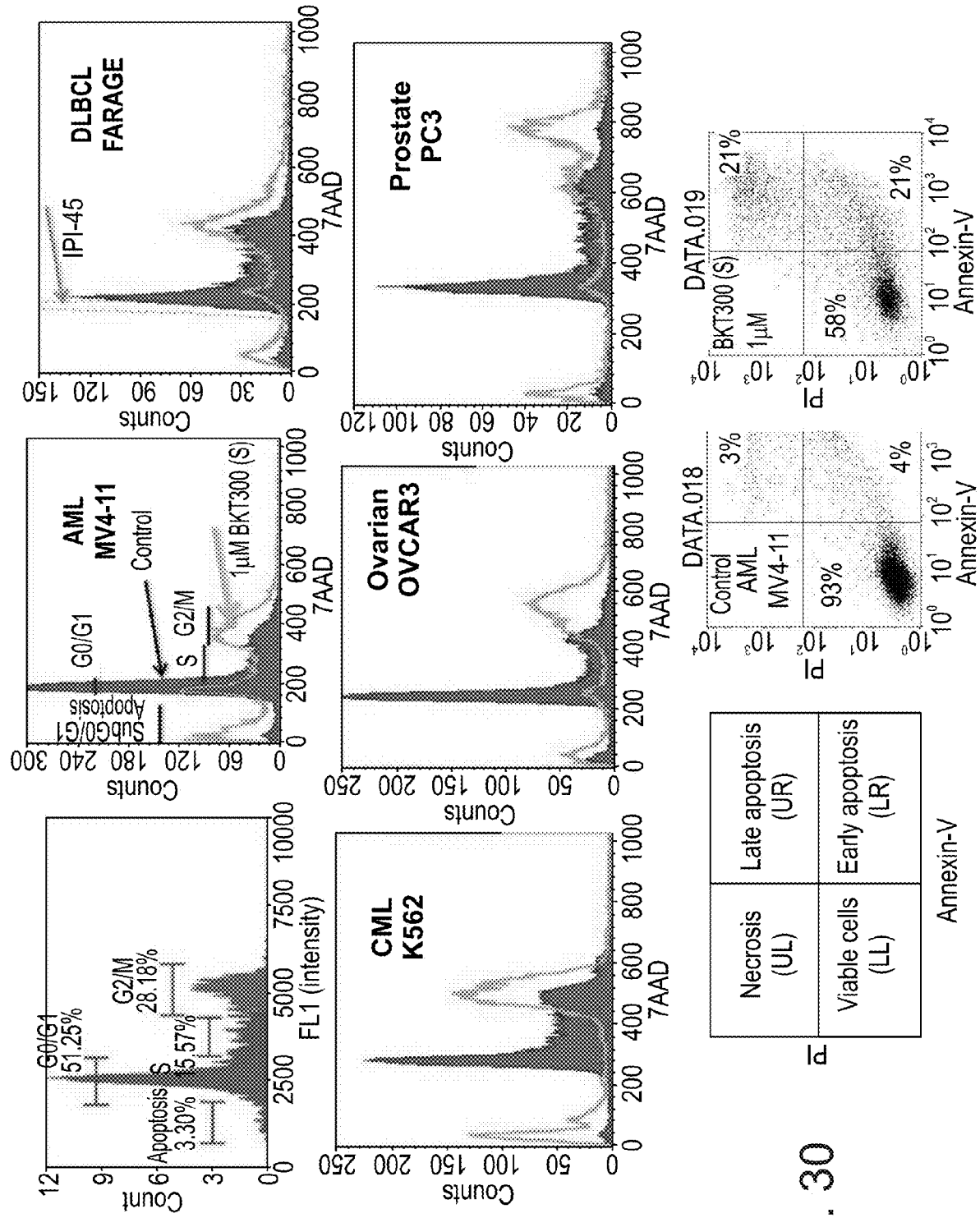

SMALL MOLECULES FOR INHIBITING CHEMOKINE ACTIVITY AND/OR CANCER CELLS GROWTH

RELATED APPLICATIONS

This application is a National Phase of PCT Patent Application No. PCT/IL2016/051347 having International filing date of Dec. 15, 2016, which claims the benefit of priority under 35 USC § 119(e) of U.S. Provisional Patent Application No. 62/268,586 filed on Dec. 17, 2015. The contents of the above applications are all incorporated by reference as if fully set forth herein in their entirety.

FIELD AND BACKGROUND OF THE INVENTION

The present invention, in some embodiments thereof, relates to therapy and more particularly, but not exclusively, to small molecule compounds which are useful in modulating a biological activity of a chemokine, in killing cancer cells, in inhibiting a kinase, in inhibiting chemokine-dependent cell migration and/or in treating diseases and disorders associated with biological activities of chemokines and/or cell migration and/or kinase activity, such as cancer and inflammatory diseases and disorders, and to methods utilizing these compounds.

Chemokines are among the many biological factors that are involved in the inflammatory disease process. Chemokines belong to a group of small, about 8-14 kDa, mostly basic, heparin-binding proteins that are related both in their primary structure and the presence of four conserved cysteine residues.

The chemokines are chemotactic cytokines that have been shown to be selective chemoattractants for leukocyte subpopulations in vitro, and to elicit the accumulation of inflammatory cells in vivo. In addition to chemotaxis, chemokines mediate leukocyte de-granulation [Baggiolini and Dahinden, *Immunol Today* 1994, 15:127-133], up-regulation of adhesion receptors [Vaddi and Newton, *J Immunol* 1994, 153:4721-4732], and suppression of human immunodeficiency virus replication [Cocchi et al., *Science* 1995, 270:1811-1815].

Chemokines play an essential role in the recruitment and activation of cells from the immune system. They also have a wide range of effects in many different cell types beyond the immune system, including for example, in various cells of the central nervous system [Ma et al., *PNAS* 1998, 95:9448-9453], and in endothelial cells, where they result in either angiogenic or angiostatic effects [Strieter et al., *J Biol Chem* 1995, 270:27348-27357]. Particular chemokines may have multiple effects on tumors, including angiogenesis, promotion of growth and metastasis, and suppression of the immune response to cancer, while other chemokines inhibit tumor-mediated angiogenesis and promote anti-tumor immune responses.

Chemokine receptors have received increasing attention due to their critical role in the progression of inflammation and associated conditions such as asthma, atherosclerosis, graft rejection, AIDS and autoimmune conditions (e.g., multiple sclerosis, arthritis, myasthenia gravis, lupus).

SDF-1 (stromal cell-derived factor 1), also known as CXCL12 (C-X-C motif chemokine 12), is a chemokine which is strongly chemotactic for lymphocytes. SDF-1 plays an important role in angiogenesis, including angiogenesis associated with tumor progression, by recruiting endothelial progenitor cells from the bone marrow, an effect mediated by the CXCR4, the receptor for SDF-1 [Zheng et al., *Cardiovasc Pharmacol* 2007, 50:274-280; Kryczek et al., *Am J Physiol Cell Physiol* 2007, 292:C987-C995]. In addition, cancer cells that express CXCR4 are attracted to metastasis target tissues that release SDF-1.

Plerixafor, an antagonist of CXCR4, is used in combination with G-CSF (granulocyte colony-stimulating factor) to mobilize hematopoietic stem cells in cancer patients, particularly lymphoma and multiple myeloma patients. The stem cells are subsequently transplanted back to the patient after chemotherapy or radiotherapy.

In animal studies, plerixafor has also been reported to reduce metastasis [Smith et al., *Cancer Res* 2004, 64:8604-8612], to reduce recurrence of glioblastoma associated with vasculogenesis [Kioi et al., *J Clin Investigation* 2010, 120: 694-705], and to counteract opioid-induced hyperalgesia [Wilson et al., *Brain Behav Immun* 2011, 25:565-573].

Kinases are a family of enzymes that mediate the transfer of a phosphate moiety from a high energy molecule (such as ATP) to a substrate. Kinases are involved in many cell-signaling pathways. Protein kinases act on proteins, phosphorylating serine, threonine, tyrosine, or histidine residues in the protein, and thereby affecting the protein's activity.

Mitogen activated protein kinases (MAPK) constitute a family of proline-directed serine/threonine kinases that activate their substrates by dual phosphorylation. The p38 MAPKs (p38α, p38β, p38γ and p38δ), for example, are responsible for phosphorylating and activating transcription factors (such as ATF-2, MAX, CHOP and C/ERPb) as well as other kinases (such as MAPKAP-K2/3 or MK2/3), and are themselves activated by physical and chemical stress (e.g. UV, osmotic stress), pro-inflammatory cytokines and bacterial lipopolysaccharide (LPS) [Stein et al., *Ann Rep Med Chem* 1996, 31:289-298; Herlaar & Brown, *Molecular Medicine Today* 1999, 5:439-447]. The products of p38 phosphorylation have been shown to mediate the production of pro-inflammatory cytokines.

The implication of kinases pathways on various diseases and disorders, and an anti-inflammatory activity of kinase inhibitors have been described in the art. For example, anti-inflammatory activities have been reported for p38 kinase inhibitors [Badger et al., *J Pharm Exp Thera* 1996, 279:1453-1461; Griswold et al., *Pharmacol Comm* 1996, 7:323-229]. In particular, p38 kinase inhibitors have been described as potential agents for treating rheumatoid arthritis, and to exhibit beneficial effects in models of airway diseases such as COPD and asthma [Haddad et al., *Br J Pharmacol* 2001, 132:1715-1724; Underwood et al., *Am J Physiol Lung Cell Mol* 2000, 279:895-902; Duan et al., *Am J Respir Crit Care Med* 2005, 171:571-578; Escott et al., *Br J Pharmacol* 2000, 131:173-176; Underwood et al., *J Pharmacol Exp Ther* 2000, 293:281-288]. The implication of the p38MAPK pathway in various diseases has been reviewed by Chopra et al. [*Expert Opinion on Investigational Drugs* 2008, 17:1411-1425].

The compound 8-(2,4-dihydroxy-6-(2-oxoheptyl)-phenoxy)-6-hydroxy-3-pentyl-1H-isochromen-1-one was isolated from oakmoss, and reported to exhibit potent antibacterial activity against *Legionella*, but not against other bacteria [Nomura et al., *Biol Pharm Bull* 2012, 35:1560-1567].

SUMMARY OF THE INVENTION

According to an aspect of some embodiments of the present invention, there is provided a compound represented by Formula Ia and/or Ib:

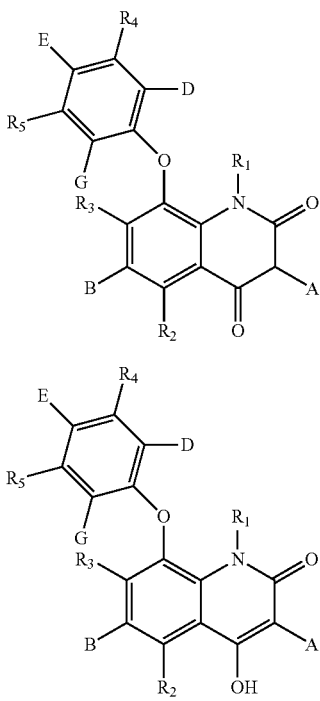

Formula Ia

Formula Ib wherein:
A is an alkyl being at least 4 carbon atoms in length;
B is selected from hydroxy and alkoxy;
D, E and G are each independently selected from hydrogen, hydroxy, alkoxy and alkyl, provided that (i) no more than one of D, E and G is the alkyl, (ii) no more than two of D, E and G are the alkoxy, and (iii) if two of D, E and G are the alkoxy, none of D, E and G is the alkyl;
$R_1$ is selected from hydrogen and alkyl; and
each of $R_2$-$R_5$ is independently selected from hydrogen, hydroxy, halo, alkoxy, thioalkoxy, thiol, thioalkoxy and amine.

According to some of any of the embodiments described herein, B is alkoxy.

According to some of any of the embodiments described herein, E is alkoxy.

According to some of any of the embodiments described herein, D is alkoxy.

According to some of any of the embodiments described herein, G is alkoxy.

According to some of any of the embodiments described herein, D is alkoxy, and D and E are both hydrogen.

According to some of any of the embodiments described herein, E is alkoxy, and D and G are both hydrogen.

According to some of any of the embodiments described herein, G is alkoxy, and D and E are both hydrogen.

According to some of any of the embodiments described herein, E and D are each independently alkoxy, and G is hydrogen.

According to some of any of the embodiments described herein, G is hydrogen.

According to some of any of the embodiments described herein, D is the alkyl.

According to some of any of the embodiments described herein, G is hydrogen.

According to some of any of the embodiments described herein, when one of D, E and G is alkyl, the alkyl is at least 4 carbon atoms in length.

According to some of any of the embodiments described herein, $R_1$ is hydrogen.

According to some of any of the embodiments described herein, each of $R_2$-$R_5$ is hydrogen.

According to some of any of the embodiments described herein, the compound is:

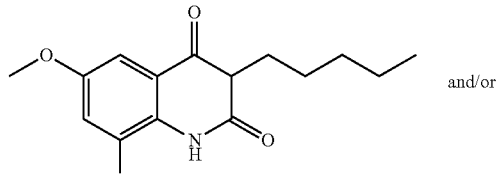 and/or

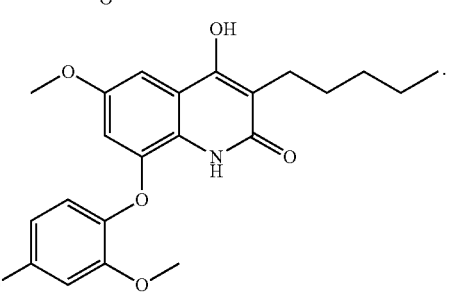.

According to some of any of the embodiments described herein, the compound is:

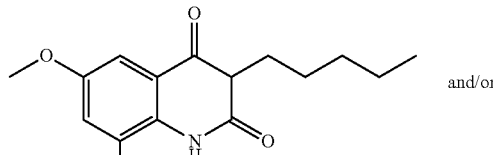 and/or

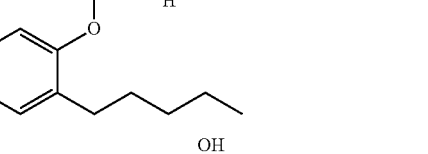

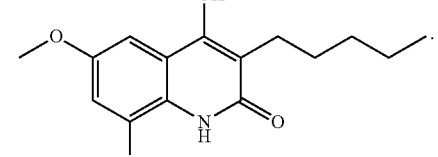.

According to some of any of the embodiments described herein, the compound is:

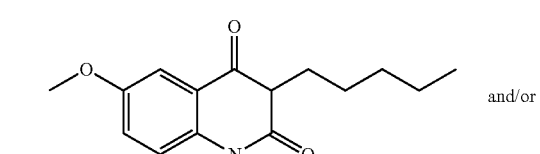 and/or

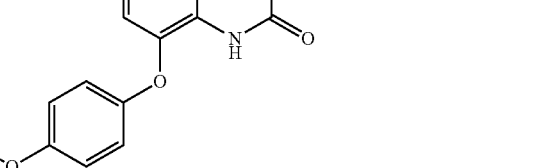

-continued

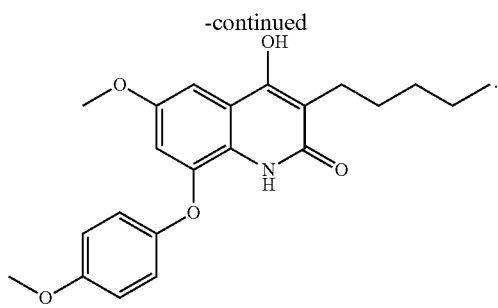

According to some of any of the embodiments described herein, the compound is:

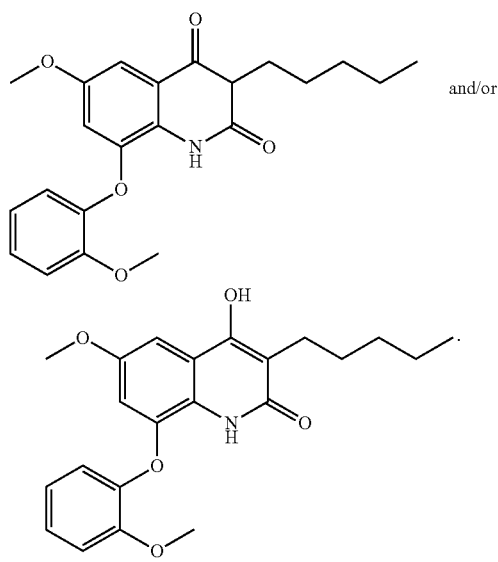

and/or

According to some of any of the embodiments described herein, the compound is capable of inducing cells death.

According to some of any of the embodiments described herein, the compound capable of inducing apoptosis in cells.

According to some of any of the embodiments described herein, the apoptosis is associated with cleavage of caspase-3.

According to some of any of the embodiments described herein, the compound is capable of inducing arrest of cancer cell growth at the G2M phase of cancer cells.

According to some of any of the embodiments described herein, the compound is capable of inhibiting chemokine-induced cell migration.

According to some of any of the embodiments described herein, the compound is capable of inhibiting an activity of a kinase.

According to some of any of the embodiments described herein, the kinase is selected from the group consisting of DYRK3, EPHA8, GRK4, GRK5, MAP4K1, MAP4K2, MAP4K4, MELK, PAK7, SGK2, SRC N1, ACVRL1, BMPR1A, CDC7/DBF4, CDK1/cyclin A2, CDK11, CDK8/cyclin C, CLK4, DAPK2, DURK2, ICK, MAPK10, MLCK, MYLK, NUAK2, STK17A, STK17B, STK38, STK38L, TGFBR2, TTK, DAPK1 and PI3K.

According to an aspect of some embodiments of the present invention, a compound represented by Formula Ia and/or Ib as described herein in any of the respective embodiments and any combination thereof is for use in treating cancer in a subject in need thereof.

According to some of any of the embodiments described herein, the cancer is a leukemia.

According to some of any of the embodiments described herein, the cancer is selected from a leukemia, a melanoma, a lung cancer, a lymphoma, a myeloma, an ovarian cancer, a brain cancer and prostate cancer.

According to some of any of the embodiments described herein, the cancer is characterized by expression of CXCR4.

According to some of any of the embodiments described herein, treating the cancer further comprises administering to the subject an additional anti-cancer agent.

According to an aspect of some embodiments of the present invention, a compound represented by Formula Ia and/or Ib as described herein in any of the respective embodiments and any combination thereof is for use in modulating a biological activity of a chemokine in a subject in need thereof.

According to an aspect of some embodiments of the present invention, a compound represented by Formula Ia and/or Ib as described herein in any of the respective embodiments and any combination thereof is for use in treating a condition treatable by modulating a biological activity of a chemokine.

According to some of any of the embodiments described herein, the chemokine is MCP-1 and/or SDF-1.

According to an aspect of some embodiments of the present invention, a compound represented by Formula Ia and/or Ib as described herein in any of the respective embodiments and any combination thereof is for use in inhibiting a kinase and/or in treating a disease or disorder associated with an activity of a kinase.

According to some of any of the embodiments described herein, the kinase is selected from the group consisting of DYRK3, EPHA8, GRK4, GRK5, MAP4K1, MAP4K2, MAP4K4, MELK, PAK7, SGK2, SRC N1, ACVRL1, BMPR1A, CDC7/DBF4, CDK1/cyclin A2, CDK11, CDK8/cyclin C, CLK4, DAPK2, DURK2, ICK, MAPK10, MLCK, MYLK, NUAK2, STK17A, STK17B, STK38, STK38L, TGFBR2, TTK, DAPK1 and PI3K.

According to some of any of the embodiments described herein, the kinase is selected from the group consisting of MAP4K4, MELK and PI3K.

According to some of any of the embodiments described herein, the disease or disorder is cancer.

According to an aspect of some embodiments of the present invention, a compound represented by Formula Ia and/or Ib as described herein in any of the respective embodiments and any combination thereof is for use in treating inflammation.

According to an aspect of some embodiments of the present invention, a compound represented by Formula Ia and/or Ib as described herein in any of the respective embodiments and any combination thereof is for use in treating a non-cancerous hyperproliferative disease.

According to an aspect of some embodiments of the present invention, a compound represented by Formula Ia and/or Ib as described herein in any of the respective embodiments and any combination thereof is for use in inducing cell death.

According to an aspect of some embodiments of the present invention, a compound represented by Formula Ia and/or Ib as described herein in any of the respective embodiments and any combination thereof is for use in inducing apoptosis in cells.

According to some of any of the embodiments described herein, the apoptosis is associated with cleavage of caspase-3.

According to some of any of the embodiments described herein, the cells are cancer cells.

According to an aspect of some embodiments of the present invention, a compound represented by Formula Ia and/or Ib as described herein in any of the respective embodiments and any combination thereof is for use in inducing arrest of cancer cell growth at the G2M phase of cancer cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a bar graph showing the effect of Compound BKT300 (at 78% purity) (at concentrations of 10 and 50 µg/ml) on migration of CD4+ cells towards MIP3a (* indicates p<0.05 vs. zero concentration).

Figure 2A:
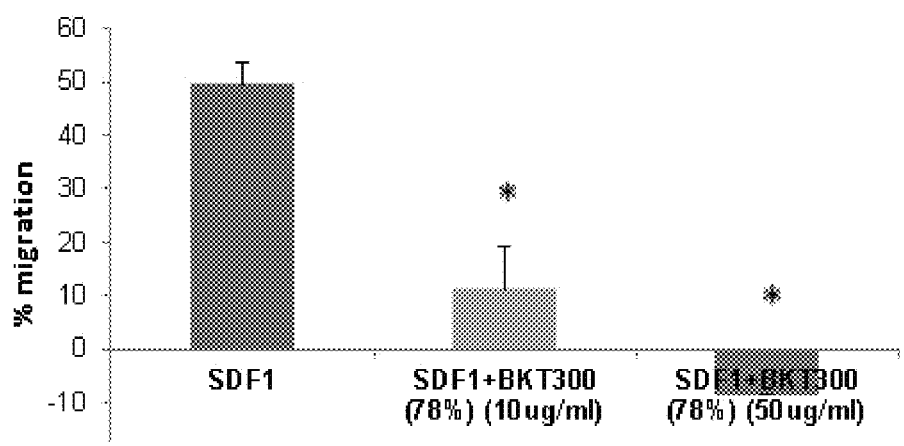
Figure 2B:
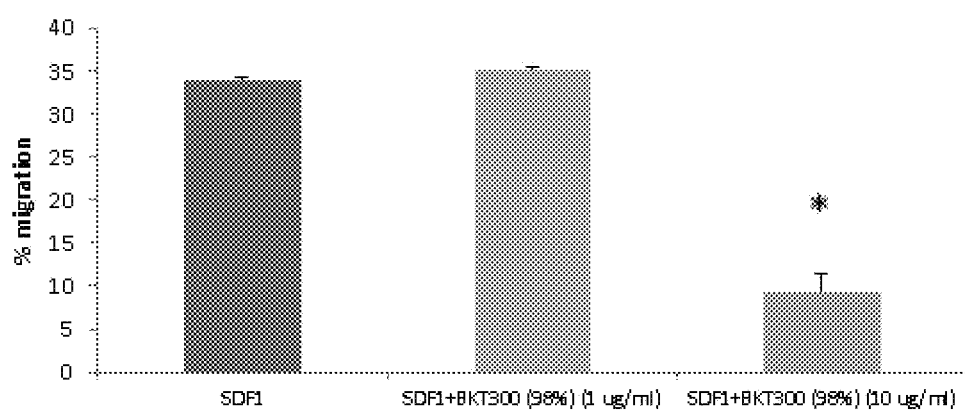
Figure 2C:
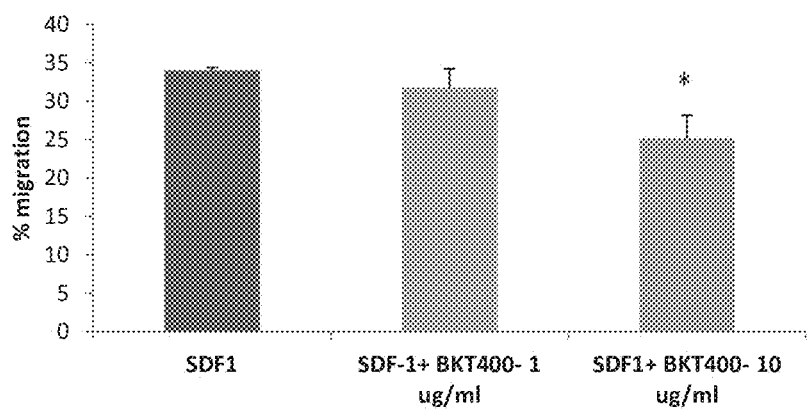

FIGS. 2A-C are bar graphs showing the effect of 10 and 50 µg/ml of BKT300 (at 78% purity) (FIG. 2A); of 1 and 10 µg/ml of Compound BKT300 (at 98% purity) (FIG. 2B); of 1 and 10 µg/ml of Compound BKT400 (FIG. 2C) on migration of Jurkat cells towards SDF-1 (* indicates p<0.05 vs. zero concentration).

Figure 3:
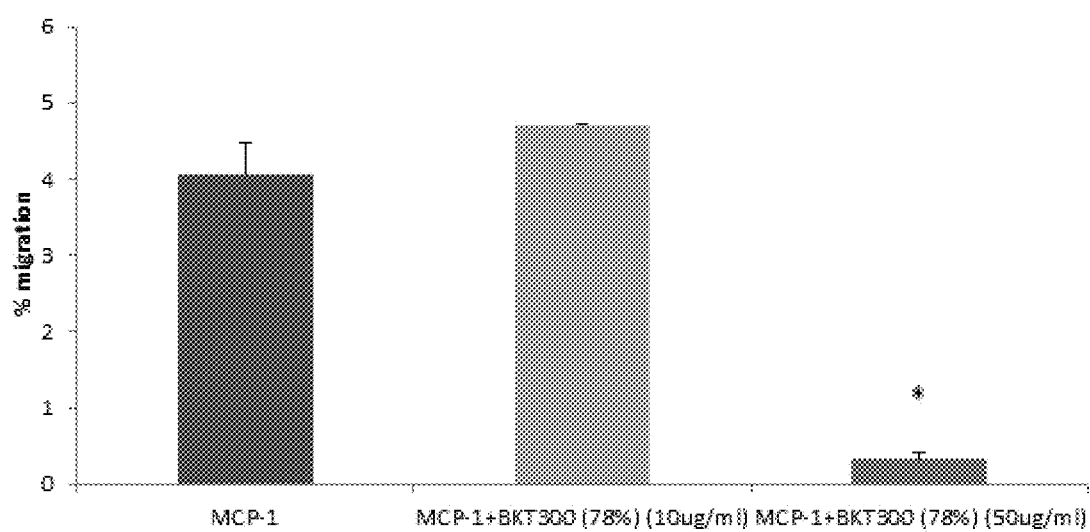

FIG. 3 is a bar graph showing the effect of 10 and 50 µg/ml of Compound BKT300 (at 78% purity) on migration of THP-1 cells towards MCP-1 (* indicates p<0.05 vs. zero concentration).

Figure 4A:
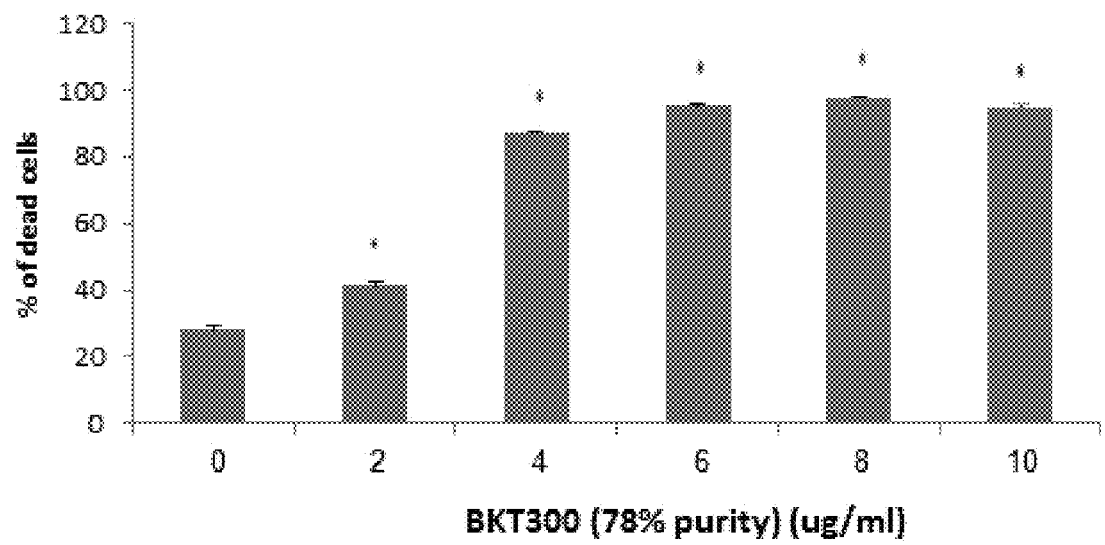
Figure 4B:
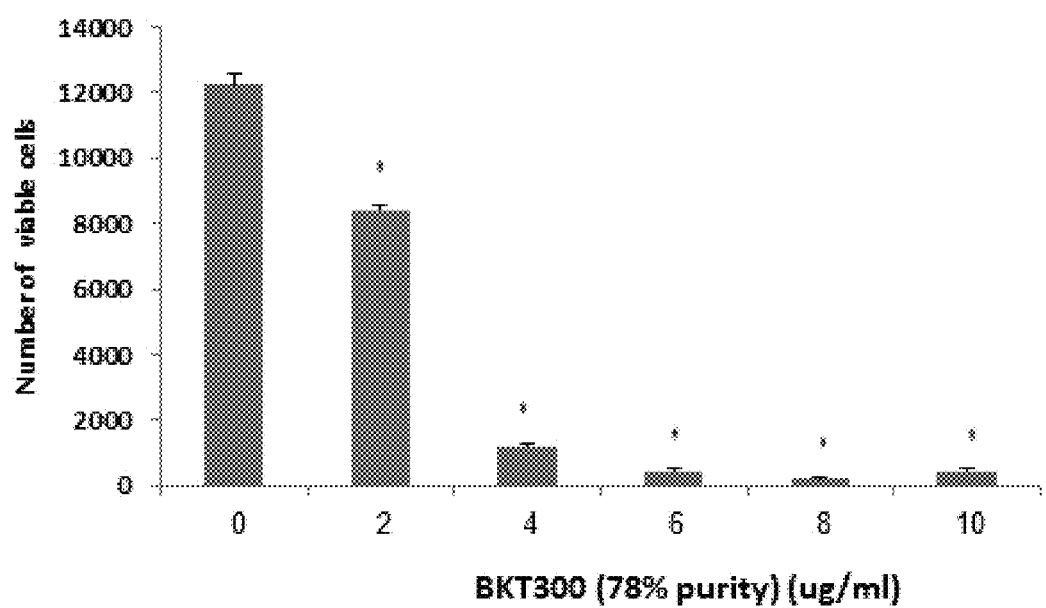
Figure 5A:
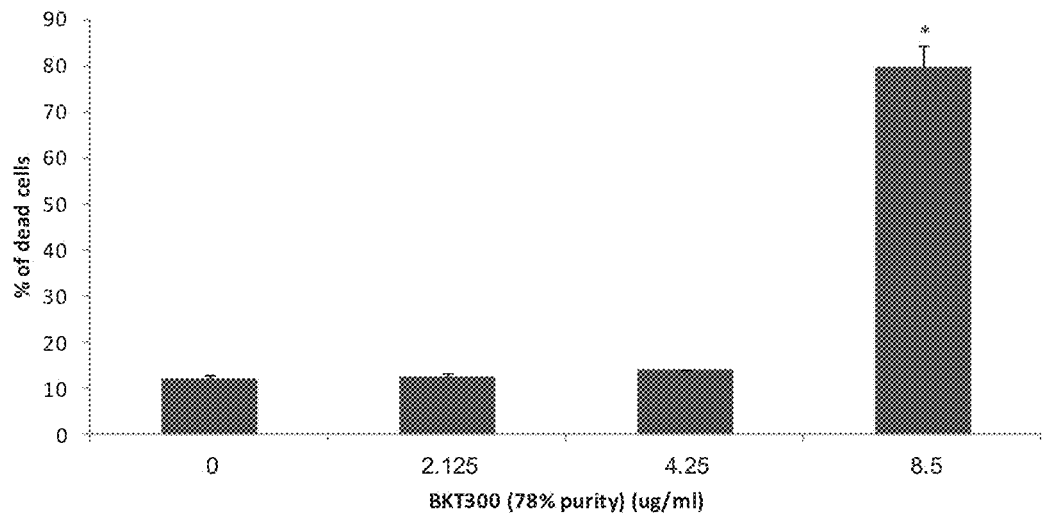
Figure 5B:
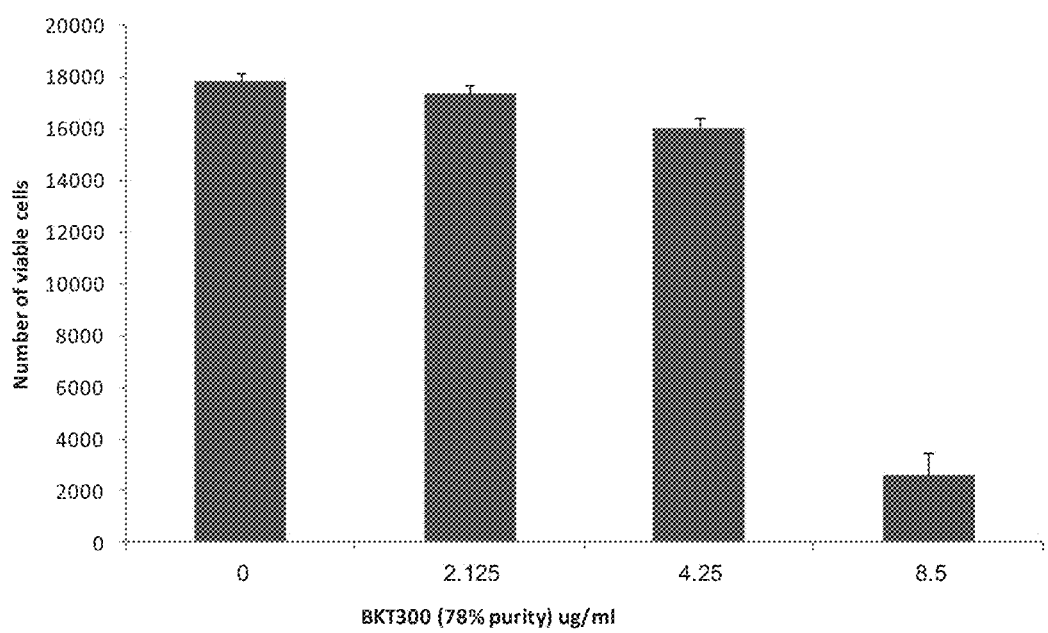
Figure 5C:
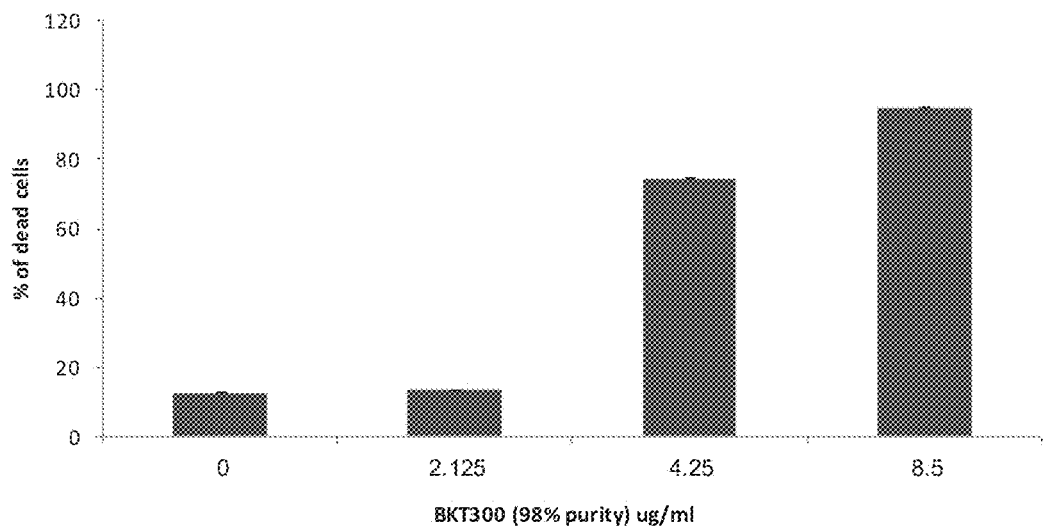
Figure 5D:
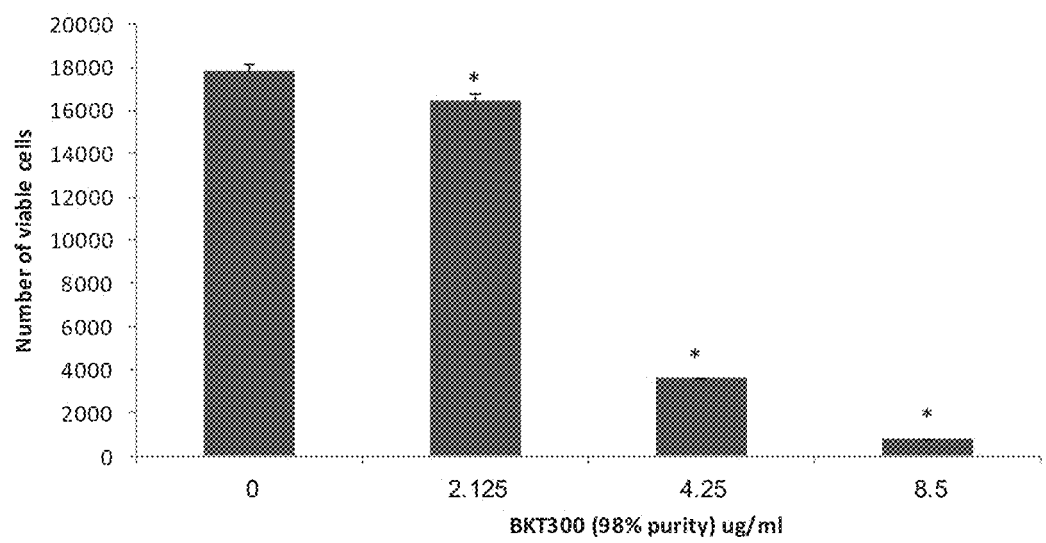

FIGS. 4A and 4B are bar graphs showing the effect of 0, 2, 4, 6, 8 and 10 µg/ml of BKT300 (at 78% purity) on the viability of MV4-11 cells, as expressed by percentage of dead cells (FIG. 4A) and the number of viable cells (FIG. 4B), as determined by propidium iodide staining (* indicates p<0.05 vs. zero concentration).

FIGS. 5A-5D are bar graphs showing the effect of 0, 2.125, 4.25 and 8.5 µg/ml of BKT300 at 78% purity (FIGS. 5A and 5B) and at 98% purity (FIGS. 5C and 5D) on the viability of MV4-11 cells, as expressed by percentage of dead cells (FIGS. 5A and 5C) and the number of viable cells (FIGS. 5B and 5D), as determined by propidium iodide staining (* indicates p<0.05 vs. zero concentration).

Figure 6A:
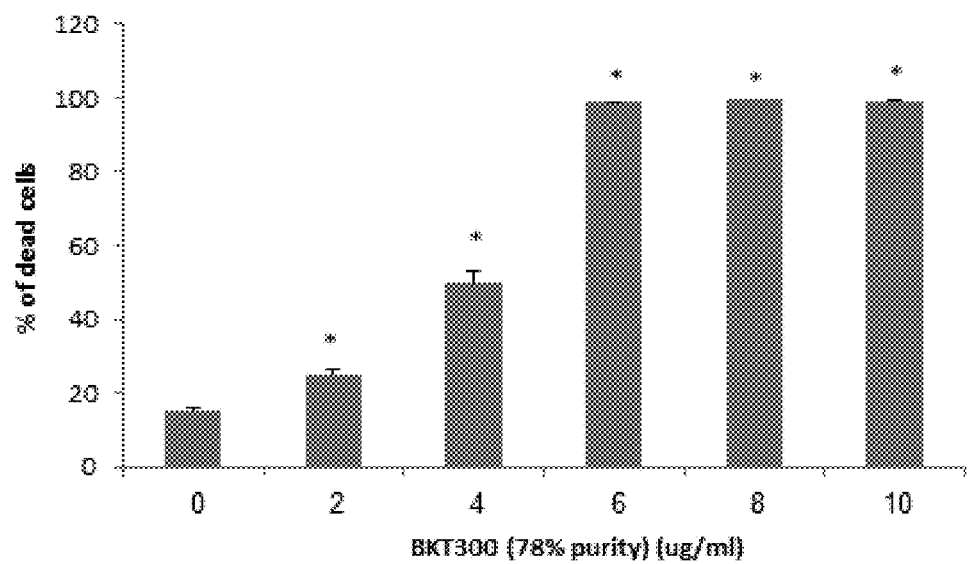
Figure 6B:
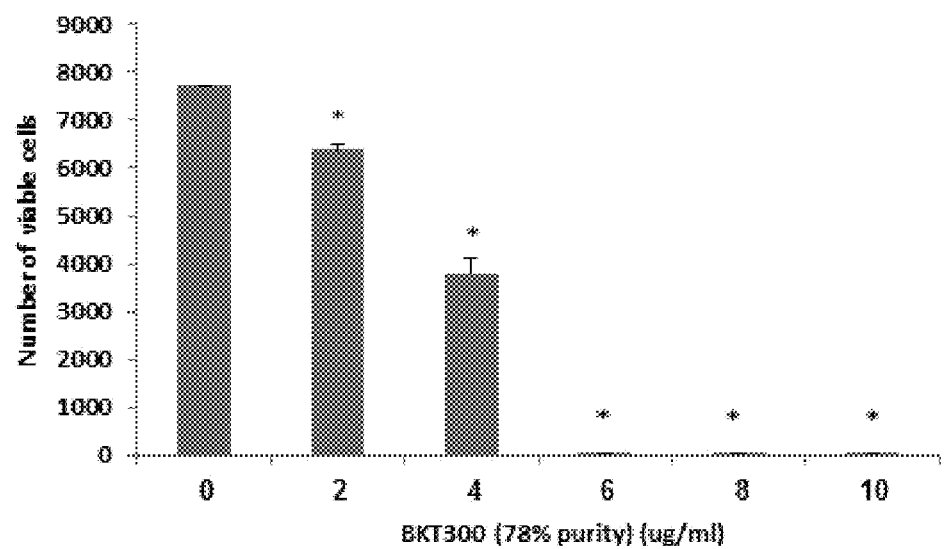

FIGS. 6A and 6B are bar graphs showing the effect of 0, 2, 4, 6, 8 and 10 µg/ml of BKT300 (at 78% purity) on the viability of RPMI cells, as expressed by percentage of dead cells (FIG. 6A) and the number of viable cells (FIG. 6B), as determined by propidium iodide staining (* indicates p<0.05 vs. zero concentration).

Figure 7A:
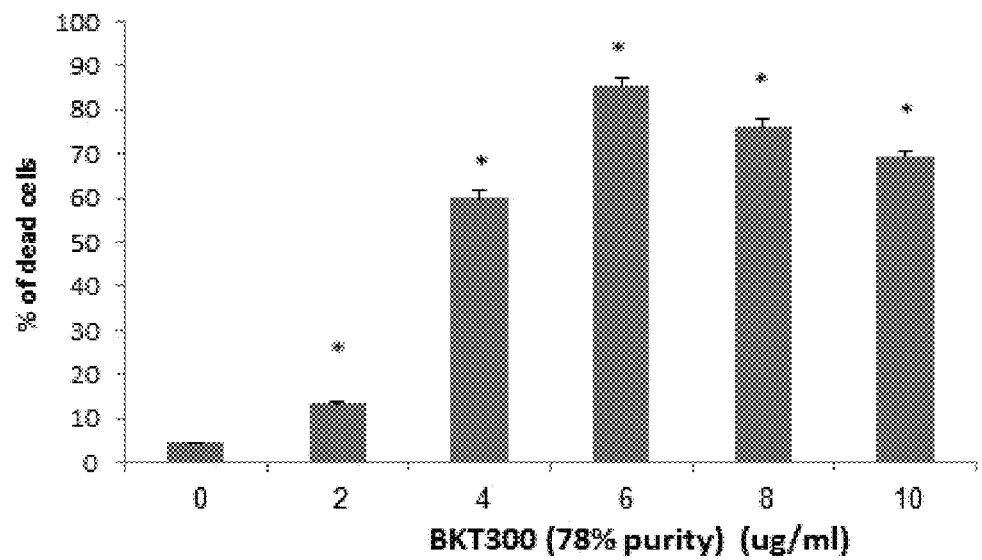
Figure 7B:
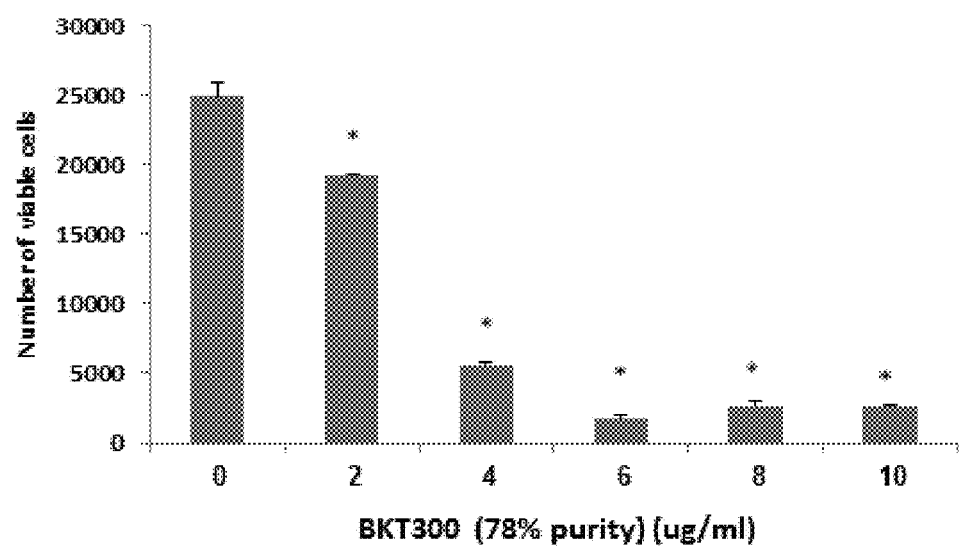

FIGS. 7A and 7B are bar graphs showing the effect of 0, 2, 4, 6, 8 and 10 µg/ml of BKT300 (at 78% purity) on the viability of Jurkat cells, as expressed by percentage of dead cells (FIG. 7A) and the number of viable cells (FIG. 7B), as determined by propidium iodide staining (* indicates p<0.05 vs. zero concentration).

Figure 8A:
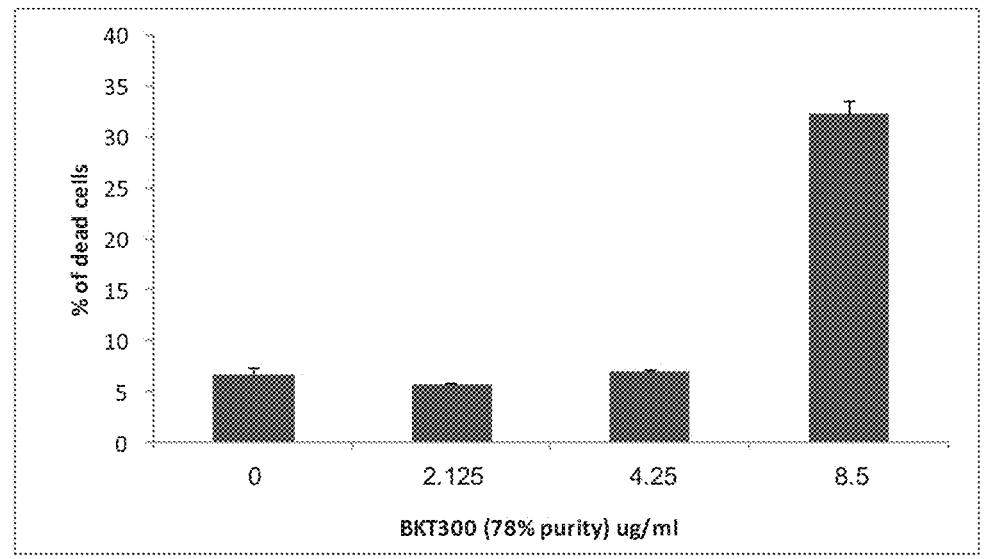
Figure 8B:
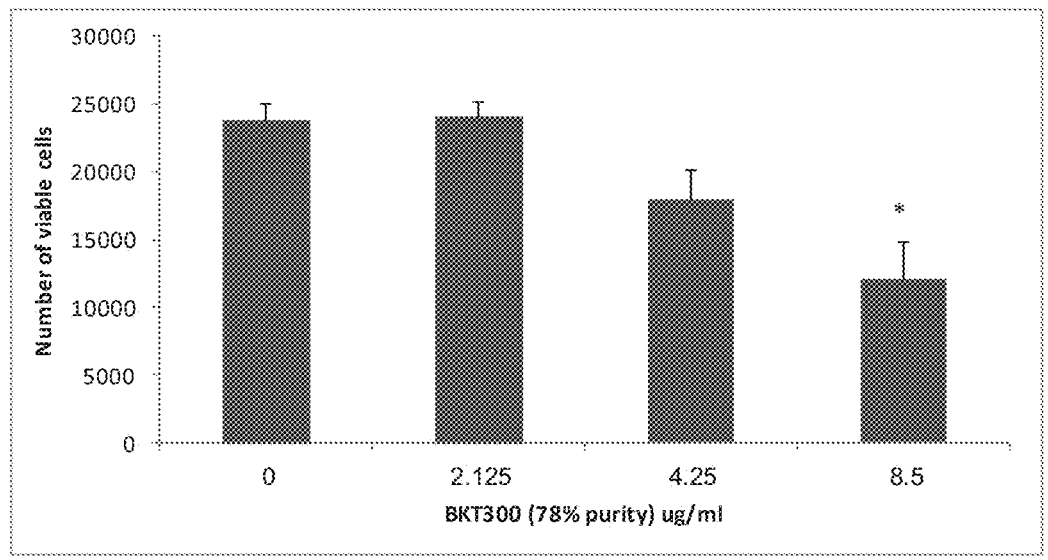

FIGS. 8A and 8B are bar graphs showing the effect of 0, 2.125, 4.25 and 8.5 µg/ml of BKT300 (at 78% purity) on the viability of Raji cells, as expressed by percentage of dead cells (FIG. 8A) and the number of viable cells (FIG. 8B), as determined by propidium iodide staining (* indicates p<0.05 vs. zero concentration).

Figure 9A:
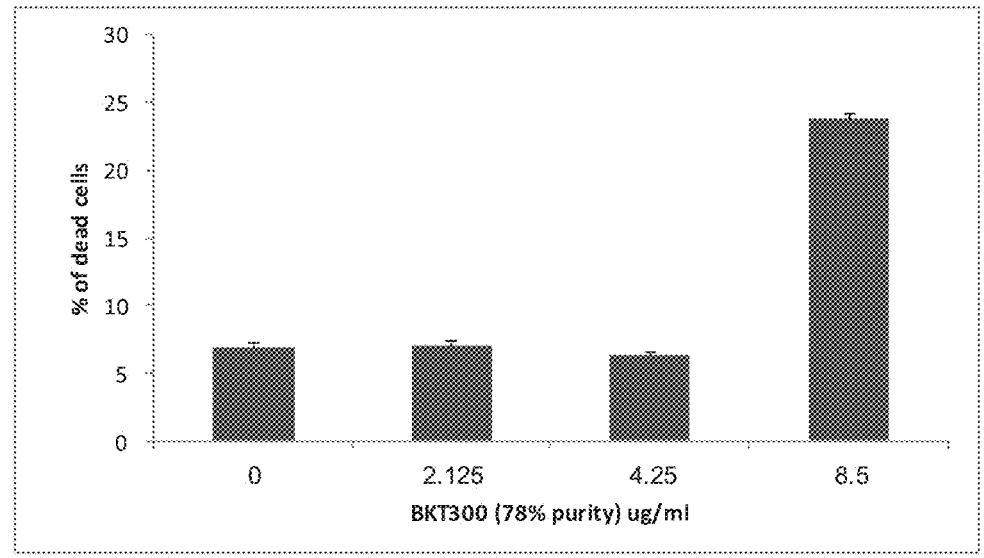
Figure 9B:
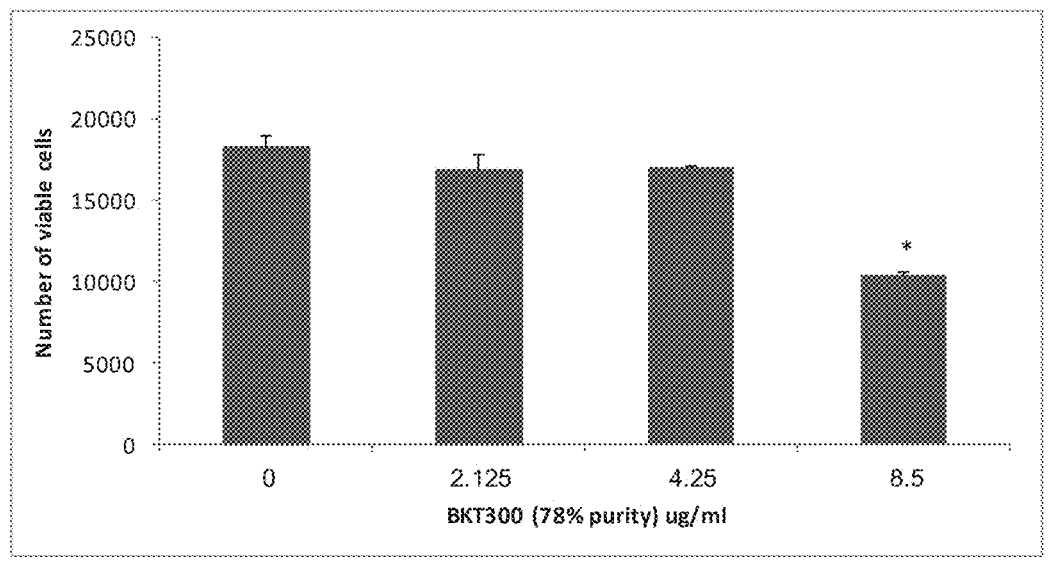

FIGS. 9A and 9B are bar graphs showing the effect of 0, 2.125, 4.25 and 8.5 µg/ml of BKT300 (at 78% purity) on the viability of Bjab cells, as expressed by percentage of dead cells (FIG. 9A) and the number of viable cells (FIG. 9B), as determined by propidium iodide staining (* indicates p<0.05 vs. zero concentration).

Figure 10A:
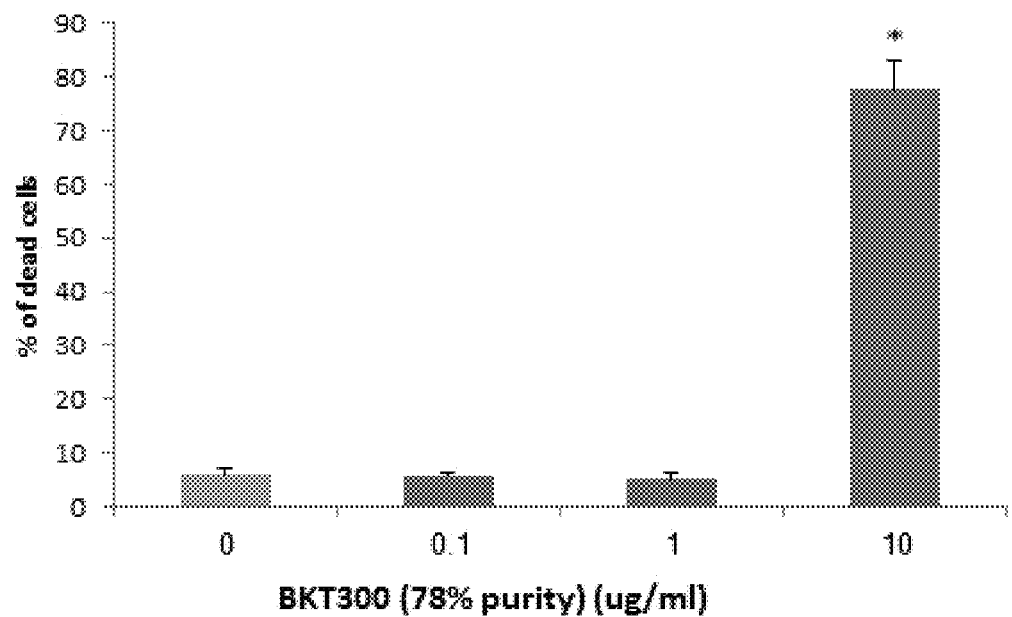
Figure 10B:
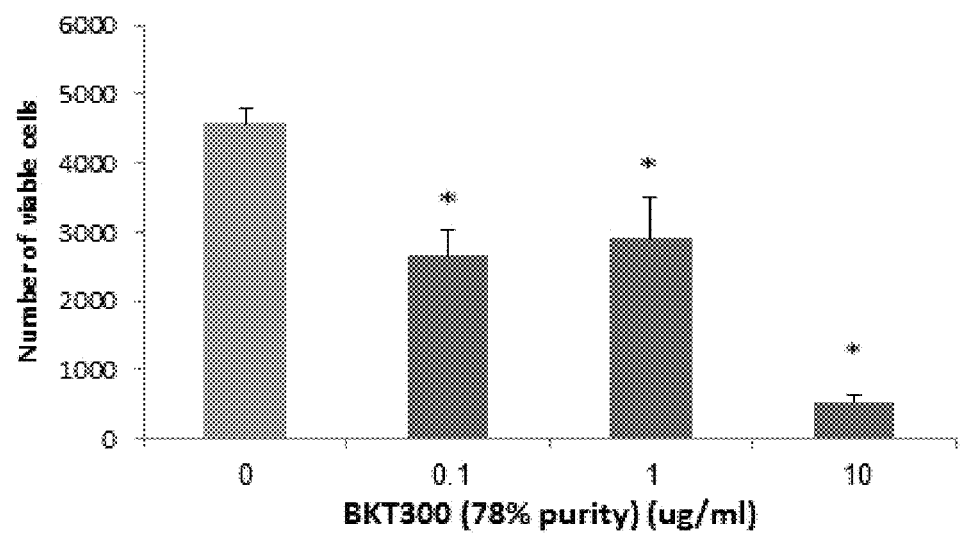

FIGS. 10A and 10B are bar graphs showing the effect of 0, 0.1, 1 and 10 µg/ml of BKT300 (at 78% purity) on the viability of H-460 cells, as expressed by percentage of dead cells (FIG. 10A) and the number of viable cells (FIG. 10B), as determined by propidium iodide staining (* indicates p<0.05 vs. zero concentration).

Figure 11A:
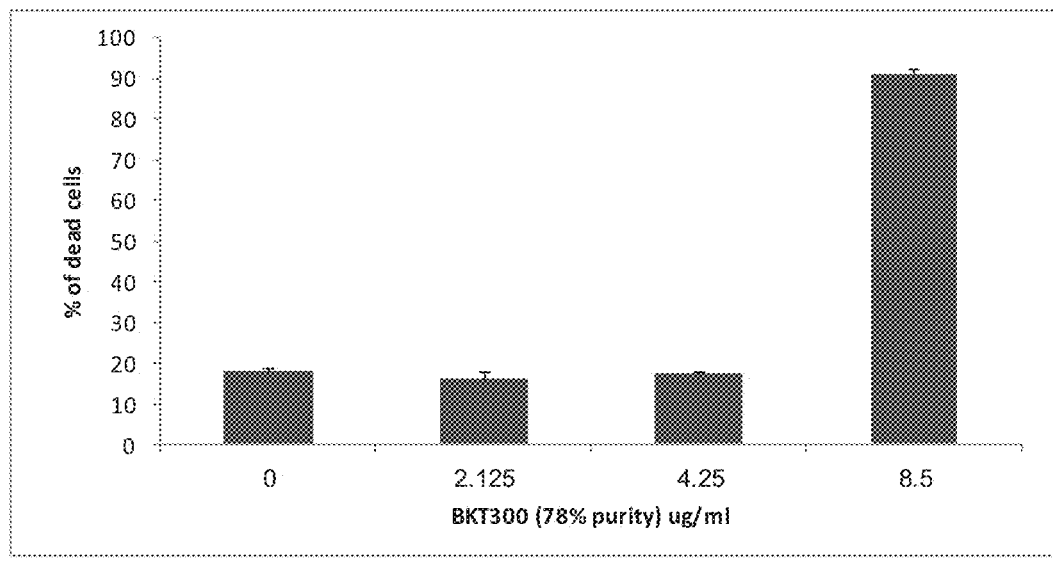
Figure 11B:
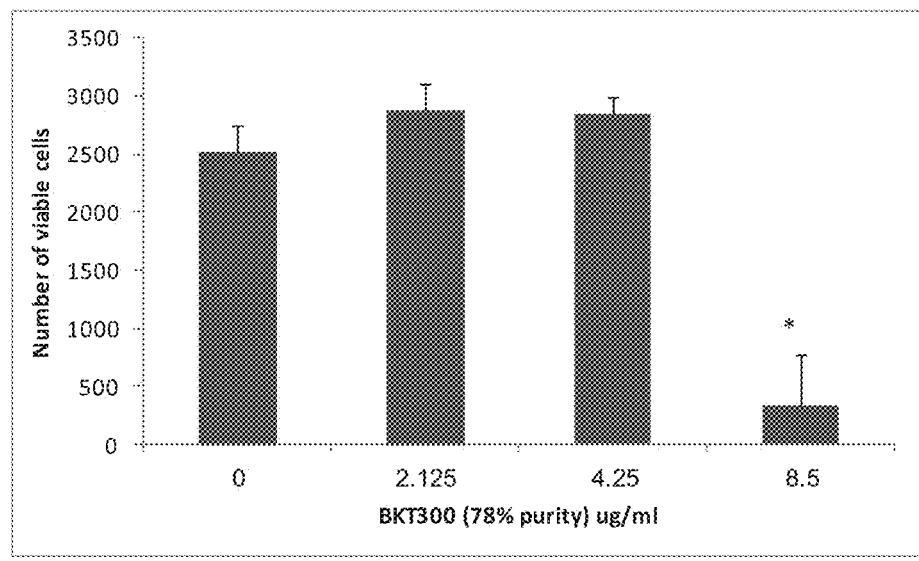

FIGS. 11A and 11B are bar graphs showing the effect of 0, 2.125, 4.25 and 8.5 µg/ml of BKT300 (at 78% purity) on the viability of H345 cells, as expressed by percentage of dead cells (FIG. 11A) and the number of viable cells (FIG. 11B), as determined by propidium iodide staining (* indicates p<0.05 vs. zero concentration).

FIGS. 12A-C present bar graphs showing the effect of intraperitoneal administration of BKT300 (at 98% purity) on the percentage of CD45-positive cells in the bone marrow of mice injected with $10 \times 10^6$ MV4-11 cancer cells 21 days before administration of BKT300 (FIG. 12A), and data of the FACS analysis showing human MV4-11 cancer cells in the bone marrow of untreated (FIG. 12B) and treated with BKT300 (FIG. 12C) mouse 21 days following transplantation of $10 \times 10^6$ MV4-11 cancer cells.

Figure 13:
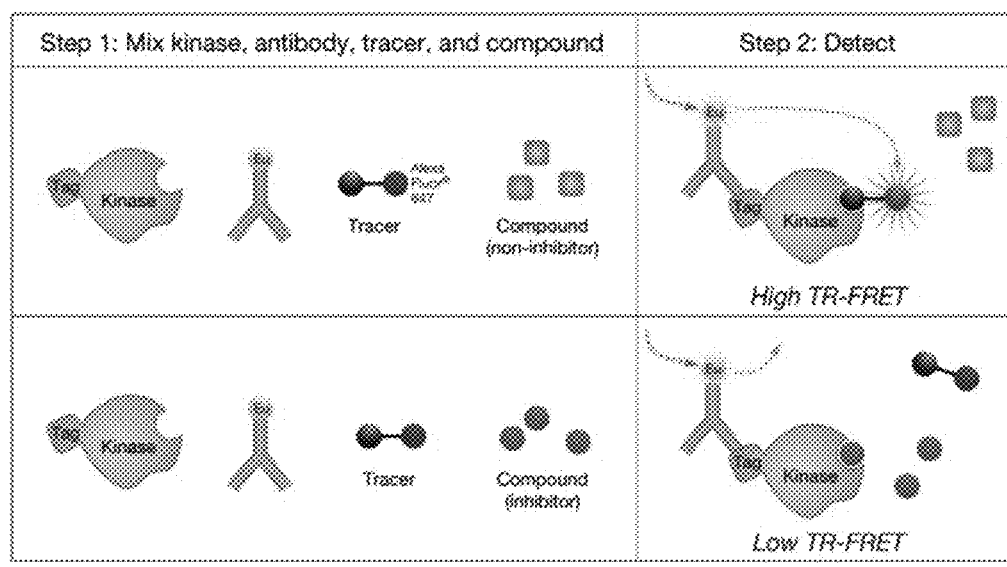

FIG. 13 presents a scheme showing the principles of a FRET assay for determining binding of a compound (inhibitor) to an active site of kinases, wherein resonant energy transfer of energy from a europium (Eu)-labeled antibody which binds to the kinase to an Alexa Fluor®-labeled tracer which binds to the active site is prevented by a compound (inhibitor) which binds to the active site.

Figure 14:
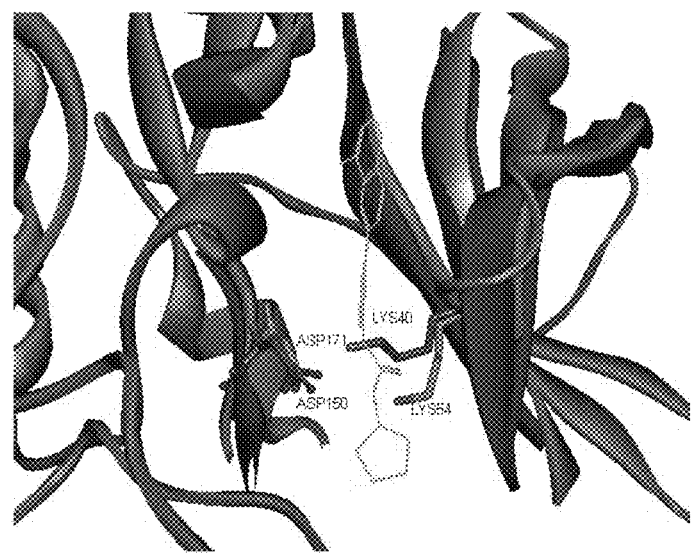

FIG. 14 presents an illustration of the alignment of MELK and MAPK4K active sites; MELK is shown in blue (PDB 4BKY); MAPK4K is shown in green (PDB 4OBQ); the small molecule is an inhibitor of MAPK4K (PDB 4OBQ).

Figure 15:
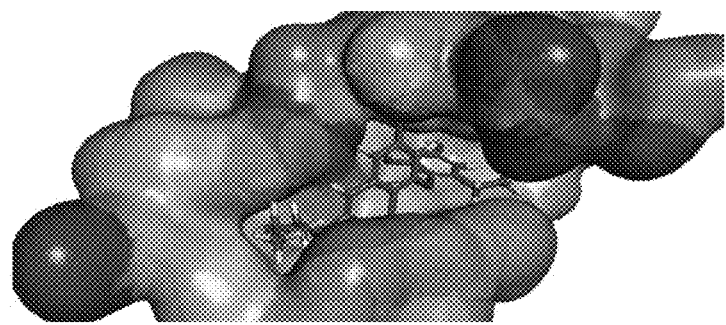

FIG. 15 is an illustration of BKT300 docked into the ATP binding pocket of MELK.

Figure 16:
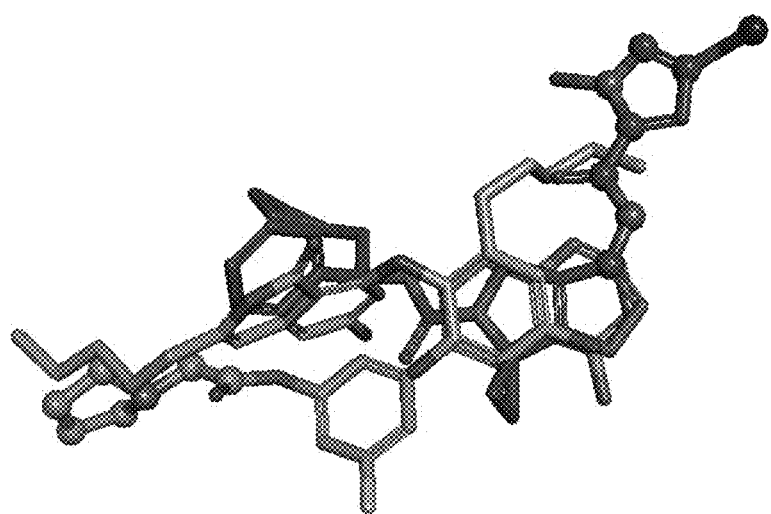

FIG. 16 is an illustration showing BKT300 (in pink) overlaid on a representative small molecule inhibitor of MAPK4K (PDB 4OBQ; in green), and a representative small molecule inhibitor of MELK (PDB 4BKY; in blue); the atoms of the known inhibitors that are close to the aliphatic tails of BKT300 are marked as balls.

Figure 17:
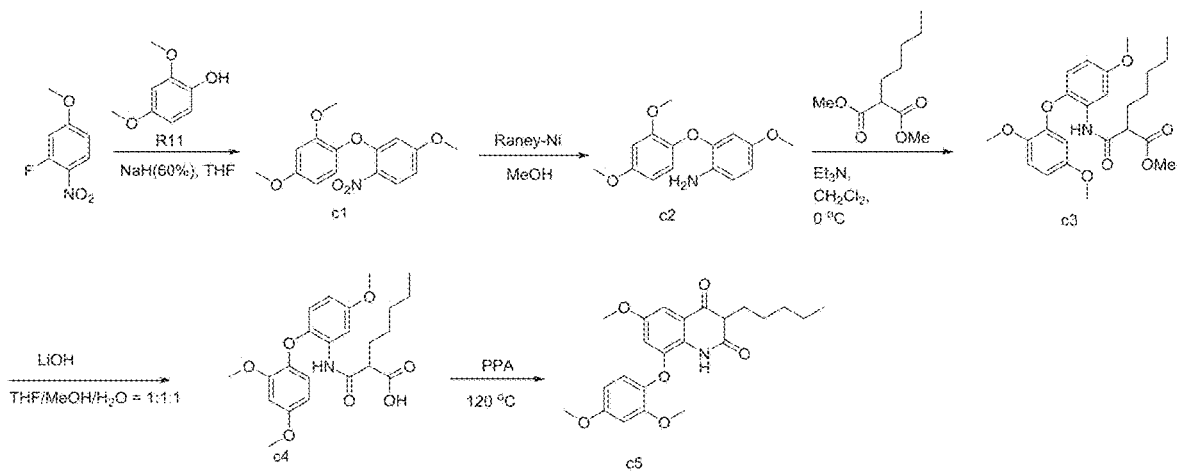

FIG. 17 presents schemes depicting a synthesis of BKT300-3-c5, according to some embodiments of the present invention.

Figure 18:
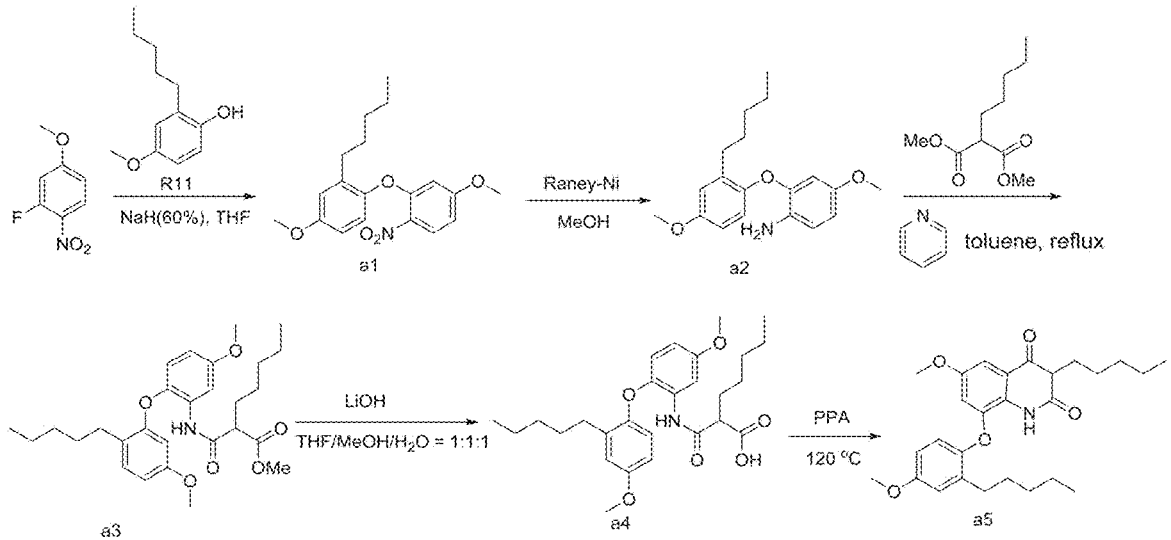

FIG. 18 presents schemes depicting a synthesis of BKT300-11-a5, according to some embodiments of the present invention.

Figure 19A:
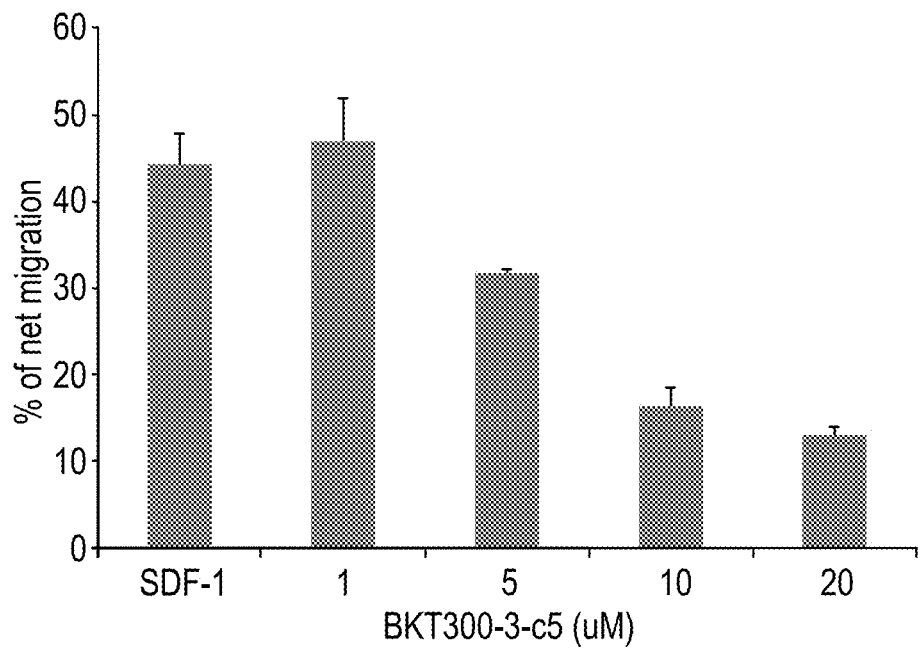
Figure 19B:
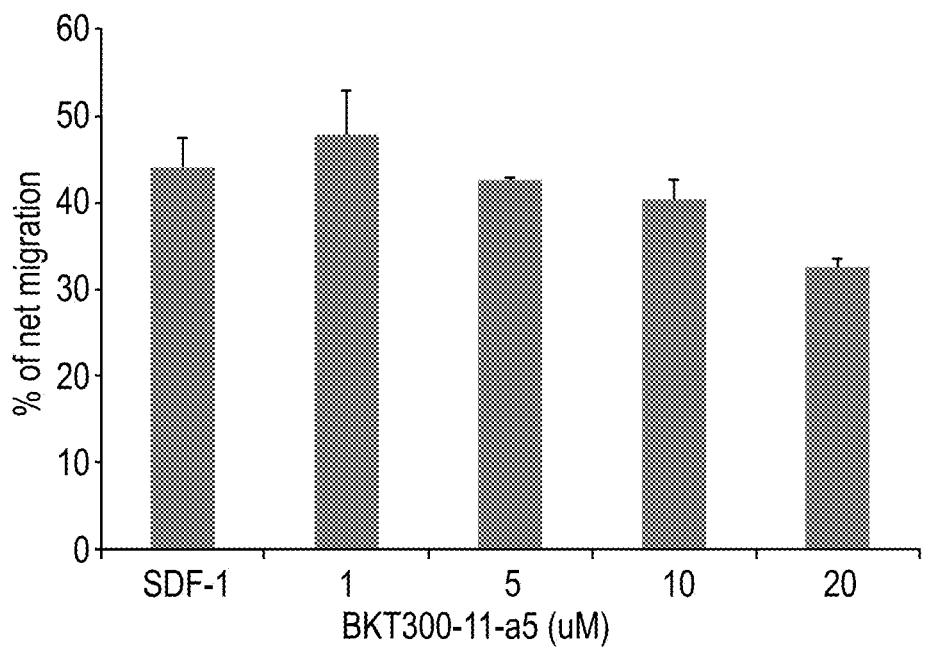

FIGS. 19A-B are bar graphs showing the effect of 1, 5, 10 and 50 µM of BKT300-3-c5 (FIG. 19A), and of 1, 5, 10 and 50 µM of Compound BKT300-11-a5 (FIG. 19B), on migration of Jurkat cells towards SDF-1.

Figure 20A:
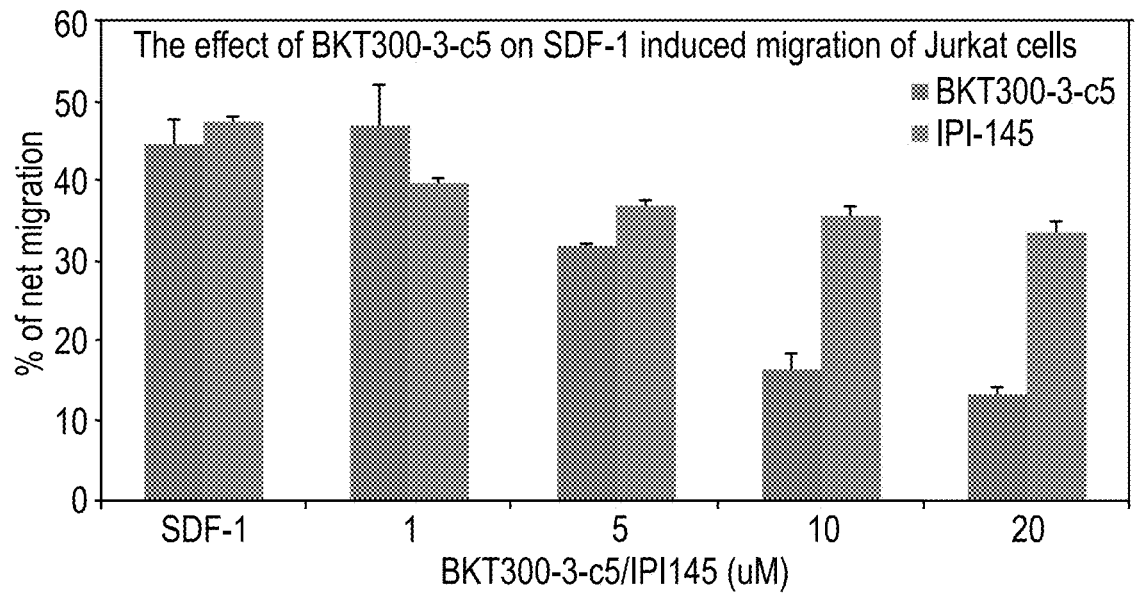
Figure 20B:
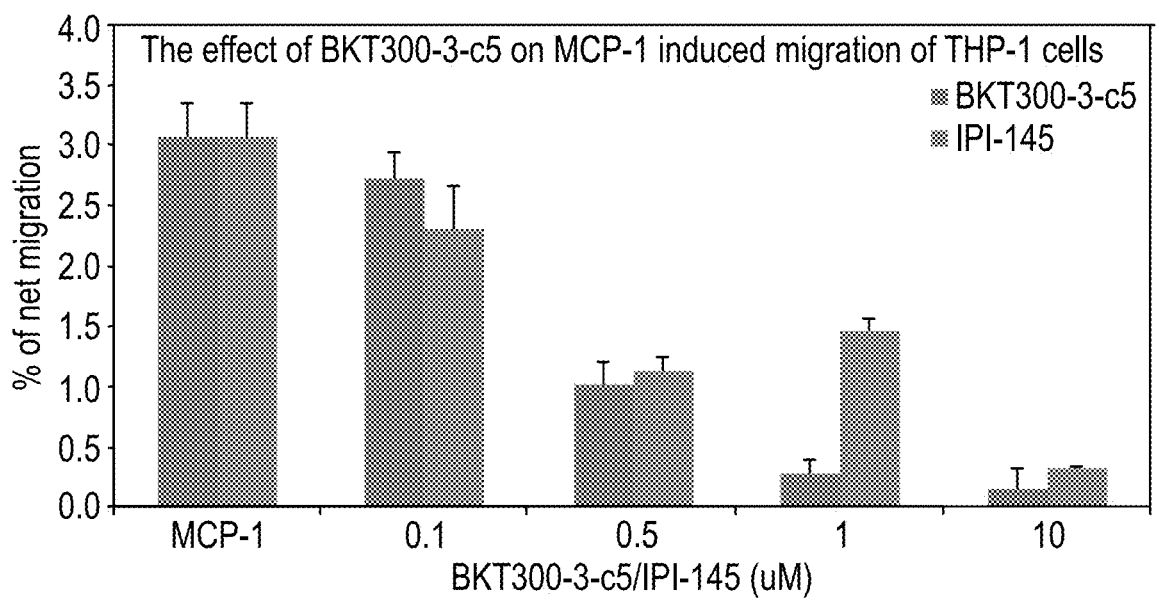

FIGS. 20A-B are comparative bar graphs showing the effect of 1, 5, 10 and 20 µM of Compound BKT300-3-c5 and of IPI-145 on migration of Jurkat cells towards SDF-1 (FIG. 20A), and of 0.1, 0.5, 1 and 10 µM of Compound BKT300-3-c5 and of IPI-145 on migration of THP-1 cells towards MCP-1 (FIG. 20B).

Figure 21A:
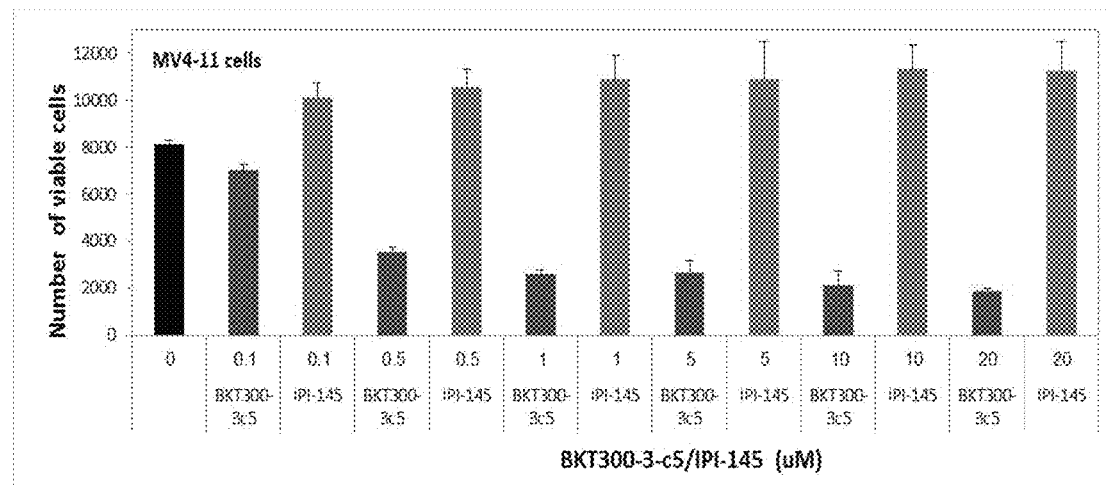
Figure 21B:
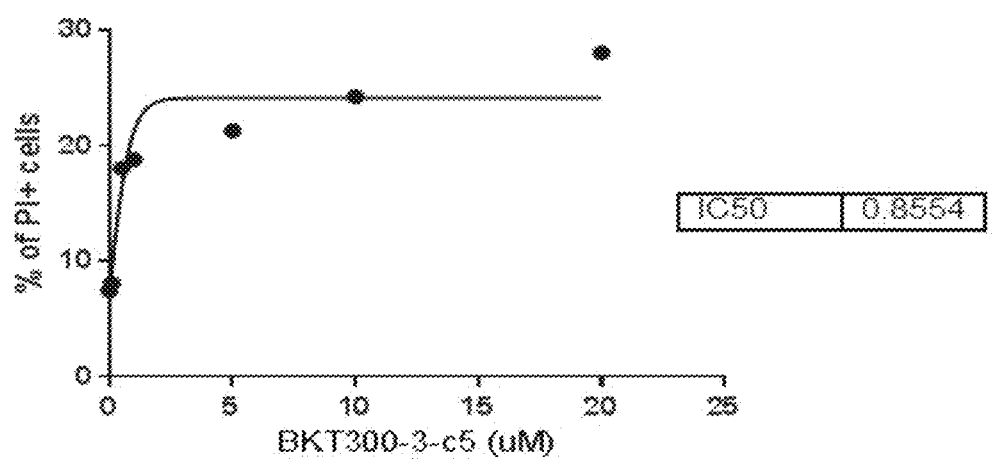

FIGS. 21A-B present a bar graph (FIG. 21A) showing the effect of 0.1, 0.5, 1, 5, 10 and 20 µM of Compound BKT300-3-c5 and of IPI-145 on the viability of MV4-11 cells, expressed by the number of viable cells, as determined by propidium iodide staining (FIG. 21A) and a plot showing the percentage of viable MV4-11 cells following 24-hour incubation with 0.1, 0.5, 1, 5, 10 and 20 µM of Compound BKT300-3-c5, as determined by propidium iodide staining (FIG. 21B).

Figure 22A:
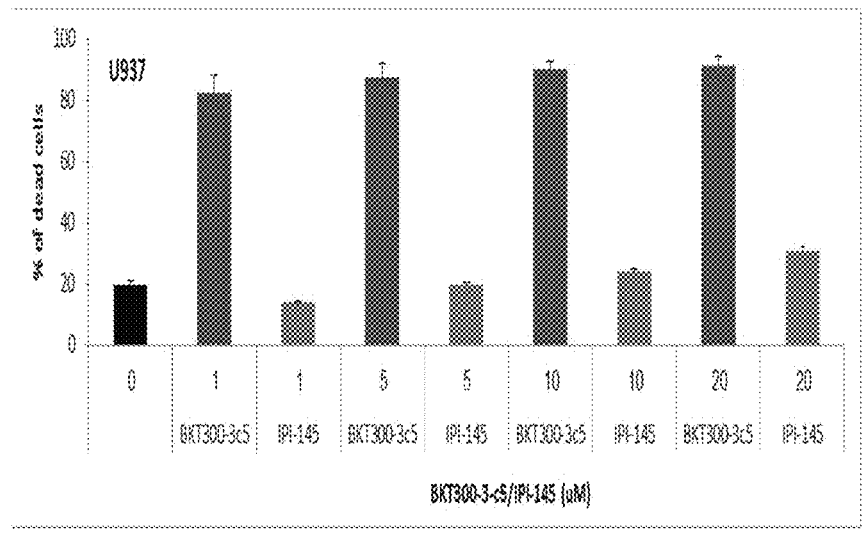
Figure 22B:
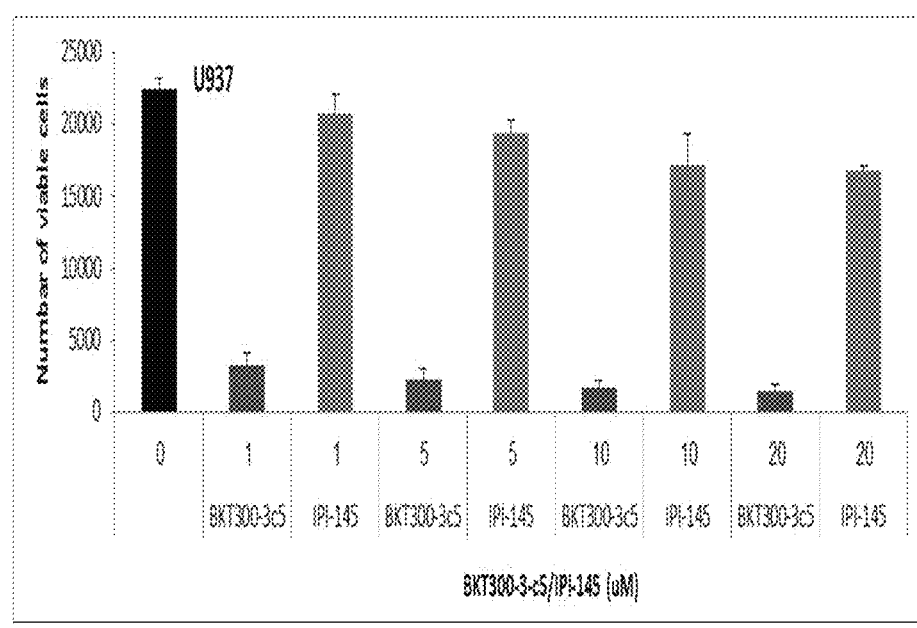

FIGS. 22A-B are bar graphs showing the effect of 1, 5, 10 and 20 µM of Compound BKT300-3-c5 and of IPI-145 on the viability of U937 cells, as expressed by percentage of dead cells (FIG. 22A) and the number of viable cells (FIG. 22B), as determined by propidium iodide staining.

Figure 23A:
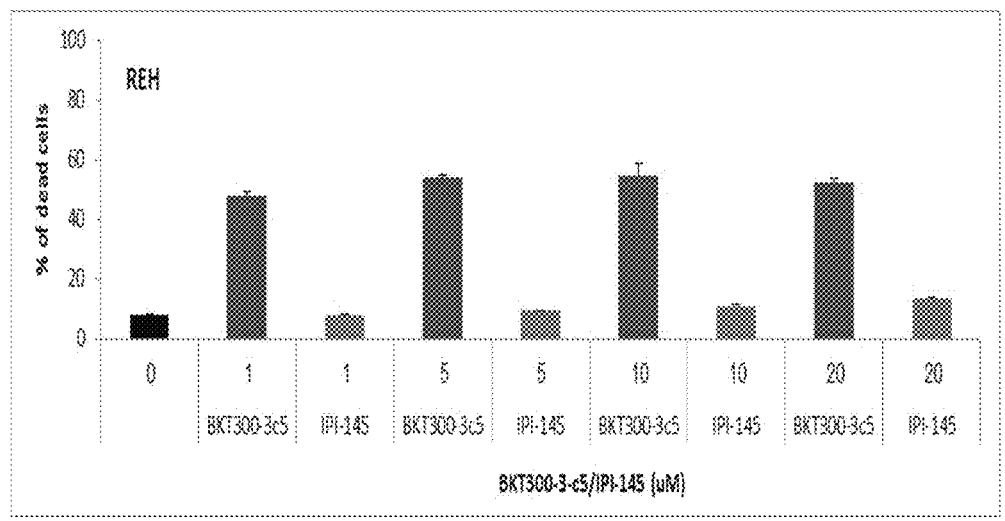
Figure 23B:
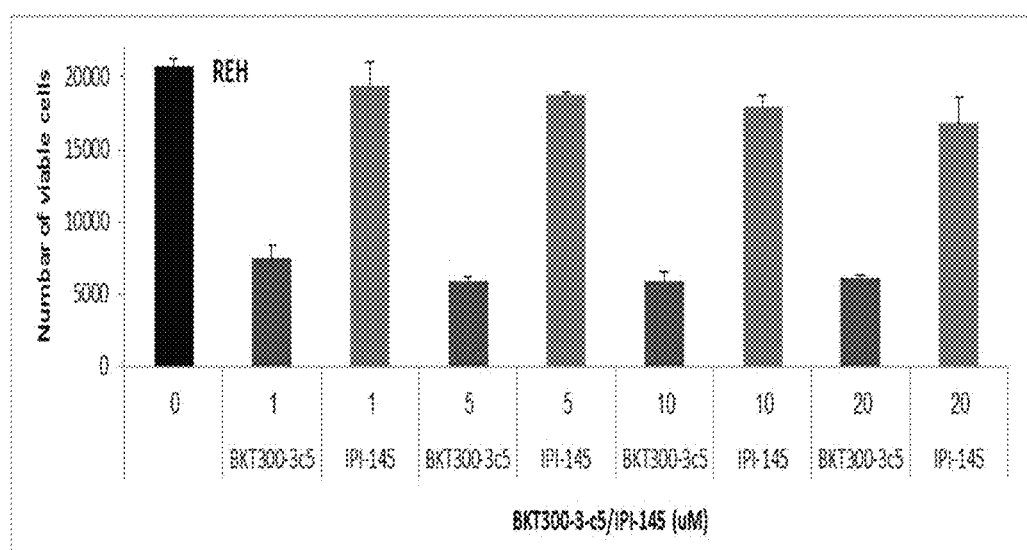

FIGS. 23A-B are bar graphs showing the effect of 1, 5, 10 and 20 µM of Compound BKT300-3-c5 and of IPI-145 on the viability of REH cells, as expressed by percentage of dead cells (FIG. 23A) and the number of viable cells (FIG. 23B), as determined by propidium iodide staining.

Figure 24A:
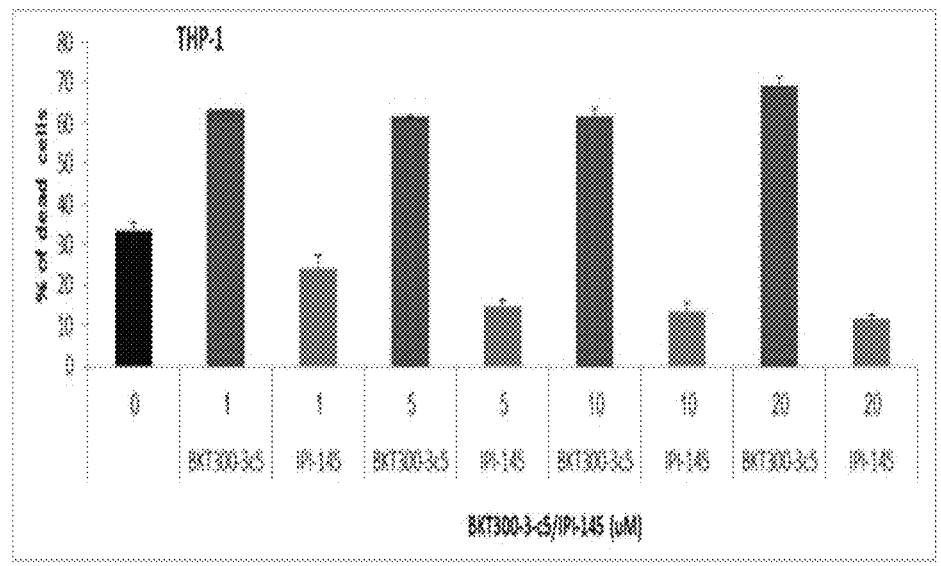
Figure 24B:
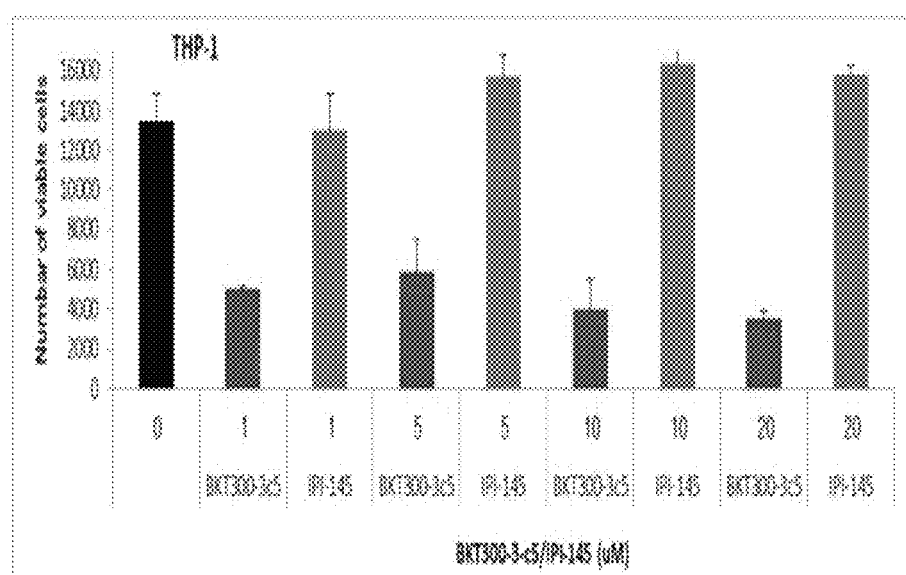

FIGS. 24A-B are bar graphs showing the effect of 1, 5, 10 and 20 µM of Compound BKT300-3-c5 and of IPI-145 on the viability of THP-1 cells, as expressed by percentage of dead cells (FIG. 24A) and the number of viable cells (FIG. 24B), as determined by propidium iodide staining.

Figure 25A:
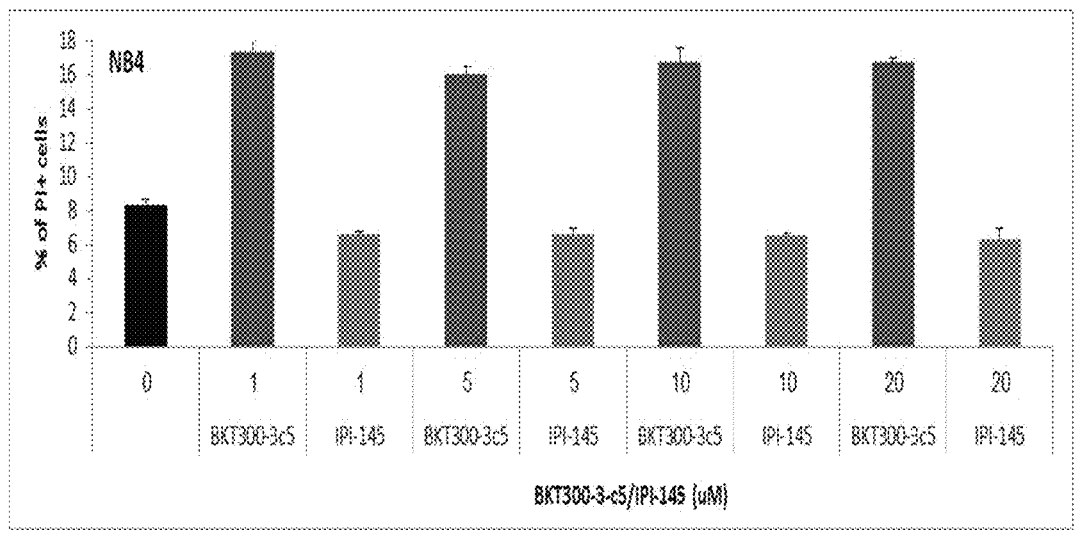
Figure 25B:
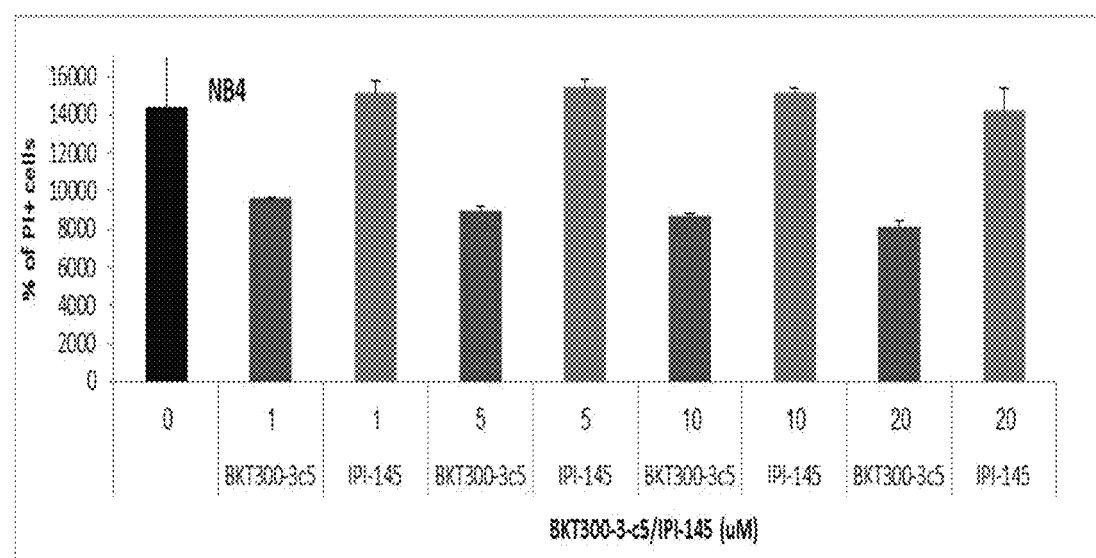

FIGS. 25A-B are bar graphs showing the effect of 1, 5, 10 and 20 µM of Compound BKT300-3-c5 and of IPI-145 on the viability of NB4 cells, as expressed by percentage of dead cells (FIG. 25A) and the number of viable cells (FIG. 25B), as determined by propidium iodide staining.

Figure 26:
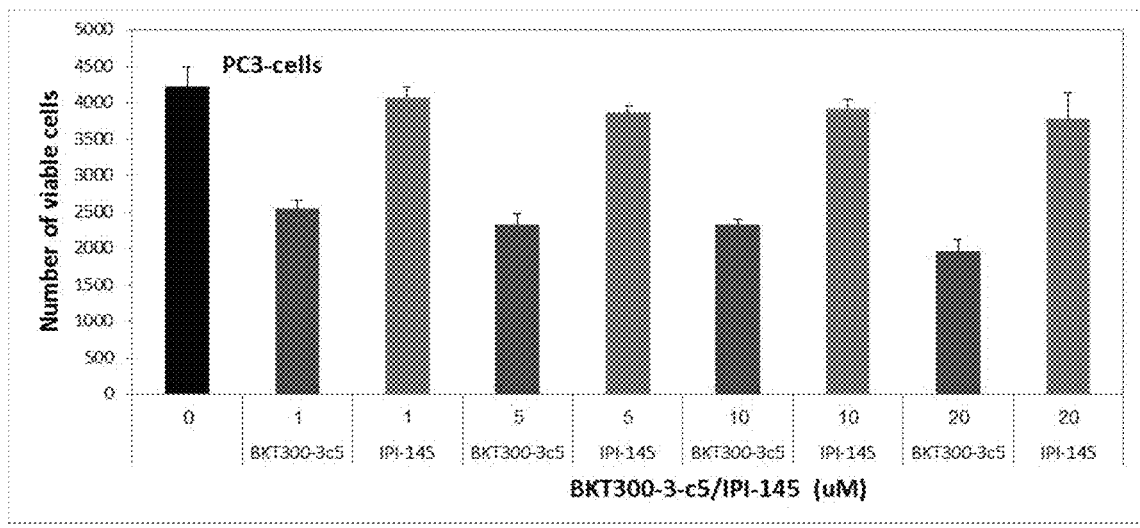

FIG. 26 is a bar graph showing the effect of 1, 5, 10 and 20 µM of Compound BKT300-3-c5 and of IPI-145 on the viability of PC-3 cells, expressed by the number of viable cells, as determined by propidium iodide staining.

Figure 27:
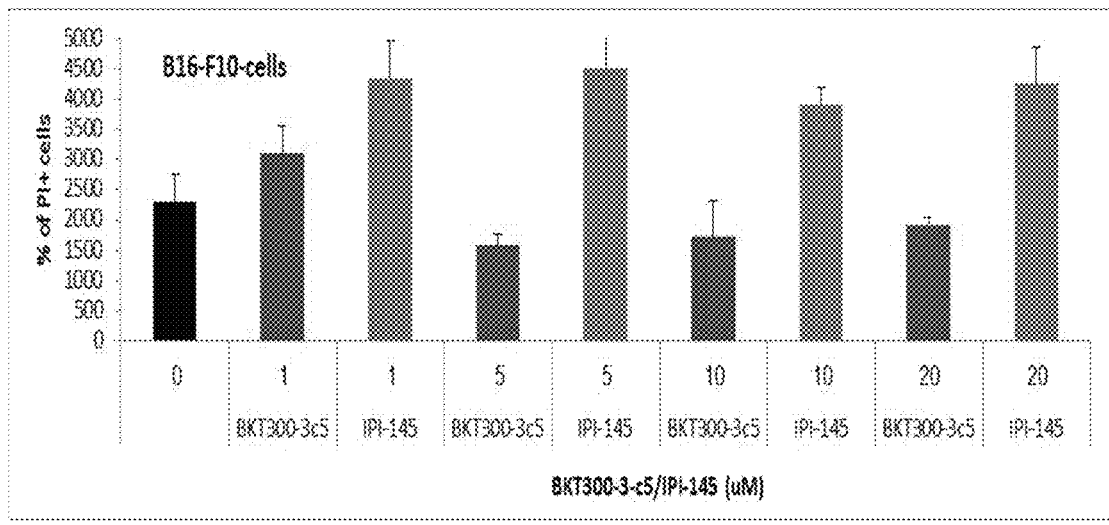

FIG. 27 is a bar graph showing the effect of 1, 5, 10 and 20 µM of Compound BKT300-3-c5 and of IPI-145 on the viability of B16-F10 cells, expressed by the number of viable cells, as determined by propidium iodide staining.

Figure 28A:
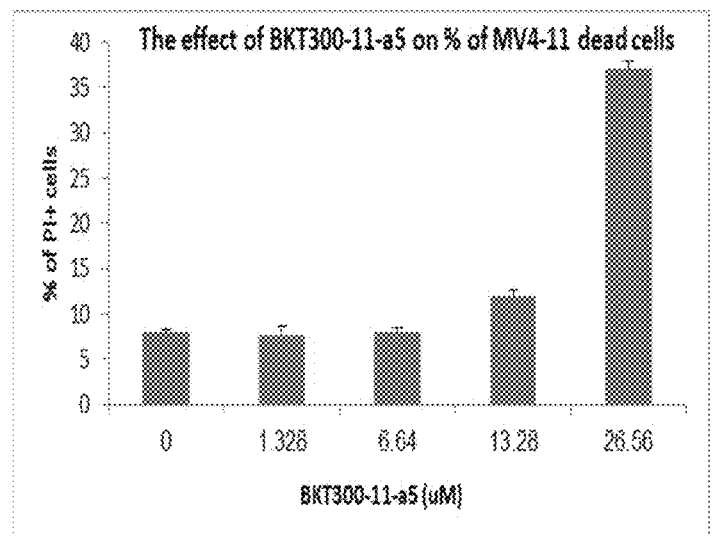
Figure 28B:
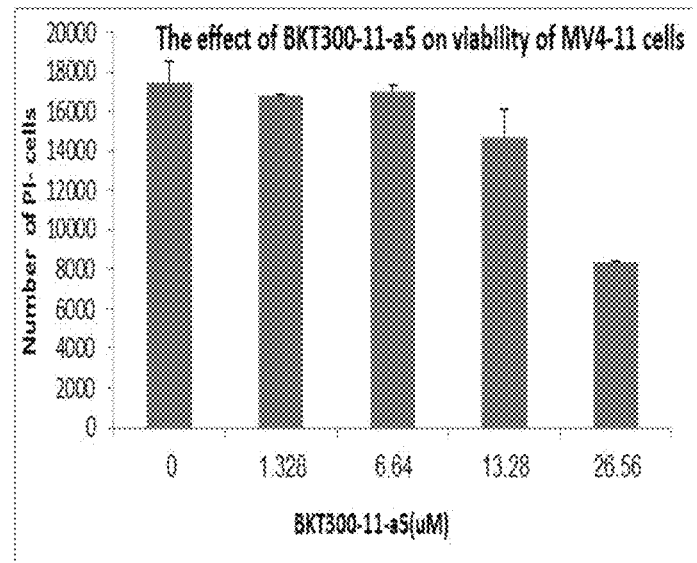

FIGS. 28A-B are bar graphs showing the effect of 0, 1.328, 6.64, 13.28 and 26.56 µM of Compound BKT300-11-a5 on the viability of MV4-11 cells, as expressed by percentage of dead cells (FIG. 28A) and the number of viable cells (FIG. 28B), as determined by propidium iodide staining.

FIG. 29 presents data obtained upon 7-ADD staining of various cell lines following 24-hour incubation with BKT300-3-c5 (1 µM). Upper right graph shows comparative data for cells incubated with IPI-145 (1 µM).

FIG. 30 presents data obtained following 24-hour incubation of MV4-11 cells with and without BKT300-3-c5 (1 µM), upon staining with PI and AnnexinV.

Figure 31A:
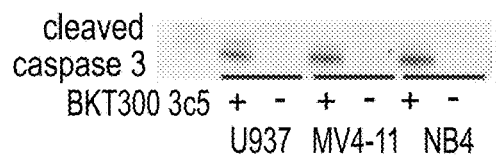
Figure 31B:
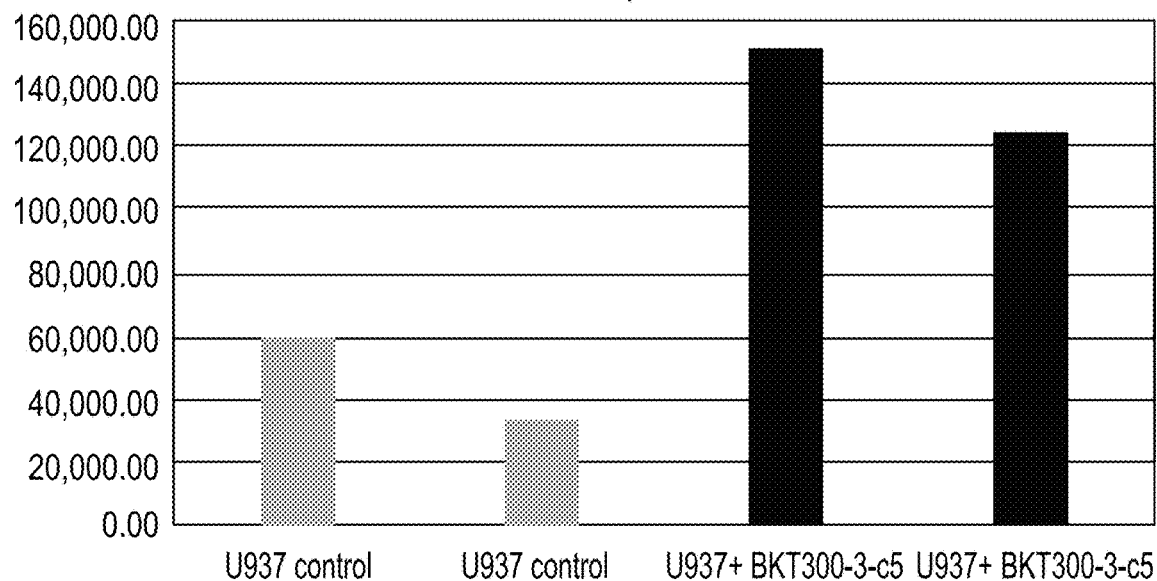
Figure 31C:
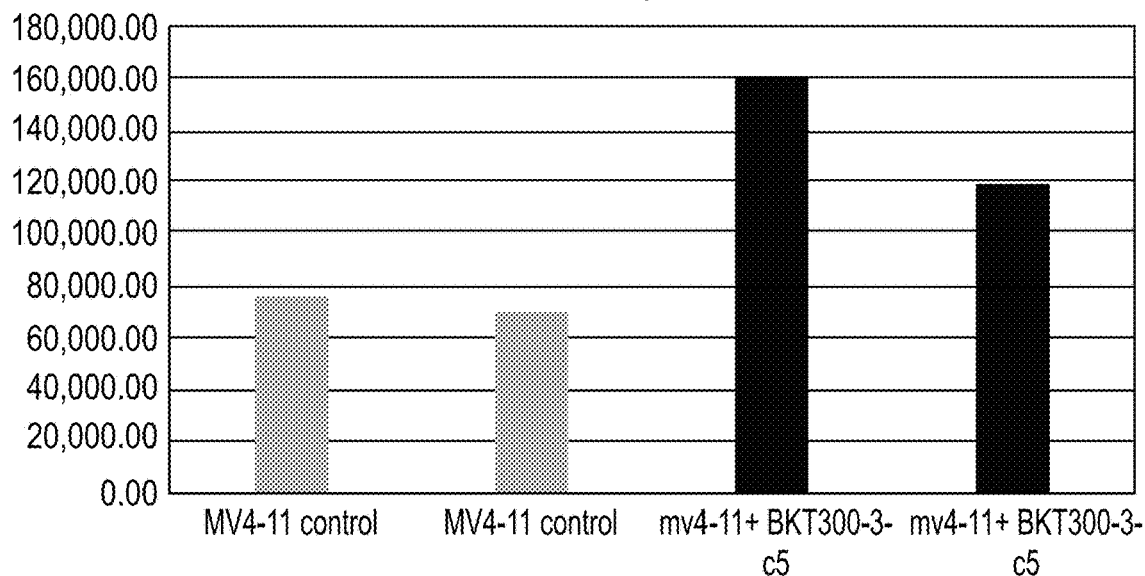

FIGS. 31A-C present a Western blot showing the effect of 24-hours incubation of BKT300-3-c5 (1 µM) on the presence of cleaved caspase-3 in U937, MV4-11 and NB4 cells (FIG. 31A) and bar graphs showing the effect of 24-hours incubation of BKT300-3-c5 (1 µM) on the presence of cleaved caspase-3 in U937 cells (FIG. 31B) and MV4-11 cells (FIG. 31C), as determined by ELISA assay and expressed by Optical Density (OD).

Figure 32A:
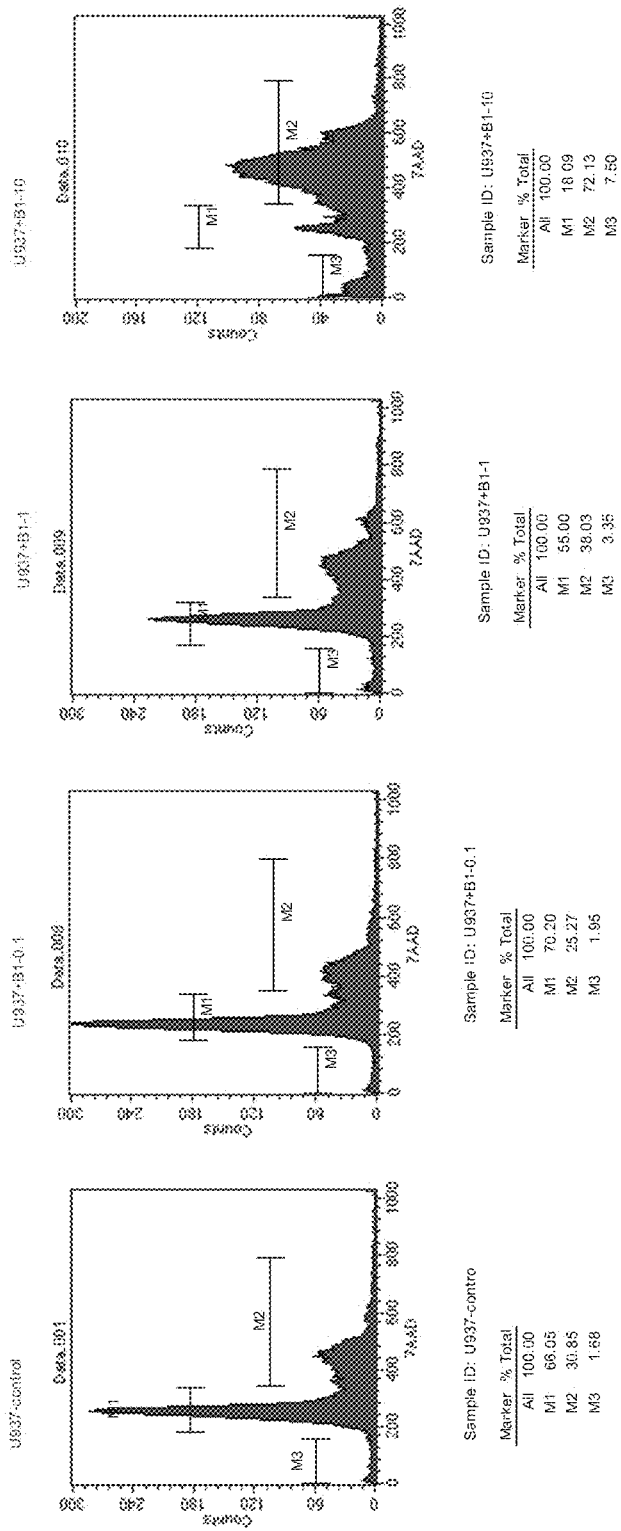
Figure 32B:
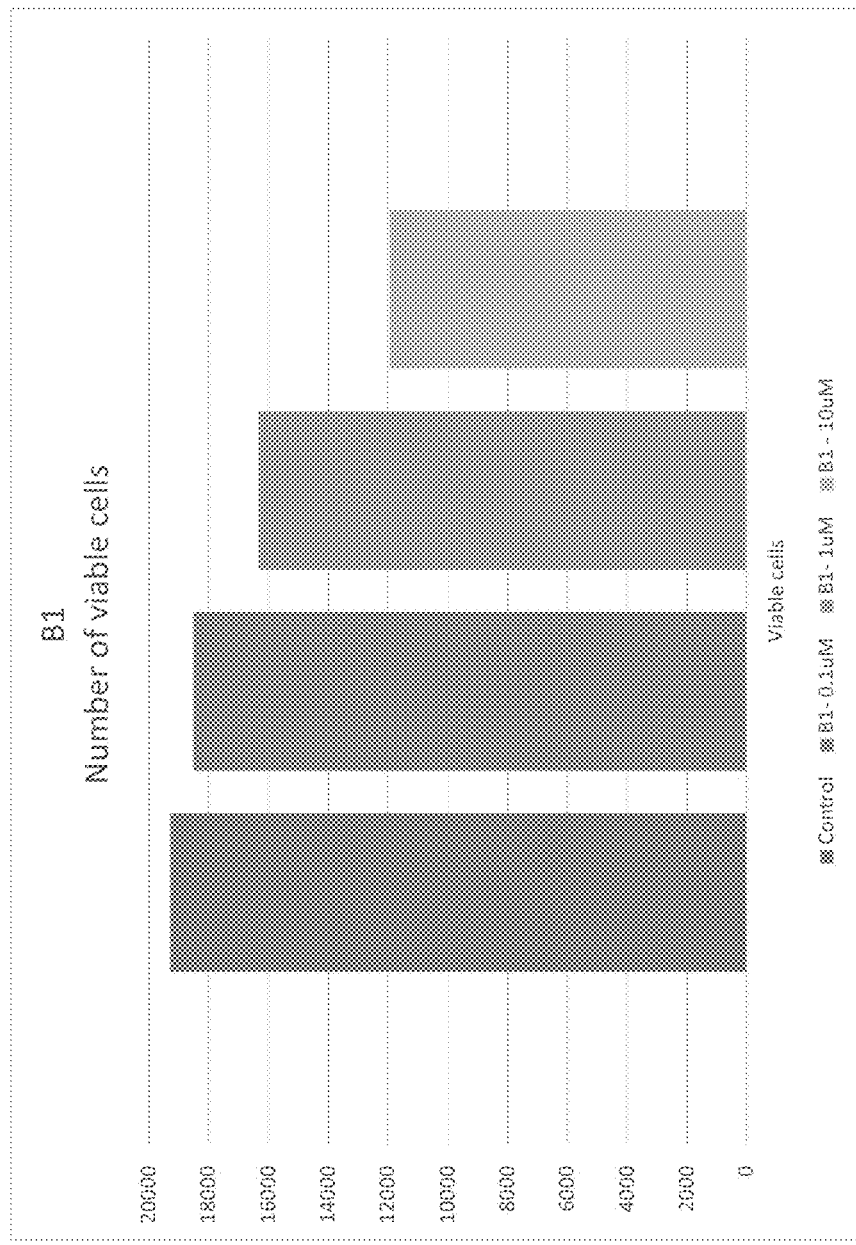
Figure 32C:
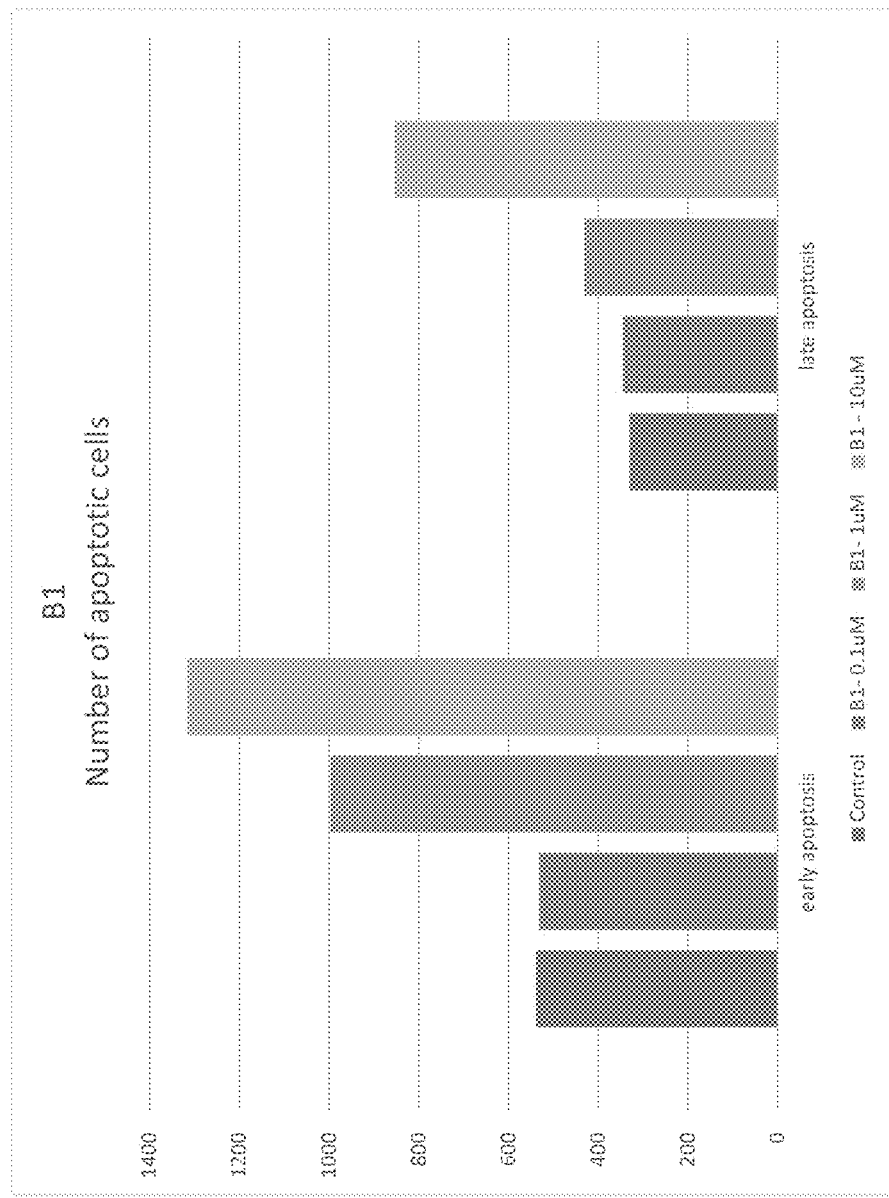

FIGS. 32A-C present data obtained following incubation of U937 cells with Compound B1, at a concentration of 0, 0.1, 1 and 10 µM, for 24 hours, upon 7-ADD staining of the cells (FIG. 32A), and upon staining of the cells with PI and Annexin V (FIG. 32B, showing number of viable cells; and FIG. 32C showing number of apoptotic cells).

Figure 33A:
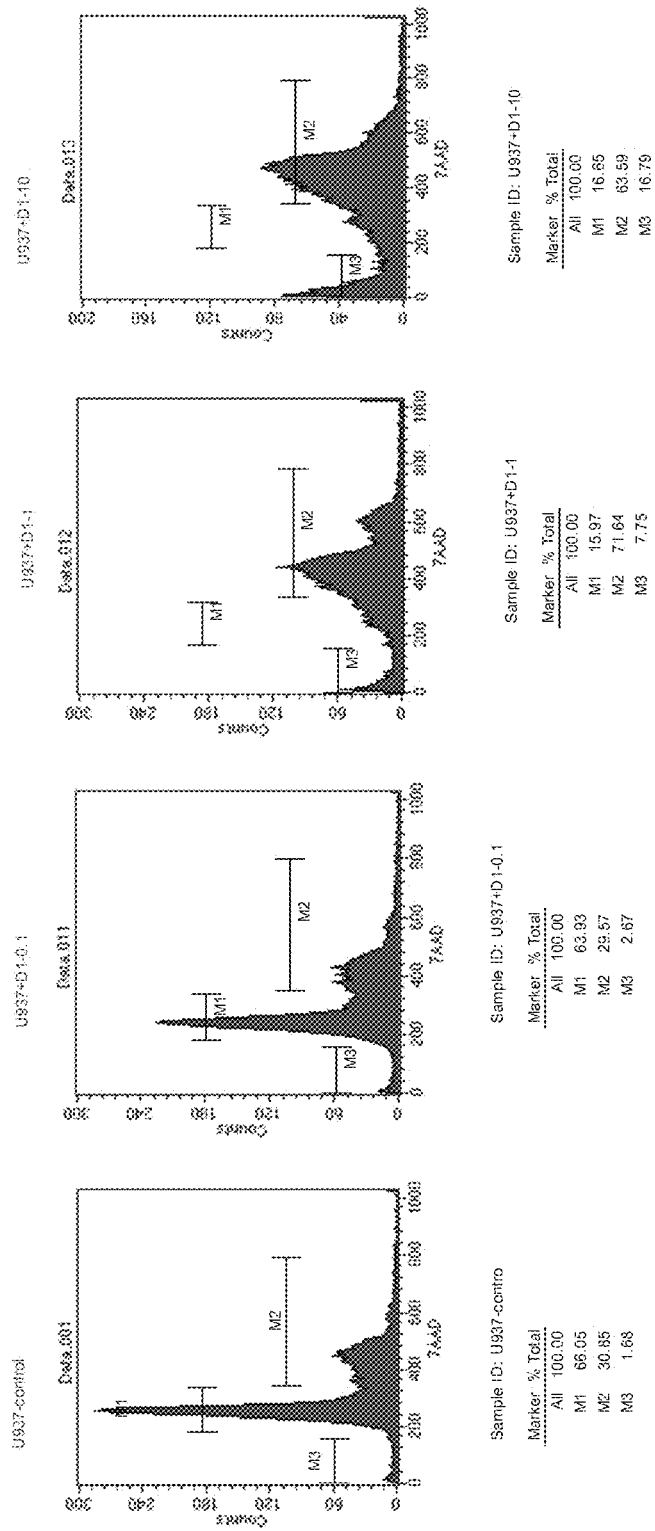
Figure 33B:
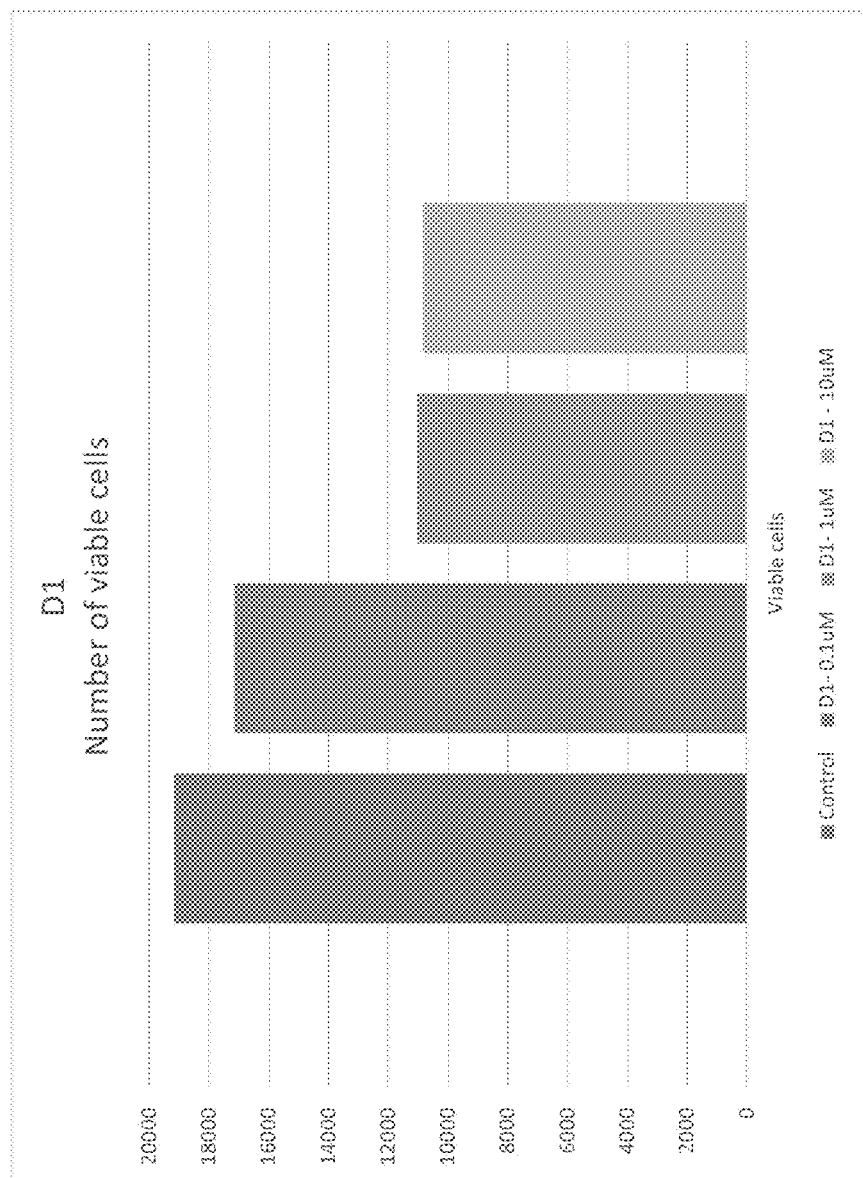
Figure 33C:
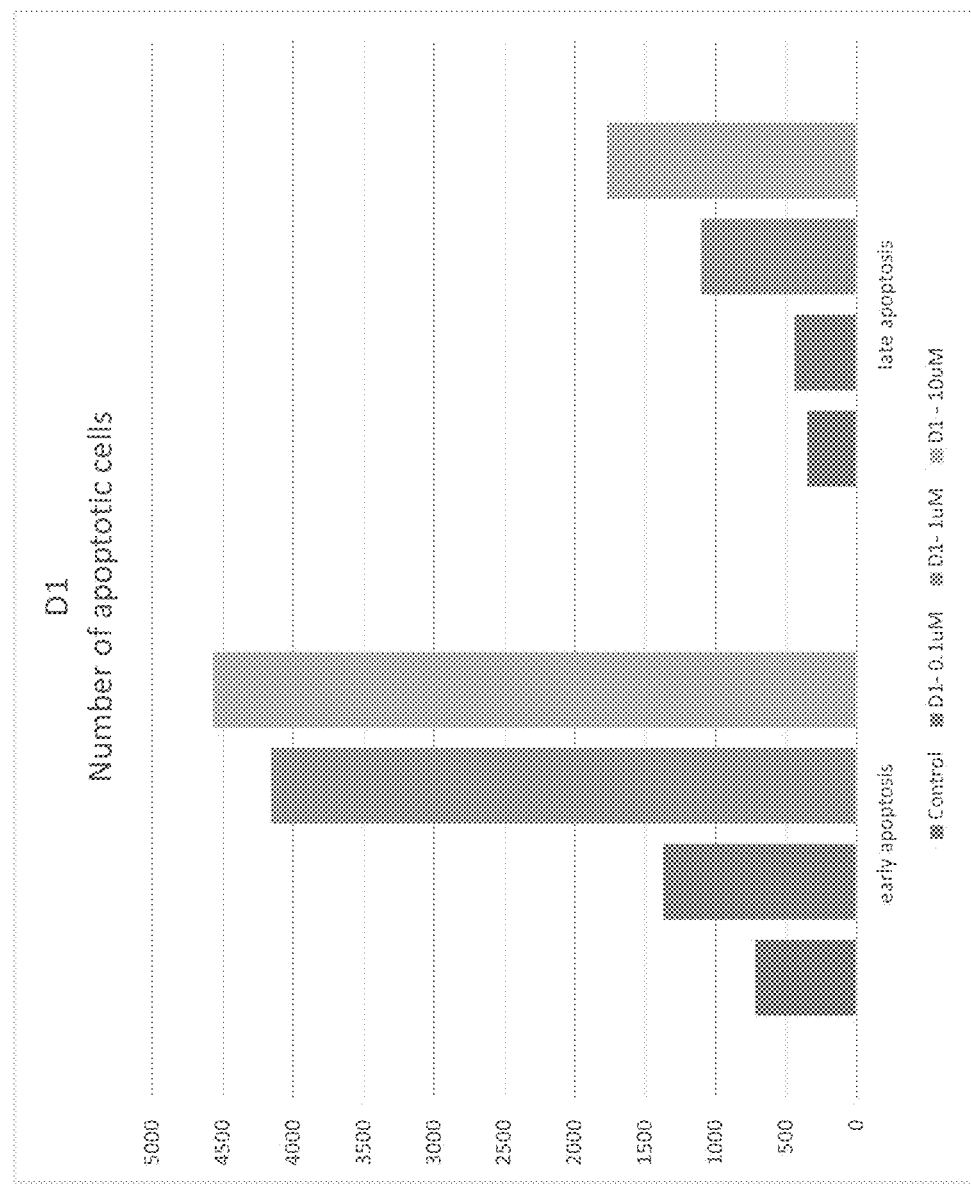

FIGS. 33A-C present data obtained following incubation of U937 cells with Compound D1, at a concentration of 0, 0.1, 1 and 10 µM, for 24 hours, upon 7-ADD staining of the cells (FIG. 33A), and upon staining of the cells with PI and Annexin V (FIG. 33B, showing number of viable cells; and FIG. 33C showing number of apoptotic cells).

Figure 34A:
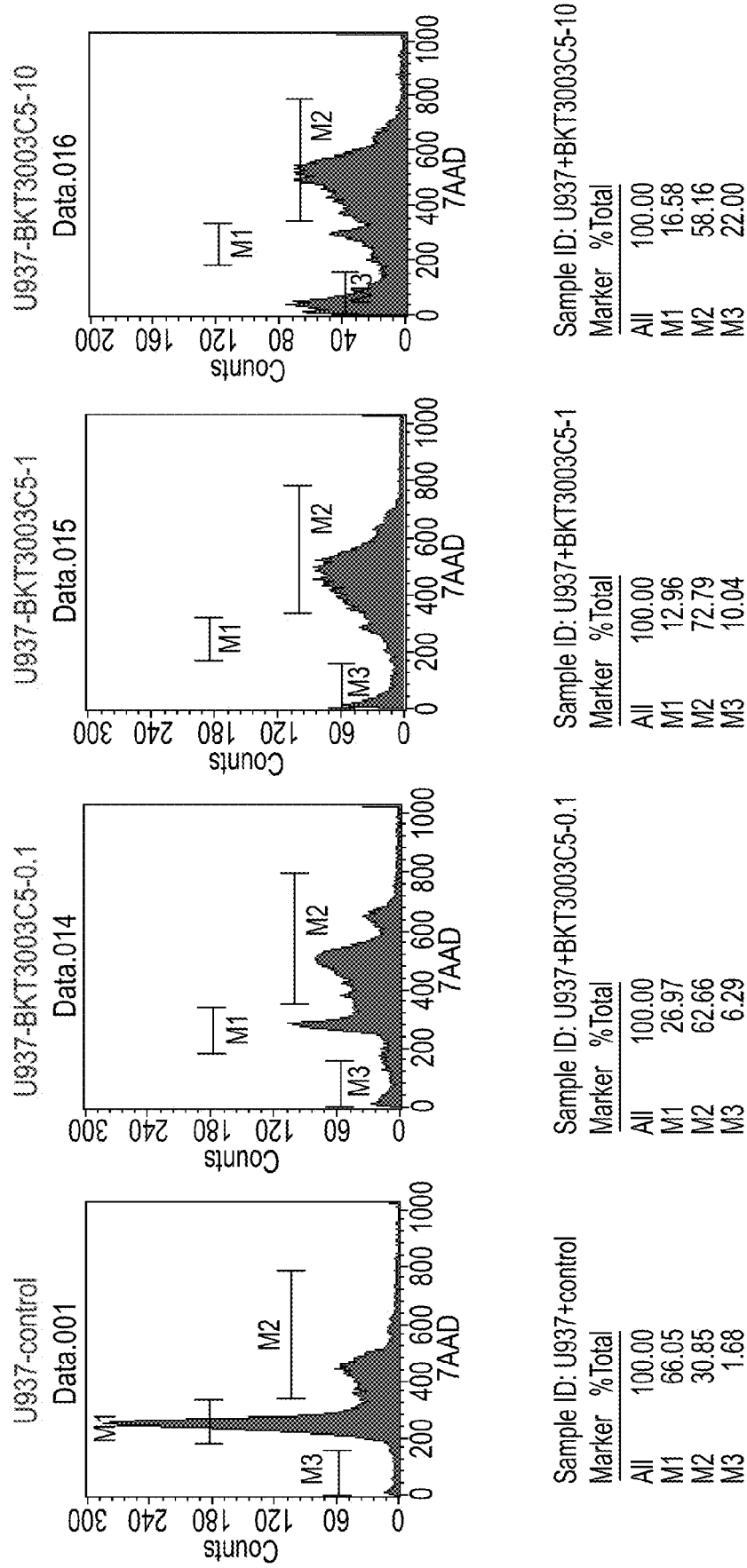
Figure 34B:
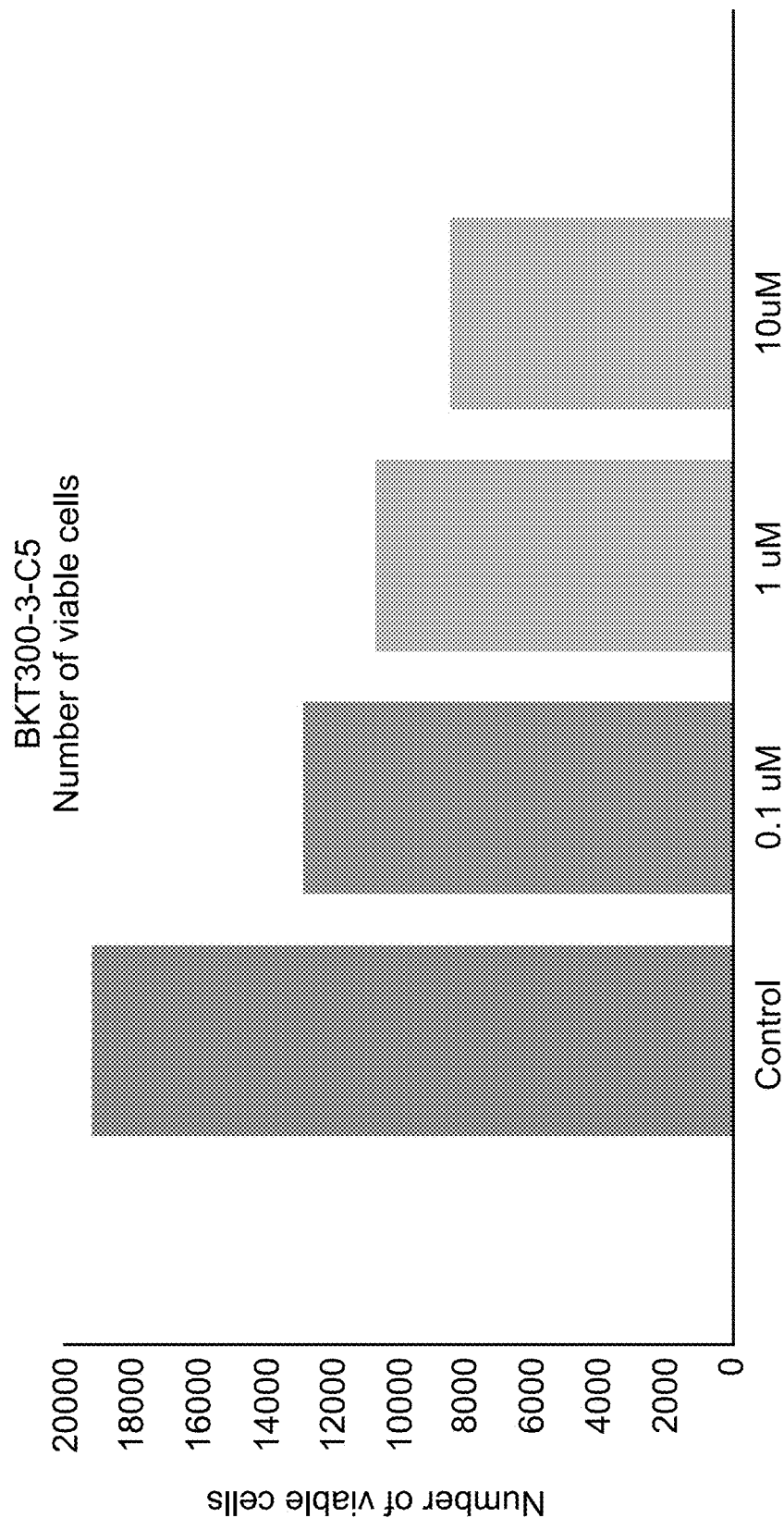
Figure 34C:
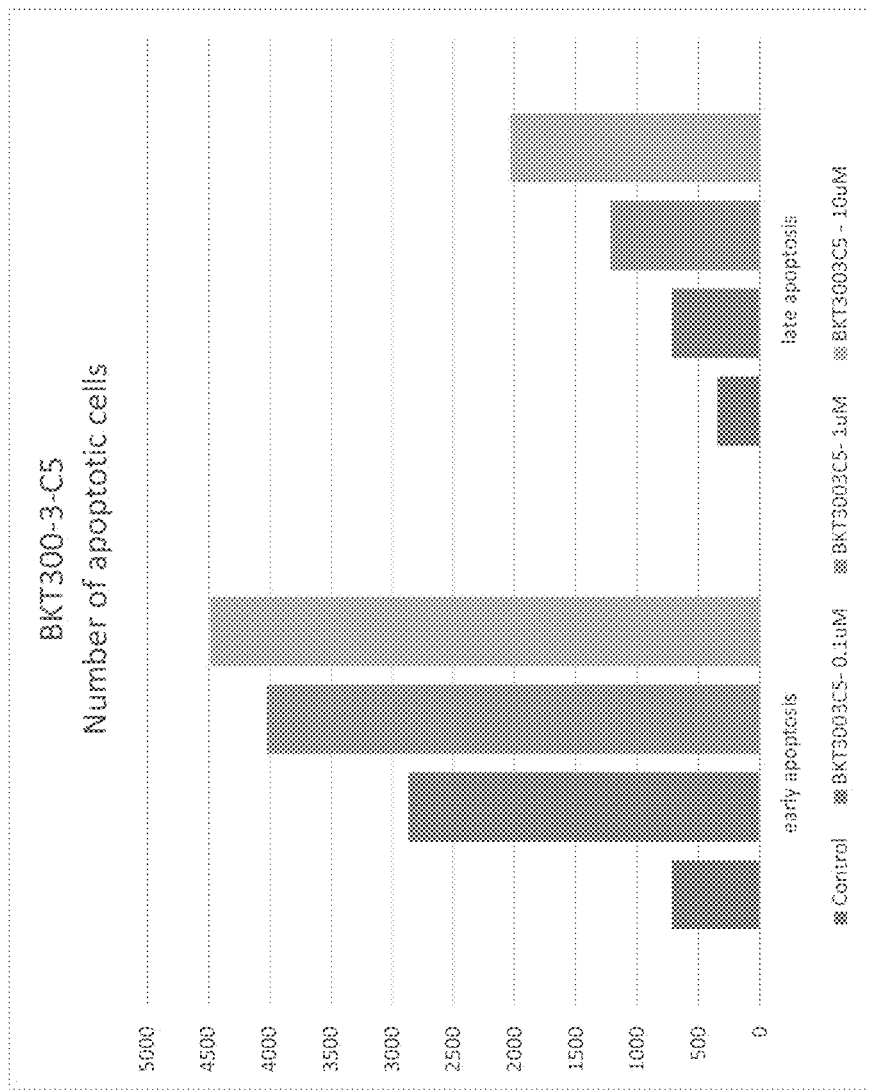

FIGS. 34A-C present data obtained following incubation of U937 cells with Compound BKT300-3-c5, at a concentration of 0, 0.1, 1 and 10 µM, for 24 hours, upon 7-ADD staining of the cells (FIG. 34A), and upon staining of the cells with PI and Annexin V (FIG. 34B, showing number of viable cells; and FIG. 34C showing number of apoptotic cells).

Figure 35A:
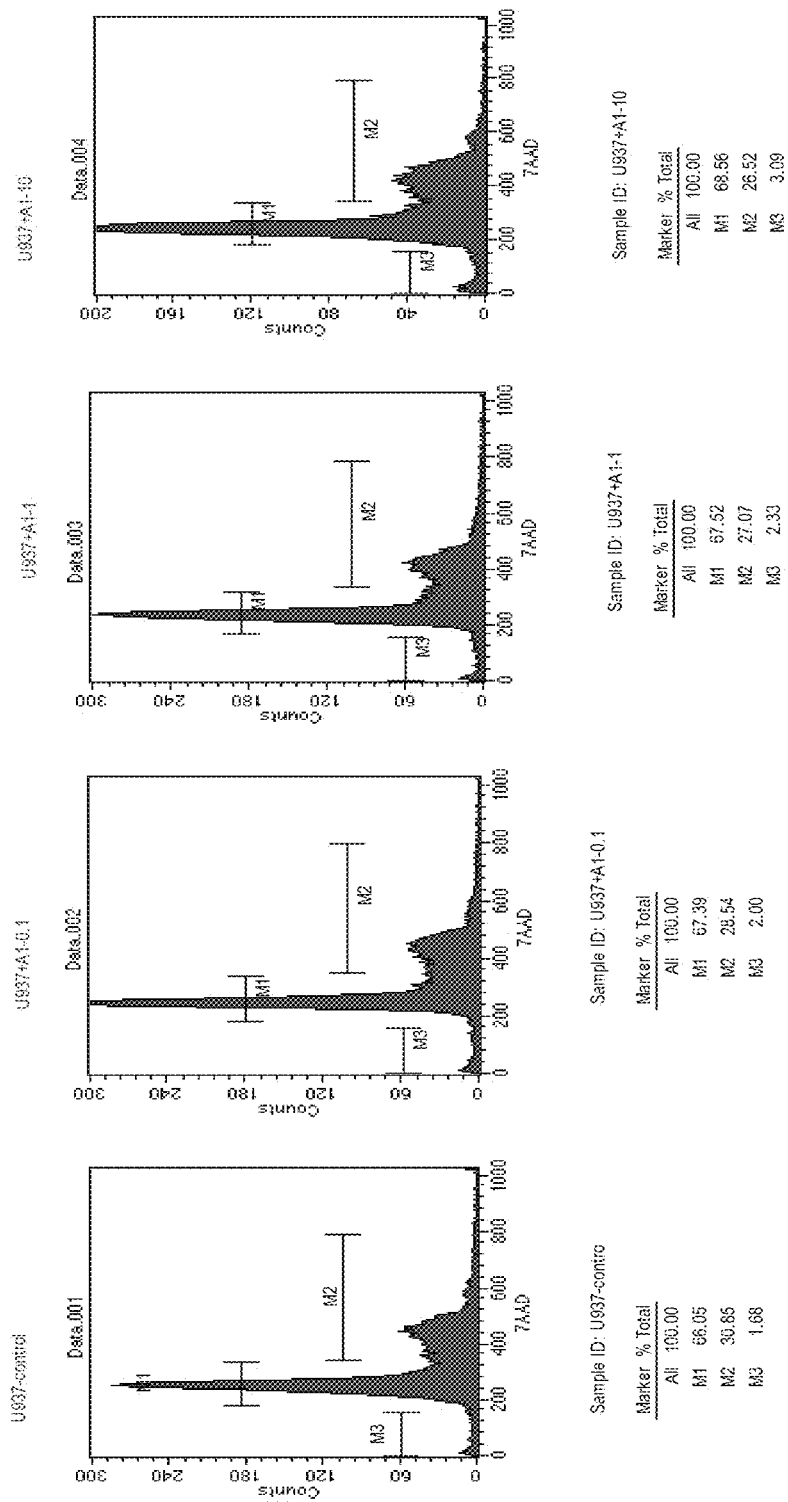
Figure 35B:
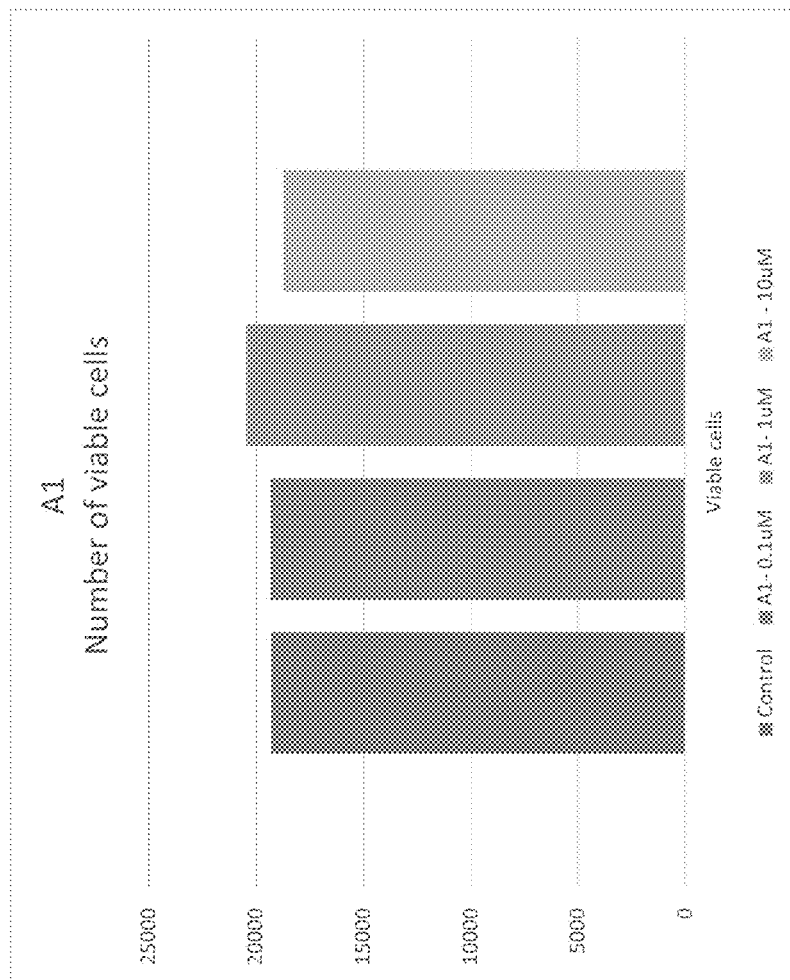
Figure 35C:
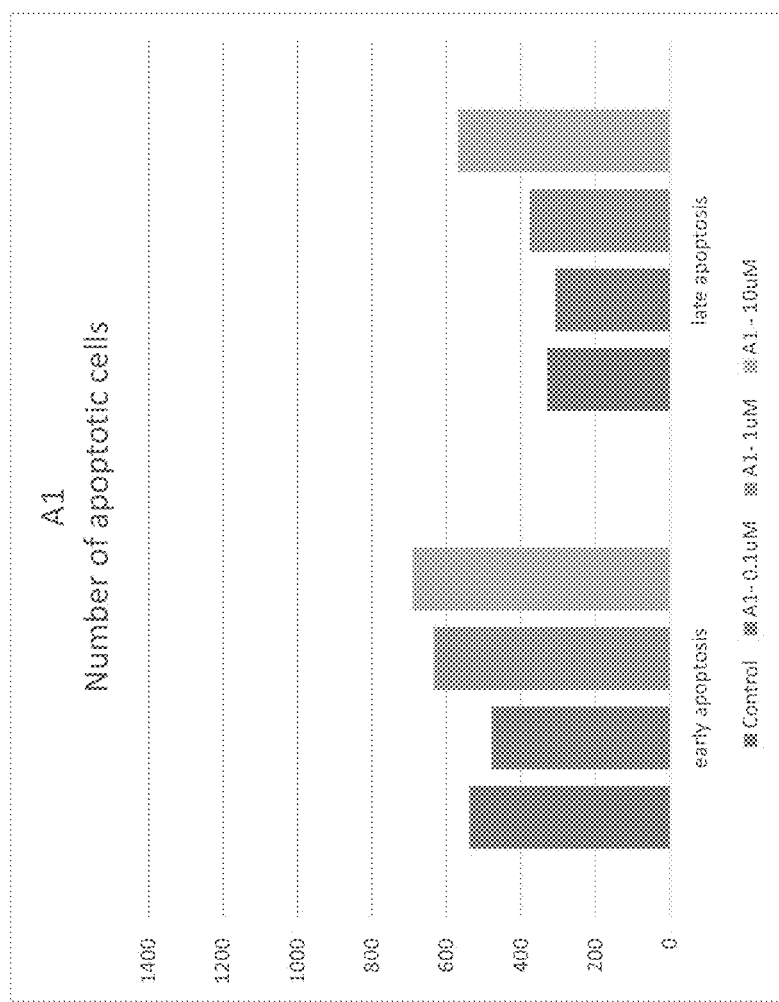

FIGS. 35A-C present data obtained following incubation of U937 cells with Compound A1, at a concentration of 0, 0.1, 1 and 10 µM, for 24 hours, upon 7-ADD staining of the cells (FIG. 35A), and upon staining of the cells with PI and Annexin V (FIG. 35B, showing number of viable cells; and FIG. 35C showing number of apoptotic cells).

Figure 36A:
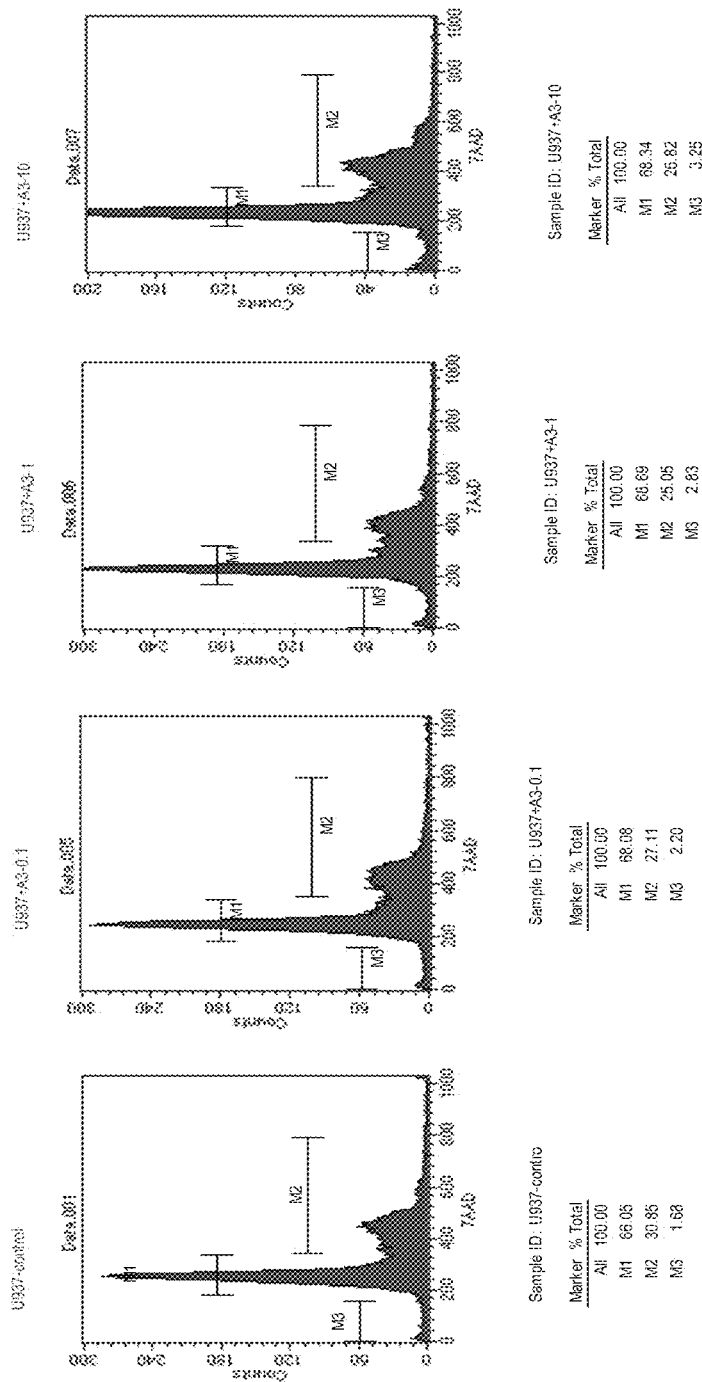
Figure 36B:
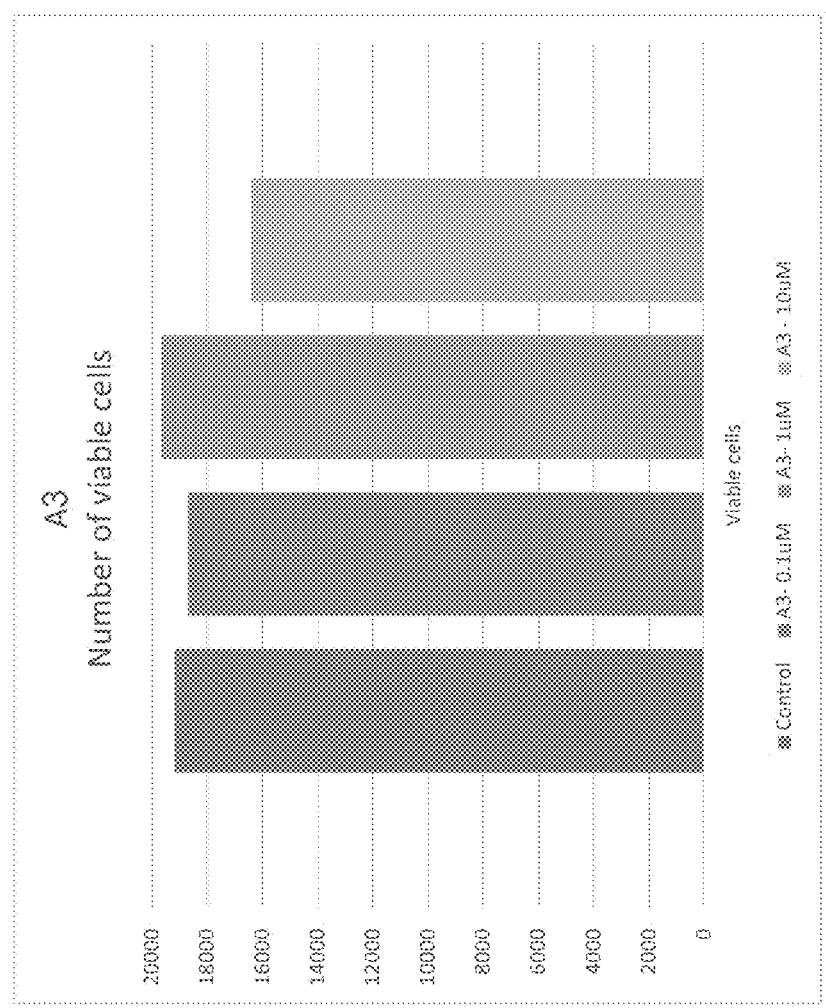
Figure 36C:
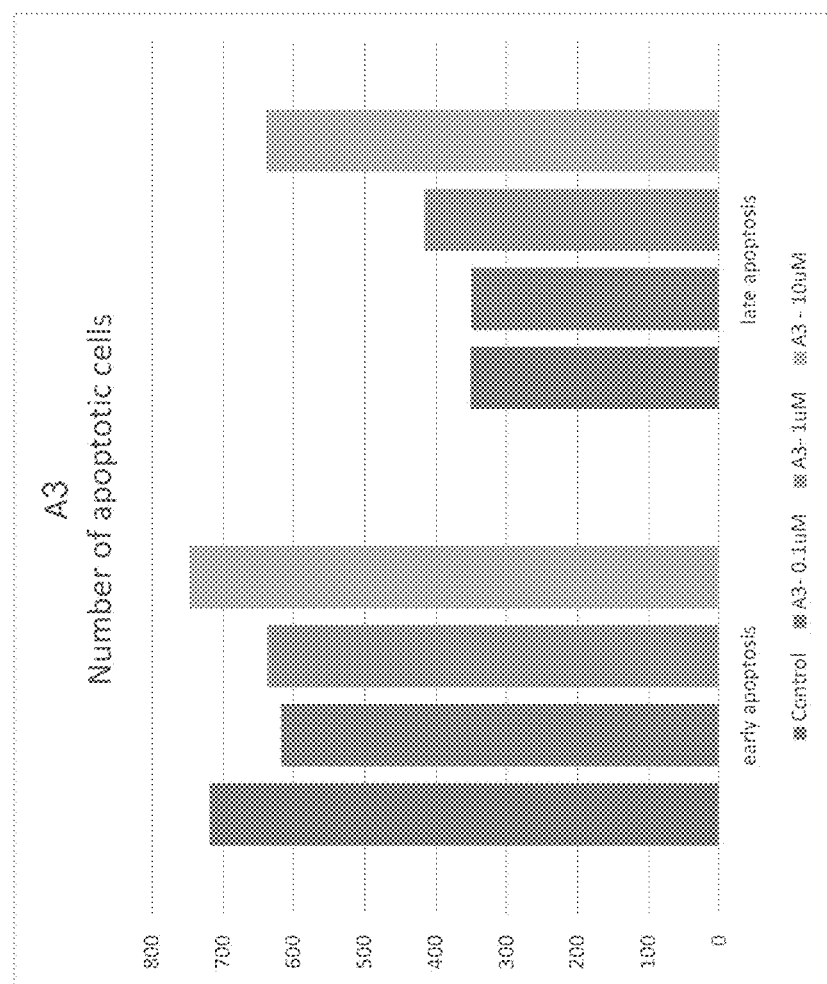

FIGS. 36A-C present data obtained following incubation of U937 cells with Compound A3, at a concentration of 0, 0.1, 1 and 10 µM, for 24 hours, upon 7-ADD staining of the cells (FIG. 36A), and upon staining of the cells with PI and Annexin V (FIG. 36B, showing number of viable cells; and FIG. 36C showing number of apoptotic cells).

Figure 37A:
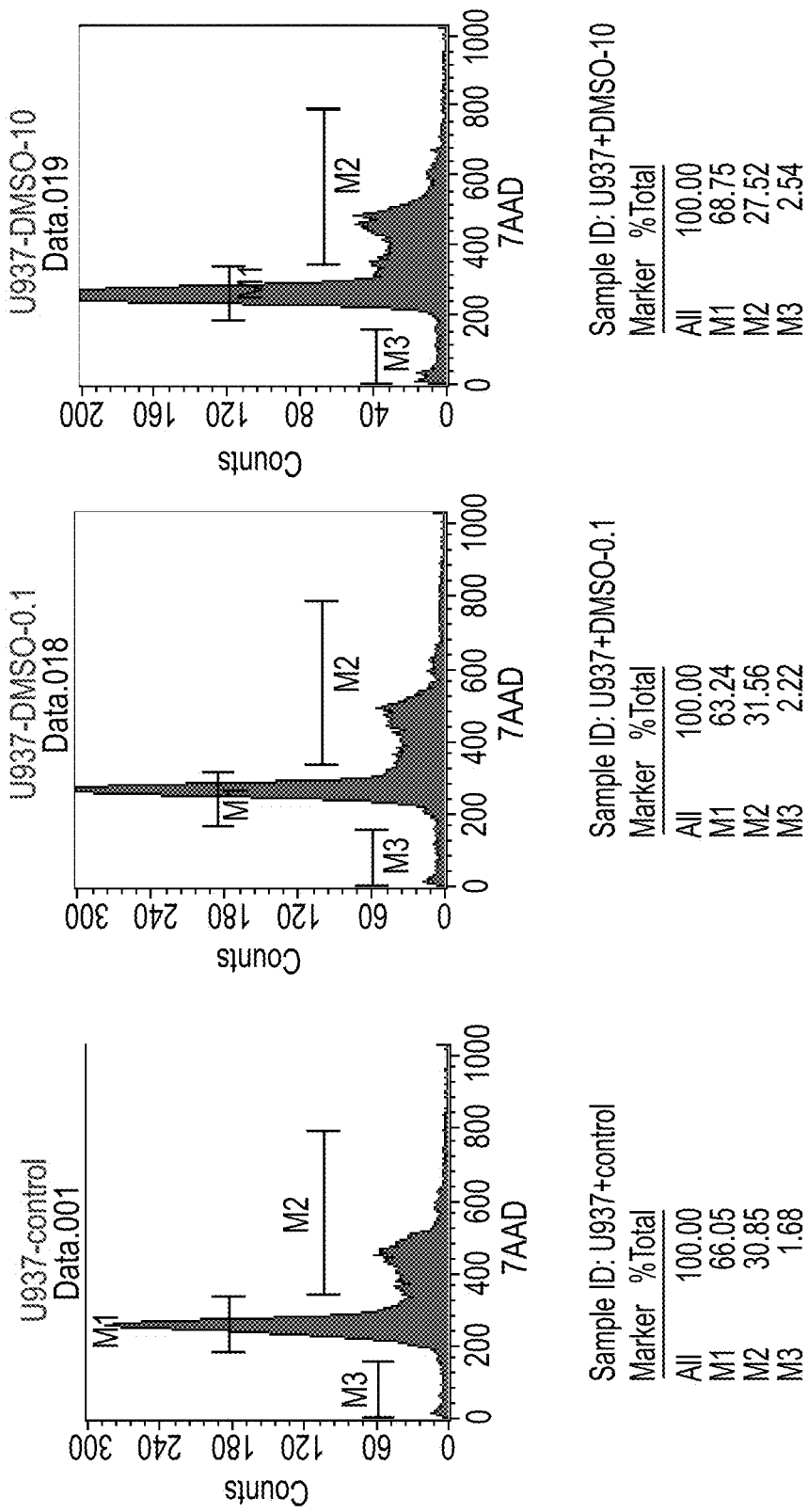
Figure 37B:
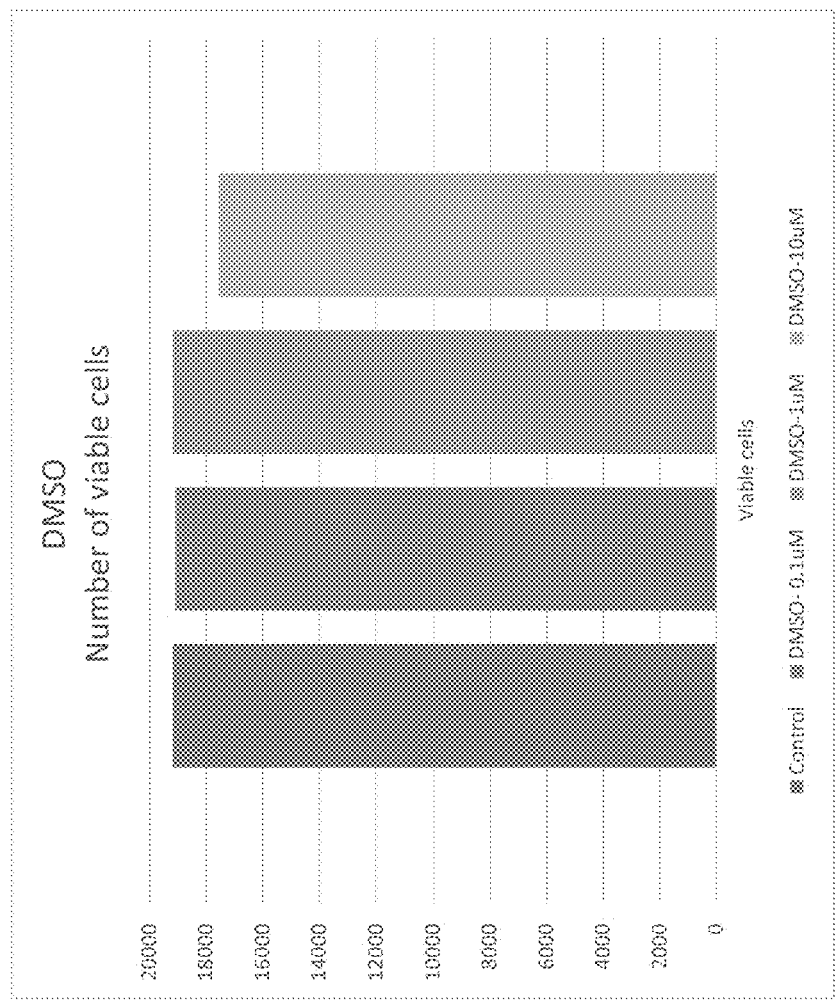
Figure 37C:
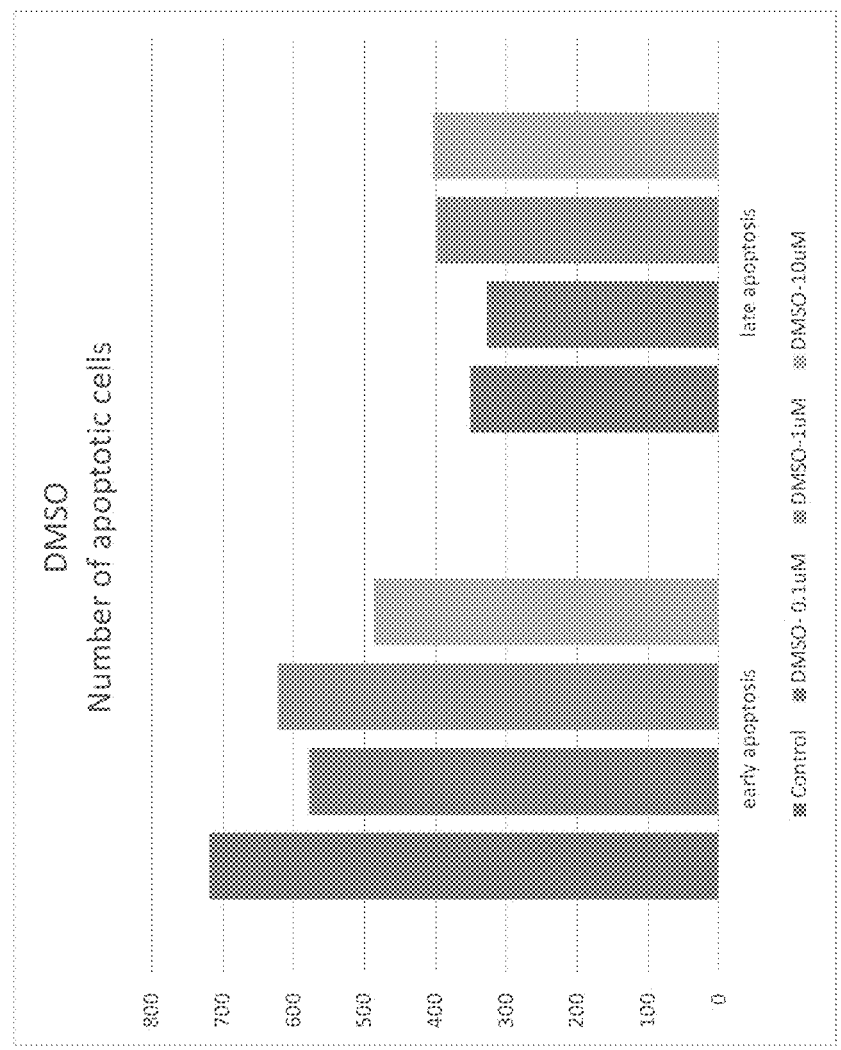

FIGS. 37A-C present data obtained following incubation of U937 cells with DMSO, at a concentration of 0, 0.1, 1 and 10 µM, for 24 hours, upon 7-ADD staining of the cells (FIG. 37A), and upon staining of the cells with PI and Annexin V (FIG. 37B, showing number of viable cells; and FIG. 37C showing number of apoptotic cells).

DESCRIPTION OF SPECIFIC EMBODIMENTS OF THE INVENTION

The present invention, in some embodiments thereof, relates to therapy and more particularly, but not exclusively, to compounds which are useful in modulating a biological activity of a chemokine, in killing cancel cells, in inhibiting a kinase, in inhibiting chemokine-dependent cell migration and/or in treating diseases and disorders associated with biological activities of chemokines and/or cell migration and/or kinase activity, such as cancer and inflammatory diseases and disorders, and to methods utilizing these compounds.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for compounds suitable for modulating chemokine activity, and treating conditions associated with the biological activity of chemokines, the present inventors have screened a library of about 3,500 natural compounds for chemokine-binding activity, and then further screened the chemokine-binding molecules for an ability to modulate the effect of individual chemokines on cells, as well as for an ability to affect cancer cells (e.g., by killing cancer cells, inhibiting growth of cancer cells and/or inhibiting chemokine-dependent migration of cancer cells) and/or kill pathogenic cells such as cancer cells.

Using this laborious screening process, the present inventors have identified the compound referred to herein as BKT300 (see, the Examples section that follows) as a promising modulator of chemokine activity, a selective inhibitor of SDF-1/CXCR4 activity and/or as an enhancer of cancer cell death. Reference is made to FIGS. 1, 2A, 2B and 3, which show inhibition of cell migration towards the chemokine MIP3a, SDF-1, or towards the chemokine MCP-1, by BKT300; and to FIGS. 4A-12C which demonstrate that the small molecule BKT300 induces cell death in cancer cells, and reduces cancer cell numbers in an in vivo mouse model.

The small molecule BKT300 was also screened for its effect on a selected list of human kinases and was shown to inhibit activity of certain kinases (see, Table 2, Example 4, in the Examples section that follows).

Encouraged by the pronounced activity of BKT300, the present inventors have studied the interactions of BKT300 with the binding site of kinases, using computational modeling (see, for example, FIGS. 14-16), and based on the data retrieved in these computational study, have designed small molecules that are structural analogs of BKT300, which maintain at least some of the structural features of BKT300 which were considered as attributing to its activity (see, for non-limiting examples, FIGS. 17 and 18).

The present inventors have shown that exemplary such structural analogs of BKT300 act by modulating a biological activity of chemokines and as anti-cancer agents by inducing cancer cells death and/or effecting cancel cells migration. Reference is made, for example, to FIGS. 19A-37C.

The structural analogs described herein are useful in modulating a biological activity of chemokines, and accordingly in treating diseases or disorders associated with a biological activity of a chemokine. The structural analogs described herein are particularly useful as anti-cancer agents, by inducing cancer cells death and/or effecting cancer cells migration (by inhibiting angiogenesis and/or metastasis), as described in further detail hereinbelow. The structural analogs described herein are further useful in inhibiting an activity of a kinase, for example, MELK, MAPK4K and IP3K, and in treating diseases or disorders in which inhibition of a kinase is beneficial, such as cancer and inflammation.

The general effect of compounds of some embodiments of the invention is shown on various biological phenotypes including chemokine-induced cell migration and apoptosis. These findings place the compounds described herein as pharmaceuticals, which can be used in the treatment of various medical conditions including inflammation (e.g., autoimmune diseases), cancer and non-cancerous hyperproliferative diseases.

Embodiments of the present invention therefore generally relate to newly designed small molecules and to uses thereof.

The Compounds (Small Molecules):

According to an aspect of some embodiments of the present invention there are provided newly designed small molecules (compounds) which can be collectively represented by Formula Ia:

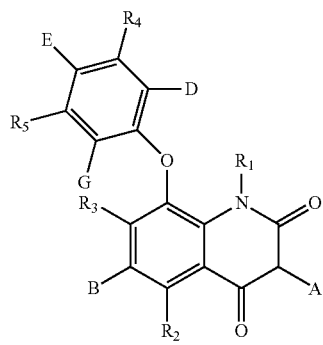

Formula Ia wherein:
A is an alkyl being at least 4 carbon atoms in length;
B is selected from hydroxyl, alkoxy and aryloxy, or from hydroxyl and alkoxy;
D, E and G are each independently selected from hydrogen, hydroxy, alkoxy, aryloxy and alkyl;
$R_1$ is selected from hydrogen, alkyl and cycloalkyl, or from hydrogen and alkyl; and
each of $R_2$-$R_5$ is independently selected from hydrogen, hydroxy, halo, alkoxy, thioalkoxy, thiol, thioalkoxy, amine, and optionally alkyne, aryloxy, thioaryloxy, carboxylate, carbonyl, sulfonyl, sulfonate, sulfinyl, cyano, nitro, and other substituents, as described herein.

Compound of Formula Ia feature a ketone group (carbonyl), and, can undergo a keto-enol tautomerization into the "enol" form, and thus be represented alternatively by Formula Ib:

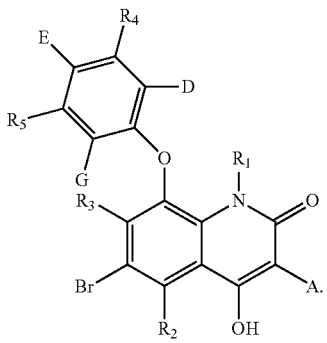

Formula Ib

Keto-enol tautomerization is known in the art as describing the rapid equilibrium between a carbonyl group (C═O) and its enol tautomer.

The keto-enol tautomerization is in most cases thermodynamically driven, and at room temperature, the equilibrium typically favors the formation of the keto form. However, environmental conditions such as, for example, the pH or ionic strength of a solution, the compound's concentration, the temperature, a presence of an agent that stabilizes the enol form, may shift the equilibrium towards the enol form being equally present or predominating.

In some embodiments, and depending on the environmental conditions, the compounds according to the present embodiments can be in the form of the keto tautomer (Formula Ia), or in the form of the enol form (Formula Ib), or can be equilibrating between the keto and enol forms, and thus take both forms of Formula Ia and Ib.

In some of any of the embodiments described herein, at least one of B, D, E and G is alkoxy or aryloxy, preferably alkoxy, and in some embodiments, at least two of B, D, E and G are alkoxy and/or aryloxy, preferably each being alkoxy.

In some of any of the embodiments described herein, the alkoxy is of 1-6 carbon atoms, preferably 1-4 carbon atoms. Examples include, without limitation, methoxy, ethoxy, propoxy, isopropoxy, butoxy and isobutoxy.

In some of any of the embodiments described herein, the alkoxy is methoxy.

In some of any of the embodiments described herein, B is alkoxy (e.g., methoxy).

In some of any of the embodiments described herein, no more than one of D, E and G is an alkyl.

In some of any of the embodiments described herein, no more than two of D, E and G are alkoxy or aryloxy.

In some of any of the embodiments described herein, when two of D, E and G are alkoxy and/or aryloxy, none of D, E and G is an alkyl.

In some of any of the embodiments described herein, one of D, E and G is hydrogen and the other two are alkoxy, aryloxy and/or alkyl, preferably alkoxy and/or alkyl.

In some of any of the embodiments described herein, D is hydrogen, E is alkoxy and G is alkyl.

In some of any of the embodiments described herein, D is hydrogen, and E and G are each independently an alkoxy, for example, E and G are each methoxy.

In some of any of the embodiments described herein, D and E are each independently an alkoxy, for example, D and E are each methoxy, and G is hydrogen.

In some of any of the embodiments described herein, D and G are each independently an alkoxy, for example, D and G are each methoxy, and E is hydrogen.

In some of any of the embodiments described herein, D is hydrogen, E is alkyl and G is alkoxy, for example, methoxy.

In some of any of the embodiments described herein, E is hydrogen, D is alkyl and G is alkoxy, for example, methoxy.

In some of any of the embodiments described herein, G is hydrogen, E is alkyl and D is alkoxy, for example, methoxy.

In some of any of the embodiments described herein, D is hydrogen, G is alkyl and E is alkoxy, for example, methoxy.

In some of any of the embodiments described herein, E is hydrogen, G is alkyl and D is alkoxy, for example, methoxy.

In some of any of the embodiments described herein, G is hydrogen, D is alkyl and E is alkoxy, for example, methoxy.

In some of any of the embodiments described herein, E is alkoxy (e.g., methoxy).

In some of any of the embodiments described herein, each of B and E is alkoxy (e.g., methoxy).

In some of any of the embodiments described herein, D is alkoxy (e.g., methoxy).

In some of any of the embodiments described herein, G is hydrogen.

In some of any of the embodiments described herein, E is alkoxy (e.g., methoxy), D is alkoxy (e.g., methoxy) and G is hydrogen. In some of these embodiments, B is alkoxy (e.g., methoxy).

In some of any of the embodiments described herein, E is alkoxy (e.g., methoxy), G is alkoxy (e.g., methoxy) and D is hydrogen. In some of these embodiments, B is alkoxy (e.g., methoxy).

In some of any of the embodiments described herein, E is alkoxy (e.g., methoxy), and D and G are both hydrogen. In some of these embodiments, B is alkoxy (e.g., methoxy).

In some of any of the embodiments described herein, D is alkoxy (e.g., methoxy), and E and G are both hydrogen. In some of these embodiments, B is alkoxy (e.g., methoxy).

In some of any of the embodiments described herein, G is alkoxy (e.g., methoxy), and D and E are both hydrogen. In some of these embodiments, B is alkoxy (e.g., methoxy).

In some of any of the embodiments described herein, D is said alkyl.

In some of these embodiments, one of G and E is hydrogen. In some of these embodiments, G is hydrogen and E is alkoxy.

In some of any of the embodiments described herein, E is alkoxy (e.g., methoxy), D is alkyl and G is hydrogen. In some of these embodiments, B is alkoxy (e.g., methoxy).

In some of any of the embodiments described herein, whenever one of D, E and G is alkyl, the alkyl is at least 4 carbon atoms in length.

In some of any of the embodiments described herein, an alkyl being at least 4 carbon atoms in length can be, for example, of 1 to 20, or of 1 to 10, or of 1 to 8 carbon atoms in length. Exemplary alkyls being at least 4 carbon atoms in length include substituted or unsubstituted butyl, substituted or unsubstituted pentyl, substituted or unsubstituted hexyl, substituted or unsubstituted heptyl, substituted or unsubstituted octyl, substituted or unsubstituted nonyl, substituted or unsubstituted decyl, substituted or unsubstituted undecyl, substituted or unsubstituted dodecyl, and so forth.

In some of any of the embodiments described herein, the alkyl being 4 carbon atoms in length is an unsubstituted alkyl. In some embodiments, it is hexyl, and in some embodiments, an unsubstituted hexyl.

In some of any of the embodiments described herein, A is an alkyl being at least 4 carbon atoms in length, and optionally one of D, E and G is an alkyl being at least 4 carbon atoms in length.

When both A and one of D, E, and G are an alkyl being 4 carbon atoms in length, these alkyls can be the same or different.

In some of these embodiments, both A and one of D, E and G are an unsubstituted alkyl and in some embodiments, both are unsubstituted hexyl.

In some of any of the embodiments described herein, $R_1$ is hydrogen.

In some of any of the embodiments described herein, each of $R_2$-$R_5$ is independently selected from hydrogen, hydroxy, halo, alkoxy, thioalkoxy, thiol, thioalkoxy, and amine.

In some of any of the embodiments described herein, each of $R_2$-$R_5$ is hydrogen.

In some of any of the embodiments described herein, each of $R_1$-$R_5$ is hydrogen.

Alternatively, one or more of $R_1$-$R_5$ is other than hydrogen and the nature of the respective substituent(s) is such that does not interfere with the interactions of the small molecule with its biological target(s) (e.g., chemokine binding and/or kinase inhibition).

In some of any of the embodiments described herein, a compound as described herein has the following chemical structure, represented by its keto and enol tautomers:

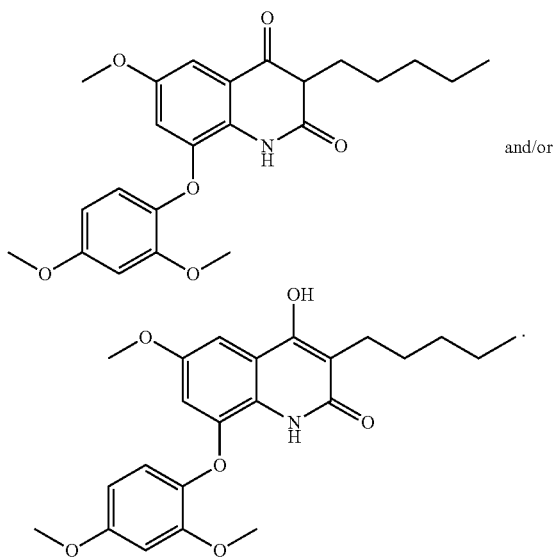

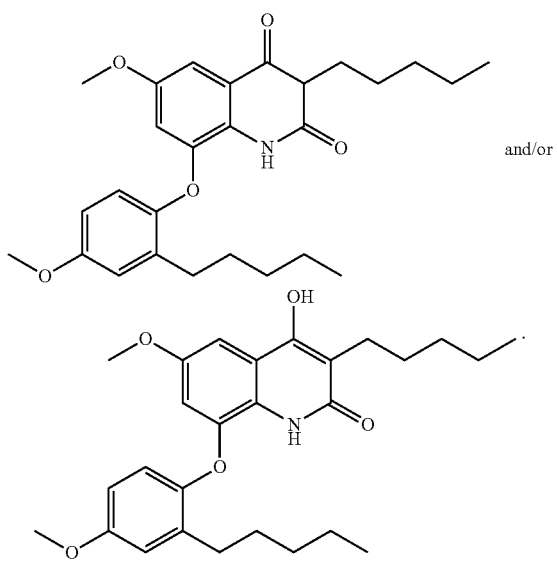

This compound is denoted herein BKT300-3-c5.

In some of any of the embodiments described herein, a compound as described herein has the following chemical structure, represented by its keto and enol tautomers:

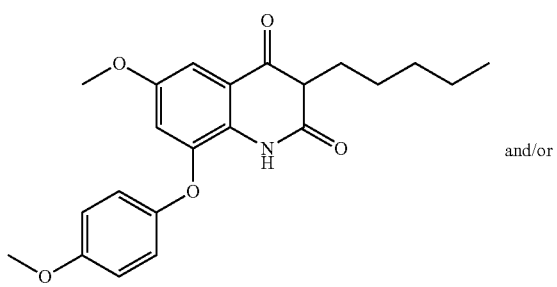

This compound is denoted herein BKT300-11-a5.

In some of any of the embodiments described herein, a compound as described herein has the following chemical structure, represented by its keto and enol tautomers:

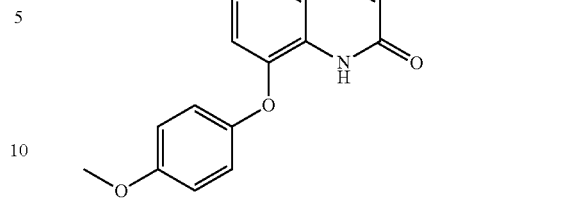

This compound is denoted herein B1.

In some of any of the embodiments described herein, a compound as described herein has the following chemical structure, represented by its keto and enol tautomers:

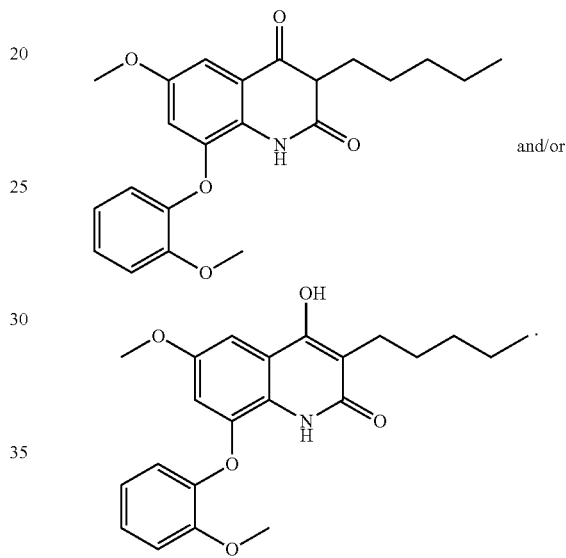

This compound is denoted herein D1.

Therapeutic Applications:

The compounds as described herein, in any one of the respective embodiments, and any combination thereof, can be regarded as structural analogs of BKT300, which is shown herein to act as a chemokine-binding compound, by modulating a biological activity of chemokines, as an inhibitor of chemokine-dependent cell migration, as an inhibitor of cancer cells (e.g., as inhibitor of cancer cells growth and/or as inducing apoptosis and/or as inhibitor of cancer cells migration), and/or as a kinase inhibitor.

Each of the compounds described herein is therefore capable of, or is useful in, inhibiting a biological activity of a kinase, and/or inhibiting cancer cells, and/or killing cancer cells, and/or inducing apoptosis, and/or inducing growth arrest, and/or inhibiting chemokine-dependent cell migration, and/or modulating a biological activity of a chemokine e.g., cell migration, and/or treating diseases and disorders associated with kinase activity and/or cell migration, such as cancer and inflammatory diseases and disorders; and/or treating proliferative diseases or disorders (where inducing apoptosis and/or growth arrest is desirable).

As inflammation and cancer are typically governed by cell migration (e.g., infiltration, metastasis) and kinase activity, which is often associated with cell proliferation, such conditions are contemplated for treatment using the compounds of some embodiments of the invention.

Proliferative diseases and disorders as described herein, including medical conditions other than cancer (also referred to herein as "non-cancerous hyperproliferative diseases"), are also contemplated for treatment using the compounds of some embodiments of the invention, due to the apoptosis-inducing effect of the compounds.

Without being bound by any particular theory, it is believed that the compounds described herein are particularly useful as anti-cancer agents by inducing cancer cell death, by affecting chemokine-dependent cancer cell migration (e.g., by inhibiting metastasis) and/or angiogenesis, and/or by inhibiting kinase activity (e.g., pro-proliferation kinase activity) and/or by inducing apoptosis of cancer cells and/or by inducing growth arrest of cancer cells; and/or as anti-inflammatory agents by affecting chemokine-dependent immune cell migration (e.g., immune cell infiltration) and/or by inhibiting kinase activity (e.g., pro-inflammatory kinase activity), as described in further detail hereinbelow.

In some of any of the embodiments described herein, a small molecule compound of Formula Ia and/or Ib, as described herein in any of the respective embodiments, is capable of, or usable in, inducing death of pathogenic cells (e.g., cancer cells or immune cells or hyper-proliferating cells).

In some of any of the embodiments described herein, a small molecule compound of Formula Ia and/or Ib, as described herein in any of the respective embodiments, is capable of, or usable in, inducing cell death of pathogenic cells.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

Methods of monitoring cellular changes induced by the compounds are known in the art and include for example, the MTT test which is based on the selective ability of living cells to reduce the yellow salt MTT (3-(4,5-dimethylthiazolyl-2)-2,5-diphenyltetrazolium bromide) (Sigma, Aldrich St Louis, Mo., USA) to a purple-blue insoluble formazan precipitate; the BrDu assay [Cell Proliferation ELISA BrdU colorimetric kit (Roche, Mannheim, Germany]; the TUNEL assay [Roche, Mannheim, Germany]; the Annexin V assay [ApoAlert® Annexin V Apoptosis Kit (Clontech Laboratories, Inc., CA, USA)]; the Senescence associated-β-galactosidase assay (Dimri G P, Lee X, et al. 1995. A biomarker that identifies senescent human cells in culture and in aging skin in vivo. Proc Natl Acad Sci USA 92:9363-9367); 7-ADD viability staining (available from MD systems), caspase-3 assay (available from MDsystems) as well as various RNA and protein detection methods (which detect level of expression and/or activity) which are further described hereinabove.

In some of any of the embodiments described herein, a small molecule compound of Formula Ia and/or Ib, as described herein in any of the respective embodiments, the cellular change is apoptosis such as via cleavage of caspase-3.

In some of any of the embodiments described herein, a small molecule compound of Formula Ia and/or Ib, as described herein in any of the respective embodiments, is capable of, or usable in, inducing apoptosis via cleavage of caspase-3.

In some of any of the embodiments described herein, a small molecule compound of Formula Ia and/or Ib, as described herein in any of the respective embodiments, is capable of, or usable in, inducing growth arrest of cells, and in some embodiments, the arrest is at the G2M phase of the cell cycle. In some of these embodiments, the cells are cancer cells.

Chemokine Modulation:

According an aspect of some embodiments of the present invention, a small molecule compound of Formula Ia and/or Ib, as described herein in any of the respective embodiments, and any combination thereof, is capable of, or is usable, in modulating a biological activity of a chemokine, as described herein.

According to an aspect of some embodiments of the present invention, there is provided a method of modulating a biological activity of a chemokine, the method comprising contacting the chemokine with a compound according to any of the embodiments described herein.

According to an aspect of some embodiments of the present invention, there is provided a use of a compound according to any of the embodiments described herein in the manufacture of a medicament for modulating a biological activity of a chemokine.

According to an aspect of some embodiments of the present invention, there is provided a use of a compound according to any of the embodiments described herein in modulating a biological activity of a chemokine.

In some embodiments, the use and/or method for modulating a chemokine activity is effected in vivo, for example by administering a therapeutically effective amount of the compound to a subject in need thereof.

In some embodiments, the use and/or method for modulating a chemokine activity is effected ex vivo (e.g., in vitro), for example, in research.

In some embodiments of any one of the embodiments described herein relating to a method, use or medicament for modulating a biological activity of a chemokine, the method, use or medicament is for treating a disease or disorder associated with a biological activity of a chemokine in a subject in need thereof, for example, by administering to the subject a therapeutically effective amount of a compound according to any of the embodiments described herein.

In some of any of the embodiments described herein, modulating a biological activity of a chemokine includes inhibiting a biological activity of a chemokine. This can be evidenced by the ability of a small molecule as described herein to inhibit chemokine-induced cell migration as exemplified herein on a plurality of cell types of different types.

In some embodiments of any one of the embodiments described herein relating to a method, use or medicament for modulating a biological activity of a chemokine, the method, use or medicament is for treating a disease or disorder in which modulating (e.g., inhibiting) a biological activity of a chemokine is beneficial, in a subject in need thereof, for example, by administering to the subject a therapeutically effective amount of a compound according to any of the embodiments described herein.

In some embodiments of any one of the embodiments described herein relating to a method, use or medicament for modulating a biological activity of a chemokine, the method, use or medicament is for treating a disease or disorder treatable by modulating (e.g., inhibiting) a biological activity of a chemokine, in a subject in need thereof, for example, by administering to the subject a therapeutically effective amount of a compound according to any of the embodiments described herein.

In some embodiments of any one of the embodiments described herein relating to a method, use or medicament for modulating a biological activity of a chemokine, the compound described herein (according to any of the respective embodiments) is effective in modulating chemokine-dependent cell migration. In some of these embodiments, the chemokine-dependent cell migration is associated with cancer and/or inflammation, as described herein.

In some of any of the embodiments described herein, the chemokine is MIP3a. Examples of diseases and disorders associated with an activity of MIP3a (e.g., wherein inhibition of MIP3a activity is beneficial) include, without limitation, autoimmune diseases and disorders such as psoriasis, inflammatory bowel disease, chronic obstructive pulmonary diseases (COPD), rheumatoid arthritis, multiple sclerosis (MS), atopic dermatitis, dry eye disease and age-related macular degeneration (AMD).

In some embodiments of any one of the embodiments described herein relating to a treatment of a disease or disorder, the disease or disorder is not a bacterial infection.

In some embodiments of any one of the embodiments described herein relating to a method or use for modulating a biological activity of a chemokine, the chemokine is MCP-1 and/or SDF-1. In some such embodiments, the chemokine is MCP-1. In some such embodiments, the chemokine is SDF-1.

In some embodiments of any one of the embodiments described herein relating to modulating a chemokine activity, the compound, method and/or medicament (according to any of the respective embodiments described herein) is for inhibiting a biological activity of a chemokine. In some such embodiments, the chemokine is MCP-1 and/or SDF-1. In some such embodiments, the chemokine is MCP-1. In some such embodiments, the chemokine is SDF-1.

MCP-1 Inhibition:

According to some embodiments, a small molecule compound of Formula Ia and/or Ib, as described herein in any of the respective embodiments, and any combination thereof, is capable of, or is usable, in modulating a biological activity of MCP-1, as described herein.

According to an aspect of some embodiments of the present invention, there is provided a method of inhibiting a biological activity of MCP-1, the method comprising contacting the MCP-1 with a compound according to any of the embodiments described herein described herein.

According to an aspect of some embodiments of the present invention, there is provided a use of a compound according to any of the embodiments described herein described herein in the manufacture of a medicament for inhibiting a biological activity of MCP-1.

According to an aspect of some embodiments of the present invention, there is provided a use of a compound according to any of the embodiments described herein described herein in inhibiting a biological activity of MCP-1.

In some embodiments of any of the embodiments relating to a use and/or method for inhibiting a biological activity of MCP-1, the use and/or method is effected in vivo, for example, by administering a therapeutically effective amount of the compound to a subject in need thereof.

In some embodiments, the use and/or method for inhibiting a biological activity of MCP-1 is effected ex vivo (e.g., in vitro), for example, in research.

In some embodiments of any one of the embodiments described herein relating to a method, use or medicament for inhibiting a biological activity of MCP-1, the method, use or medicament is for treating a disease or disorder associated with a biological activity of MCP-1 in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of MCP-1, the method, use or medicament is for treating a disease or disorder in which inhibiting a biological activity of a MCP-1 is beneficial, in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of MCP-1, the method, use or medicament is for treating a disease or disorder treatable by inhibiting a biological activity of a MCP-1 is beneficial, in a subject in need thereof, for example, by administering to the subject a therapeutically effective amount of a compound according to any of the embodiments described herein described herein.

Examples of diseases and disorders associated with an activity of MCP-1 (e.g., wherein inhibition of MCP-1 activity is beneficial) include, without limitation, diseases and disorders which are characterized by monocytic infiltrates.

According to some embodiments, examples of diseases and disorders associated with an activity of MCP-1 (e.g., wherein inhibition of MCP-1 activity is beneficial) include, without limitation, tuberculosis; HIV-1; proliferative glomerulonephritis; neural tube defects; xanthogranulomatous pyelonephritis; scleritis; rapidly progressive glomerulonephritis; pneumoconiosis; encephalitis; peritonitis; atherosclerosis; psoriasis; dengue shock syndrome; temporal arteritis; relapsing polychondritis; diabetic angiopathy; mesangial proliferative glomerulonephritis; sympathetic ophthalmia; ureteral disease; lupus nephritis; pneumonia; periapical granuloma; erdheim-chester disease; glomerulonephritis; artery disease; viral encephalitis; primary cutaneous amyloidosis; arteriosclerosis; nonspecific interstitial pneumonia; acute poststreptococcal glomerulonephritis; coronary artery disease; venezuelan equine encephalitis; diabetic macular edema; extrapulmonary tuberculosis; nephritis; rheumatoid arthritis; kawasaki disease; arthritis; malaria; obesity; psychiatric disorders; cancer (e.g., as described herein); inflammation (e.g., inflammatory disease and disorders as described herein); neurodegenerative disorders; and age-related macular degeneration (AMD, e.g., dry or wet form), as described herein.

According to a specific embodiment, the disease includes, without limitation, psoriasis, rheumatoid arthritis, multiple sclerosis, atherosclerosis, glomerulonephritis, epilepsy, Alzheimer's disease, brain ischemia, traumatic brain injury, type II diabetes and AMD.

SDF-1 and/or CXCR4 Inhibition:

According to some embodiments, a small molecule compound of Formula Ia and/or Ib, as described herein in any of the respective embodiments, and any combination thereof, is capable of, or is usable, in modulating a biological activity of SDF-1 and/or CXCR4, as described herein.

According to an aspect of some embodiments of the present invention, there is provided a method of inhibiting a biological activity of SDF-1 and/or CXCR4, the method comprising contacting the SDF-1 and/or CXCR4 with a compound according to any of the embodiments described herein described herein.

According to an aspect of some embodiments of the present invention, there is provided a use of a compound according to any of the embodiments described herein described herein in the manufacture of a medicament for inhibiting a biological activity of SDF-1 and/or CXCR4.

According to an aspect of some embodiments of the present invention, there is provided a use of a compound according to any of the embodiments described herein described herein in inhibiting a biological activity of SDF-1 and/or CXCR4.

In some embodiments of any of the embodiments relating to a use and/or method for inhibiting a biological activity of SDF-1 and/or CXCR4, the use and/or method is effected in vivo, for example, by administering a therapeutically effective amount of the compound to a subject in need thereof.

In some embodiments, the use and/or method for inhibiting a biological activity of SDF-1 and/or CXCR4 is effected ex vivo (e.g., in vitro), for example, in research.

In some embodiments of any one of the embodiments described herein relating to a method, use or medicament for inhibiting a biological activity of SDF-1 and/or CXCR4, the method, use or medicament is for treating a disease or disorder associated with a biological activity of SDF-1 and/or CXCR4 in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of SDF-1 and/or CXCR4, the method, use or medicament is for treating a disease or disorder in which inhibiting a biological activity of a SDF-1 and/or CXCR4 is beneficial, in a subject in need thereof, for example, by administering to the subject a therapeutically effective amount of a compound according to any of the embodiments described herein described herein.

In some embodiments of any one of the embodiments described herein relating to a method, use or medicament for inhibiting a biological activity of SDF-1 and/or CXCR4, the method, use or medicament is for treating a disease or disorder treatable by inhibiting a biological activity of a SDF-1 and/or CXCR4 is beneficial, in a subject in need thereof, for example, by administering to the subject a therapeutically effective amount of a compound according to any of the embodiments described herein described herein.

The skilled person will appreciate that CXCR4 is a receptor which mediates activity of SDF-1, and that activities of SDF-1 and activities of CXCR4 typically overlap.

Examples of diseases and disorders associated with an activity of SDF-1 and/or CXCR4 (e.g., wherein inhibition of SDF-1 and/or CXCR4 activity is beneficial) include, without limitation, Whim Syndrome; Cervical Adenocarcinoma; Breast Cancer; Bursitis; Tuberculosis; Intraocular Lymphoma; Cytomegalovirus Retinitis; Chronic Inflammatory Demyelinating Polyradiculoneuropathy; Ocular Hypertension; Polyradiculoneuropathy; Dendritic Cell Tumor; Retinal Hemangioblastoma; Malaria; Endotheliitis; Leukemia; Rheumatoid Arthritis; Arthritis; Prostatitis; Prostate Cancer; Colorectal Cancer; Chronic Lymphocytic Leukemia; Pancreatitis; Neuronitis; Lung Cancer; Osteoarthritis; Hypoxia; Adenocarcinoma; Pancreatic Cancer; Multiple Myeloma; Neuroblastoma; Myeloid Leukemia; Astrocytoma; Periodontitis; Glioblastoma; Pre-Eclampsia; Melanoma; Hepatitis; Esophagitis; Myeloma; Eclampsia; Cervicitis; Periodontal Disease; Central Nervous System Lymphoma; Sporadic Breast Cancer; Hepatocellular Carcinoma; Systemic Lupus Erythematosus; Asthma; Renal Cell Carcinoma; Myocardial Infarction; Medulloblastoma; Endometrial Cancer; Lupus Erythematosus; Esophageal Cancer; Premature Ovarian Failure; Peritonitis; Vascular Disease; Alcoholic Hepatitis; Kidney Disease; Cutaneous Leishmaniasis; Encephalitis; Alopecia Areata; Lymphoblastic Leukemia; Adenoma; Mantle Cell Lymphoma; Oligodendroglioma; Malt Lymphoma; Pertussis; Ischemia; Uveal Melanoma; Gingivitis; Pituitary Adenoma; Bronchiolitis; Neuromyelitis Optica; Mesothelioma; Alopecia; Cervical Cancer, Somatic; Glioblastoma Multiforme; Bronchiolitis Obliterans; Brain Injury; Colorectal Adenoma; Tongue Squamous Cell Carcinoma; B-Cell Lymphomas; Traumatic Brain Injury; Intravascular Large B-Cell Lymphoma; Allergic Asthma; Tick-Borne Encephalitis; Blastic Plasmacytoid Dendritic Cell; Oligoastrocytoma; Childhood Type Dermatomyositis; Renal Oncocytoma; Endometrial Adenocarcinoma; Optic Neuritis; Seminoma; Sjogren's Syndrome; Pleurisy; Neuritis; Inflammatory Bowel Disease; Cytomegalovirus Infection; Malignant Pleural Mesothelioma; Oral Squamous Cell Carcinoma; Skeletal Muscle Regeneration; Emery-Dreifuss Muscular Dystrophy, Dominant Type.

In some embodiments, exemplary diseases and disorders associated with an activity of SDF-1 and/or CXCR4 (e.g., wherein inhibition of SDF-1 and/or CXCR4 activity is beneficial) include, without limitation, harmful angiogenesis, tumor metastasis, WHIM syndrome, Waldenstrom macroglobuolinaemia (WM) and opioid-induced hyperalgesia.

Herein, the term "harmful angiogenesis" refers to angiogenesis associated with a clinically and/or cosmetically undesirable result.

Angiogenesis associated with a tumor is a non-limiting example of a harmful angiogenesis.

As used herein the phrase "tumor metastasis" refers to a malignant tumor spreading out of its primary location to other parts of the body, e.g., breast cancer which metastasizes to the lungs. Tumor metastasis often involves migration of tumor cells.

In some embodiments of any one of the embodiments described herein relating to a method or use for modulating a biological activity of a chemokine, the modulating comprises inhibiting a biological activity of SDF-1 and/or CXCR4, according to any of the respective embodiments described herein.

In some embodiments of any one of the embodiments described herein relating to inhibiting a biological activity of SDF-1 and/or CXCR4, inhibiting a biological activity of SDF-1 and/or CXCR4 is for effecting immunostimulation.

In some embodiments, immunostimulation is effected as part of a cancer treatment, e.g., in order to stimulate immune activity against cancer cells.

In some embodiments, immunostimulation comprises increasing a level of hematopoietic stem cells in peripheral blood of a subject.

In some embodiments, increasing a level of hematopoietic stem cells in peripheral blood of a subject is effected as a preliminary part of hematopoietic stem cell transplantation (e.g., in order to generate hematopoietic stem cells available for collection and later transplantation back into the subject). Examples of conditions which may be treated by the hematopoietic stem cell transplantation include, without limitation, leukemia (e.g., acute lymphoblastic leukemia, acute myeloid leukemia, chronic lymphocytic leukemia, chronic myelogenous leukemia), lymphoma (e.g., Hodgkin's disease, non-Hodgkin's lymphoma), myeloma (e.g., multiple myeloma), neuroblastoma, desmoplastic small round cell tumor, Ewing's sarcoma, choriocarcinoma, myelodysplasia, anemias (e.g., paroxysmal nocturnal hemoglobinuria, aplastic anemia, Diamond-Blackfan anemia, Fanconi anemia, acquired pure red cell aplasia), hemoglobinopathies, sickle cell disease, beta-thalassemia major, myeloproliferative disorders (e.g., polycythemia vera, essential thrombocytosis, myelofibrosis), amyloid light chain amyloidosis, radiation poisoning, viral diseases (e.g., HTLV and/or HIV infection), neuronal ceroid lipofuscinosis, Niemann-Pick disease, Gaucher disease, leukodystrophies (adrenoleukodystrophy, metachromatic leukodystrophy, Krabbe disease), mucopolysaccharidosis, glycoproteinoses (e.g., mucolipidosis II, fucosidosis, aspartylglucosaminuria, alpha-mannosidosis), Wolman disease, immunodeficiencies (e.g., ataxia telangiectasia, DiGeorge syndrome, severe combined immunodeficiency, Wiskott-Aldrich syndrome, Kostmann syndrome, Shwachman-Diamond syndrome, Griscelli syndrome, NF-kappa-B essential modulator deficiency), amegakaryocytic thrombocytopenia and hemophagocytic lymphohistiocytosis.

In some embodiments, the hematopoietic stem cell transplantation is for treating a proliferative disease, e.g., cancer (e.g., cancer as described herein according to any of the respective embodiments).

In some embodiments of any one of the embodiments described herein relating to hematopoietic stem cells, the treatment comprises increasing a level of hematopoietic stem cells in peripheral blood of the subject, obtaining hematopoietic stem cells from peripheral blood of the subject, administering a cytotoxic therapy to the subject (e.g., anti-proliferative chemotherapy, and/or radiotherapy), and transplanting at least a portion of the stem cells back into the patient, subsequent to the cytotoxic therapy.

Kinase Inhibition:

According to some of any of the embodiments described herein, a compound represented by Formula Ia and/or Ib herein is capable of, or is usable in, inhibiting a biological activity of a kinase.

According to some of any of the embodiments described herein, a compound represented by Formula Ia and/or Ib herein is capable of, or is usable in, treating diseases or disorder in which inhibiting a biological activity of a kinase is beneficial, or a disease or disorder that is treatable by inhibiting a biological activity of a kinase.

According to an aspect of some embodiments of the present invention, a compound according to any of the embodiments described herein, is for use in inhibiting a biological activity of a kinase.

According to another aspect of some embodiments of the present invention, there is provided a method of inhibiting a biological activity of a kinase, the method comprising contacting the kinase with a compound according to any of the embodiments described herein.

In some embodiments, the use and/or method for inhibiting a kinase is effected ex vivo (e.g., in vitro), for example, in research.

In some embodiments, the use and/or method for inhibiting a kinase is effected in vivo, for example by administering a therapeutically effective amount of the compound to a subject in need thereof.

According to another aspect of some embodiments of the present invention, there is provided a use of a compound according to any of the embodiments described herein in the manufacture of a medicament for use in inhibiting a biological activity of a kinase in a subject in need thereof.

In some embodiments of any one of the embodiments described herein relating to a use, method and/or medicament for inhibiting a biological activity of a kinase, the use, method and/or medicament (according to any of the respective embodiments described herein) is for use in treating a disease or disorder associated with a biological activity of a kinase in a subject in need thereof.

In some embodiments of any one of the embodiments described herein relating to a use, method and/or medicament for inhibiting a biological activity of a kinase, the use, method and/or medicament is for use in treating a disease or disorder in which inhibition of a biological activity of a kinase is beneficial.

In some embodiments of any one of the embodiments described herein relating to a use, method and/or medicament for inhibiting a biological activity of a kinase, the use, method and/or medicament is for treating a disease or disorder which is treatable by inhibition of a biological activity of a kinase.

In some embodiments of any one of the embodiments described herein relating to a method or use for inhibiting a biological activity of a kinase, the inhibited kinase can be a kinase presented in Table 2 below, for example, DYRK3, EPHA8, GRK4, GRK5, MAP4K1, MAP4K2, MAP4K4, MELK, PAK7, SGK2, SRC N1, ACVRL1, BMPR1A, CDC7/DBF4, CDK1/cyclin A2, CDK11, CDK8/cyclin C, CLK4, DAPK2, DURK2, ICK, MAPK10, MLCK, MYLK, NUAK2, STK17A, STK17B, STK38, STK38L, TGFBR2, TTK, DAPK1, PIK3CA and/or PIK3CD.

According to a specific embodiment, the kinase is a PI3K.

In some embodiments of any one of the embodiments described herein relating to a method or use for inhibiting a biological activity of a kinase, the inhibited kinase is a serine/threonine kinase. In some embodiments, the serine/threonine kinase is a serine/threonine kinase presented in Table 2 below.

In some embodiments of any one of the embodiments described herein relating to a method or use for inhibiting a biological activity of a kinase, the inhibited kinase is a tyrosine kinase. In some embodiments, the tyrosine kinase is a serine/threonine kinase presented in Table 2 below.

In some embodiments of any one of the embodiments described herein relating to a method or use for inhibiting a biological activity of a kinase, the kinase is MELK, MAP4K4 and/or PI3K.

Cancer Treatment:

According to some embodiments, a small molecule compound of Formula Ia and/or Ib, as described herein in any of the respective embodiments, and any combination thereof, is capable of, or is usable, in treating cancer.

According to some embodiments, a small molecule compound of Formula Ia and/or Ib, as described herein in any of the respective embodiments, and any combination thereof, is capable of, or is usable, in inducing death of cancer cells (killing cancer cells).

According to some embodiments, a small molecule compound of Formula Ia and/or Ib, as described herein in any of the respective embodiments, and any combination thereof, is capable of, or is usable, inducing apoptosis in cancer cells.

According to some embodiments, a small molecule compound of Formula Ia and/or Ib, as described herein in any of the respective embodiments, and any combination thereof, is capable of, or is usable, in inducing growth arrest in cancer cells, and in some embodiments, the arrest is at the G2M phase of the cell cycle.

According to an aspect of some embodiments of the present invention, there is provided a method of treating a cancer in a subject in need thereof, the method comprising administering to the subject a therapeutically effective amount of a small molecule compound according to any of the embodiments described herein, thereby treating the cancer.

According to an aspect of some embodiments of the present invention, there is provided a use of a small molecule compound according to any of the embodiments described herein in the manufacture of a medicament for treating cancer.

According to an aspect of some embodiments of the present invention, there is provided a use of a small molecule compound according to any of the embodiments described herein in treating cancer.

As used herein, the terms "cancer" and "tumor" are interchangeably used. The terms refer to a malignant growth and/or tumor caused by abnormal and uncontrolled cell proliferation (cell division). The term "cancer" encompasses tumor methastases. The term "cancer cell" describes the cells forming the malignant growth or tumor.

Non-limiting examples of cancers and/or tumor metastases which can be treated according to some embodiments of any of the embodiments described herein relating to cancer (including any of the aspects described herein) include any solid or non-solid cancer and/or tumor metastasis, including, but not limiting to, tumors of the gastrointestinal tract (e.g., colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic breast cancer, susceptibility to breast cancer, type 4 breast cancer, breast cancer-1, breast cancer-3, breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B-cell lymphoma, Diffuse large B-cell lymphoma (DLBCL), Burkitt lymphoma, cutaneous T-cell lymphoma, histiocytic lymphoma, lymphoblastic lymphoma, T-cell lymphoma, thymic lymphoma), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B-cell), hypernephroma, insulinoma, islet tumor, keratoma, leiomyoblastoma, leiomyosarcoma, leukemia (e.g., acute lymphatic leukemia, acute lymphoblastic leukemia, acute lymphoblastic pre-B cell leukemia, acute lymphoblastic T cell leukemia, acute megakaryoblastic leukemia, monocytic leukemia, acute myelogenous leukemia, acute myeloid leukemia, acute myeloid leukemia with eosinophilia, B-cell leukemia, basophilic leukemia, chronic myeloid leukemia, chronic B-cell leukemia, eosinophilic leukemia, Friend leukemia, granulocytic or myelocytic leukemia, hairy cell leukemia, lymphocytic leukemia, megakaryoblastic leukemia, monocytic leukemia, monocytic-macrophage leukemia, myeloblastic leukemia, myeloid leukemia, myelomonocytic leukemia, plasma cell leukemia, pre-B cell leukemia, promyelocytic leukemia, subacute leukemia, T-cell leukemia, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme, multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

In some embodiments of any one of the embodiments described herein relating to cancer, the cancer is a leukemia, a lymphoma, ovarian cancer, neuroblastoma, a prostate cancer and/or a lung cancer. Examples of leukemias which may be treated in the context of some embodiments of the invention include, without limitation, acute leukemias, for example, acute myeloid leukemia (AML), chronic myeloid leukemia (CML) and acute lymphoblastic leukemia.

Examples of lymphomas which may be treated in the context of some embodiments of the invention include, without limitation, Diffuse large B-cell lymphoma (DLBCL), multiple myeloma and non-Hodgkin's lymphomas. Burkitt lymphoma is a non-limiting example of a non-Hodgkin's lymphoma.

Examples of lung cancers which may be treated in the context of some embodiments of the invention include, without limitation, large cell lung cancer and small cell lung cancer.

In some embodiments of any one of the embodiments described herein relating to cancer, the cancer is characterized by cells expressing CXCR4. In some such embodiments, the compound for use in treating cancer is any one of the compounds described herein as being for use in inhibiting SDF-1 and/or CXCR4 activity.

Without being bound by any particular theory, it is believed that in cancers characterized by expression of CXCR4, the activity of SDF-1 and CXCR4 is generally associated with metastasis, and thus, treatment with an inhibitor of SDF-1 and/or CXCR4 activity is particularly advantageous.

In some embodiments of any one of the embodiments described herein relating to treatment of cancer, the cancer further comprises administering at least one additional anti-cancer agent (i.e., in addition to the compound described hereinabove).

The additional anti-cancer agent may be any agent used in the medical arts to treat a cancer. Examples of anti-cancer agents include, without limitation, acivicin; aclarubicin; acodazole hydrochloride; acronine; adriamycin; Adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; combrestatin A-4 phosphate; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ombrabulin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofuirin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine; vincristine sulfate; vindesine; vindesine sulfate; vinepidinee; vinglycinate; vinleurosine; vinorelbine tartrate; vinrosidine; vinzolidine; vorozole; zeniplatin; zinostatin; and zorubicin hydrochloride. Additional anti-cancer agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division), the contents of which are incorporated herein by reference.

In some embodiments of any of the embodiments described herein, the additional anti-cancer agent is characterized in that resistance of cancer cells to the agent is associated with an activity of SDF-1 and/or CXCR4 and/or any one of the kinases described in Table 2 herein. In some such embodiments, the compound for use in combination with the additional anti-cancer agent is any one of the compounds described herein.

In some embodiments of any of the embodiments described herein, the at least one additional anti-cancer agent comprises combrestatin A-4 phosphate, ombrabulin and/or any other derivative of combrestatin.

Without being bound by any particular theory, it is believed that the anti-therapeutic effect of combrestatin derivatives such as combrestatin A-4 phosphate and ombrabulin is reduced by SDF-1/CXCR4 activity.

Non-Cancerous Hyperproliferative Diseases:

Non-cancerous hyperproliferative diseases also referred to "non-neoplastic proliferative diseases" and "non-cancerous proliferative diseases" refer to diseases or disorders which onset or progression is associated with non-malignant cell proliferation. Examples of such medical conditions include, but are not limited to atherosclerosis, rheumatoid arthritis, psoriasis, fibrosis, idiopathic pulmonary fibrosis, scleroderma and cirrhosis of the live.

Inflammatory Diseases and Disorders:

Inflammatory diseases and disorders generally encompass diseases and disorders associated with inflammation.

The term "inflammation" as used herein refers to the general term for local accumulation of fluids, plasma proteins, and white blood cells initiated by physical injury, infection, or a local immune response. Inflammation may be associated with several signs e.g. redness, pain, heat, swelling and/or loss of function. Inflammation is an aspect of many diseases and disorders, including but not limited to diseases related to immune disorders, viral and bacterial infection, arthritis, autoimmune diseases, collagen diseases, allergy, asthma, pollinosis, and atopy (as described in further detail below).

Thus, inflammation can be triggered by injury, for example injury to skin, muscle, tendons, or nerves. Inflammation can be triggered as part of an immune response, e.g., pathologic autoimmune response. Inflammation can also be triggered by infection, where pathogen recognition and tissue damage can initiate an inflammatory response at the site of infection.

Inflammation according to the present teachings may be associated with chronic (long term) inflammatory diseases or disorders or acute (short term) inflammatory diseases or disorders.

According to a specific embodiment, the inflammation is associated with a disease selected from the group consisting of an infectious disease, an autoimmune disease, a hypersensitivity associated inflammation, a graft rejection and an injury.

According to a specific embodiment, the inflammation comprises a skin inflammation.

According to a specific embodiment, the skin inflammation is psoriasis.

Diseases characterized by inflammation of the skin, include but are not limited to dermatitis, atopic dermatitis (eczema, atopy), contact dermatitis, dermatitis herpetiformis, generalized exfoliative dermatitis, seborrheic dermatitis, drug rashes, erythema multiforme, erythema nodosum, granuloma annulare, poison ivy, poison oak, toxic epidermal necrolysis, roseacae, psoriasis and acne. Inflammation can also result from physical injury to the skin.

Inflammation may be triggered by various kinds of injuries to muscles, tendons or nerves. Thus, for example, inflammation may be caused by repetitive movement of a part of the body i.e. repetitive strain injury (RSI). Diseases characterized by inflammation triggered by RSI include, but are not limited to, bursitis, carpal tunnel syndrome, Dupuytren's contracture, epicondylitis (e.g. tennis elbow), ganglion (i.e. inflammation in a cyst that has formed in a tendon sheath, usually occurring on the wrist), rotator cuff syndrome, tendinitis (e.g., inflammation of the Achilles tendon), tenosynovitis, and trigger finger (inflammation of the tendon sheaths of fingers or thumb accompanied by tendon swelling).

Many diseases related to infectious diseases include inflammatory responses, where the inflammatory responses are typically part of the innate immune system triggered by the invading pathogen. Inflammation can also be triggered by physical (mechanical) injury to cells and tissues resulting from the infection. Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases. According to one embodiment, examples of infections characterized by inflammation include, but are not limited to, encephalitis; meningitis; encephalomyelitis; viral gastroenteritis; viral hepatitis.

Furthermore, many immune disorders include acute or chronic inflammation. For example, arthritis is considered an immune disorder characterized by inflammation of joints, but arthritis is likewise considered an inflammatory disorder characterized by immune attack on joint tissues.

Inflammation according to the present teachings may be associated with a deficient immune response (e.g., HIV, AIDS) or with an overactive immune response (e.g., allergy, autoimmune disorders). Thus, inflammation according to the present teachings may be associated with any of the following:

Inflammatory Diseases Associated with Hypersensitivity:

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like f3-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000

August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

According to a specific embodiment, the ocular disease is age-related macular degeneration (AMD).

According to a specific embodiment, the age-related macular degeneration (AMD) is atrophic, non-neovascular (aAMD).

According to a specific embodiment, the age-related macular degeneration (AMD) is neovascular.

Autoimmune Diseases:

Autoimmune diseases include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome, diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

According to one embodiment, the autoimmune disease is Crohn's disease, psoriasis, scleroderma or rheumatoid arthritis.

Graft Rejection Diseases:

Examples of diseases associated with transplantation of a graft include, but are not limited to, graft rejection, chronic graft rejection, subacute graft rejection, hyperacute graft rejection, acute graft rejection and graft versus host disease.

Allergic Diseases:

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Pharmaceutical Compositions:

The compounds described herein according to any of the aspects of embodiments of the invention described herein can be utilized (e.g., administered to a subject) per se or in a pharmaceutical composition where the compound is mixed with suitable carriers or excipients.

As used herein a "pharmaceutical composition" refers to a preparation of one or a compound according to any of the embodiments described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

When utilized per se or in a pharmaceutically acceptable composition, the compound per se (that is, not including, weight of carriers or excipients co-formulated with the compound, as described herein) is optionally at least 80% pure (by dry weight), optionally at least 90% pure (by dry weight), at least 95% pure (by dry weight), at least 98% pure (by dry weight), and optionally at least 99% pure (by dry weight). Purity may be enhanced, e.g., by removing impurities associated with synthesis of the compound or isolation of the compound from a natural source, by any suitable technique known in the art. As exemplified herein, impurities of a compound described herein (for example, BKT300) may weaken a biological effect of the compound.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, breast tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the active compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of the active ingredient(s) effective to prevent, alleviate or ameliorate symptoms of a disorder (e.g., cancer or metastatic cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (see, e.g., Fingl et al. (1975), in "The Pharmacological Basis of Therapeutics", Ch. 1 p. 1).

Dosage amount and interval may be adjusted individually to provide protein (e.g., MCP-1, SDF-1 and/or CXCR4) inhibitory levels of the active ingredient are sufficient to induce or suppress the biological effect (minimal effective concentration, MEC). The MEC will vary for each preparation, but can be estimated from in vitro data, e.g., based on results on chemokine-induced (e.g., MCP-1- and/or SDF-1-induced) migration inhibition assay described herein. Dosages necessary to achieve the MEC will depend on individual characteristics and route of administration. Detection assays can be used to determine plasma concentrations.

In some embodiments of any of the embodiments described herein, an effective amount of the compound is less than 100 µM. In some embodiments, an effective amount is less than 10 µM. In some embodiments, an effective amount is less than 5 µM. In some embodiments, an effective amount is less than 2.5 µM.

In some embodiments of any of the embodiments described herein, an effective amount is at least 100% of the IC50 of the compound towards a chemokine which is intended to be inhibited (e.g., MCP-1 and/or SDF-1). In some embodiments, an effective amount is at least 200% of the IC50 of the compound towards the chemokine. In some embodiments, an effective amount is at least 300% of the IC50 of the compound towards the chemokine. In some embodiments, an effective amount is at least 500% of the IC50 of the compound towards the chemokine. In some embodiments, an effective amount is at least 1000% of the IC50 of the compound towards the chemokine.

In some embodiments of any of the embodiments described herein, an effective amount is at least 100% of the IC50 of the compound towards inducing cell death of cancer cells to be inhibited. In some embodiments, an effective amount is at least 200% of the IC50 of the compound towards the cancer cells. In some embodiments, an effective amount is at least 300% of the IC50 of the compound towards the cancer cells.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more units dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed herein.

It will be appreciated that the compounds described herein can be provided alone or in combination with other active ingredients, which are well known in the art for alleviating the medical condition.

Thus, for example, the compound may be administered with an immunomodulator, either together in a co-formulation or in separate formulations.

According to a specific embodiment, the treatment of cancer (and other hyperproliferative disorders) is effected in combination with an anti-cancer immune modulator agent.

As used herein, the term "anti-cancer immune modulator agent" refers to an agent capable of eliciting an immune response (e.g. T cell, NK cell) against a cancerous cell.

According to specific embodiment, the agent is selected from the group consisting of a cancer antigen, a cancer vaccine, an anti-cancer antibody, a cytokine capable of inducing activation and/or proliferation of a T cell and an immune-check point regulator.

Alternatively or additionally, such modulators may be immune stimulators such as immune-check point regulators which are of specific value in the treatment of cancer.

As used herein the term "immune-check point regulator" refers to a molecule that modulates the activity of one or more immune-check point proteins in an agonistic or antagonistic manner resulting in activation of an immune cell.

As used herein the term "immune-check point protein" refers to a protein that regulates an immune cell activation or function. Immune check-point proteins can be either co-stimulatory proteins (i.e. transmitting a stimulatory signal resulting in activation of an immune cell) or inhibitory proteins (i.e. transmitting an inhibitory signal resulting in suppressing activity of an immune cell). According to specific embodiment, the immune check point protein regulates activation or function of a T cell. Numerous checkpoint proteins are known in the art and include, but not limited to, PD1, PDL-1, B7H2, B7H4, CTLA-4, CD80, CD86, LAG-3, TIM-3, KIR, IDO, CD19, OX40, 4-1BB (CD137), CD27, CD70, CD40, GITR, CD28 and ICOS (CD278).

According to specific embodiments, the immune-checkpoint regulator is selected form the group consisting of anti-CTLA4, anti-PD-1, and CD40 agonist.

According to specific embodiments, the immune-check point regulator is selected form the group consisting of anti-CTLA4, anti-PD-1, anti-PDL-1, CD40 agonist, 4-1BB agonist, GITR agonist and OX40 agonist.

CTLA4 is a member of the immunoglobulin superfamily, which is expressed on the surface of Helper T cells and transmits an inhibitory signal to T cells upon ligand binding. As used herein, the term "anti-CTLA4" refers to an antagonistic molecule that binds CTLA4 (CD152) and suppresses its suppressive activity. Thus, an anti-CTLA4 prevents the transmission of the inhibitory signal and thereby acts as a co-stimulatory molecule. According to a specific embodiment, the anti-CDLA4 molecule is an antibody.

PD-1 (Programmed Death 1) is a member of the extended CD28/CTLA-4 family of T cell regulators which is expressed on the surface of activated T cells, B cells, and macrophages and transmits an inhibitory signal upon ligand binding. As used herein, the term "anti-PD1" refers to an antagonistic molecule that binds PD-1 and suppresses it's suppressive activity. Thus, an anti-PD-1 prevents the transmission of the inhibitory signal and thereby acts as a co-stimulatory molecule. According to a specific embodiment, the anti-PD1 molecule is an antibody. Numerous anti-PD-1 antibodies are known in the art see e.g. Topalian, et al. NEJM 2012.

PDL-1 is a ligand of PD-1. Binding of PDL-1 to its receptor PD-1 transmits an inhibitory signal to the cell expressing the PD-1. As used herein, the tem "anti-PDL-1" refers to an antagonistic molecule that inhibits PD-1 signaling by binding to or inhibiting PD-L1 from binding and/or activating PD-1. Thus, an anti-PD-1 prevents the transmission of the inhibitory signal and thereby acts as a co-stimulatory molecule. According to specific embodiments, the anti-PD-L1 is an anti-PD-L1 antibody. Numerous anti-PDL-1 antibodies are known in the art see e.g. Brahmer, et al. NEJM 2012.

CD40 (CD154) is a co-stimulatory receptor found on antigen presenting cells and transmits an activation signal upon ligand binding. As used herein, the term "CD40 agonist" refers to an agonistic molecule that binds CD40 (CD154) and thereby induces activation of the antigen presenting cell.

OX40 belongs to the TNF receptor super family and leads to expansion of CD4+ and CD8+ T cells. As used herein, the term "OX40 agonist" refers to an agonistic molecule that binds and activates OX40.

GITR (glucocorticoid-induced tumor necrosis factor receptor) is a surface receptor molecule that has been shown to be involved in inhibiting the suppressive activity of T-regulatory cells and extending the survival of T-effector cells. As used herein, the term "GITR agonist" refers to an agonistic molecule that binds and activates GITR. According to a specific embodiment, the GITR agonist is an antibody.

According to another aspect described herein, there is provided a kit for the treatment of a condition (e.g., treatment of cancer or prevention of tumor metastasis or treatment of non-cancerous proliferative disease or disorder or treatment of inflammation) described herein, the kit comprising a packaging material packaging the compound described herein.

In some embodiments, the compound is identified as an inhibitor of an SDF-1 and/or CXCR4 activity associated with an onset or progression of the condition, as described herein.

In some embodiments, the compound is identified as an inhibitor of a kinase activity associated with an onset or progression of the condition, as described herein.

In some embodiments, the compound is identified as inducing apoptosis and/or cell growth arrest of cells associated with the condition, as described herein.

Definitions

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. For example, in the context of preventing metastasis and/or angiogenesis, the term "preventing" refers to arresting, halting, inhibiting the metastatic and/or angiogenetic process or progression and subsequent metastasis and/or angiogenesis.

As used herein the term "subject" refers to a mammal (e.g., human), for example, one who has been diagnosed with a condition described herein (e.g., cancer).

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicated number and a second indicated number and "ranging/ranges from" a first indicated number "to" a second indicated number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein throughout, the phrase "linking group" describes a group (a substituent) that is attached to another moiety in the compound via two or more atoms thereof. In order to differentiate a linking group from a substituent that is attached to another moiety in the compound via one atom thereof, the latter will be referred to herein and throughout as an "end group".

As used herein, the term "amine" describes both a —NR'R" end group and a —NR'— linking group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is or forms a part of a linking group.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a medium size alkyl having 1 to 10 carbon atoms. Unless otherwise indicated, the alkyl is a lower alkyl having 1 to 4 carbon atoms. In some embodiments, the alkyl has at least 4 carbon atoms, for example, the alkyl is having 4 to 12 or 4 to 10 or 4 to 8 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfinate, sulfate, sulfonate, sulfoxide, phosphonate, hydroxy, alkoxy, aryloxy, thiohydroxy, thioalkoxy, thioaryloxy, oxo, carbonyl, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When an alkyl is a linking group, it is also referred to herein as "alkylene", e.g., methylene, ethylene, propylene, etc.

The term "alkenyl" describes an alkyl, as defined herein, in which at least one pair of carbon atoms are linked to one another via a double bond.

The term "alkynyl" or "alkyne" describes an alkyl, as defined herein, in which at least one pair of carbon atoms are linked to one another via a triple bond.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfinate, sulfate, sulfonate, sulfoxide, phosphonate, hydroxy, alkoxy, aryloxy, thiohydroxy, thioalkoxy, thioaryloxy, oxo, carbonyl, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfinate, sulfate, sulfonate, sulfoxide, phosphonate, hydroxy, alkoxy, aryloxy, thiohydroxy, thioalkoxy, thioaryloxy, oxo, carbonyl, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfinate, sulfate, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof. Preferably, the aryl is phenyl. Optionally, the aryl is naphthalenyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, triazine, tetrazine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfinate, sulfate, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof.

The term "alkaryl" describes an alkyl, as defined herein, which is substituted by one or more aryl or heteroaryl groups. An example of alkaryl is benzyl.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" or "sulfinyl" describes a —S(=O)—OR' end group or an —S(=O)—O— group linking group, as these phrases are defined hereinabove, where R' is as defined hereinabove.

The term "sulfoxide" describes a —S(=O)R' end group or an —S(=O)— linking group, as these phrases are defined hereinabove, where R' is as defined hereinabove.

The term "sulfonate" or "sulfonyl" describes a —S(=O)$_2$—OR' end group (also referred to herein as —SO$_3$R' or —SO$_3$H) or an —O—S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "phosphonate" describes a —P(=O)(OR')(OR") end group or a —P(=O)(OR')(O)— linking group, as these phrases are defined hereinabove, with R' and R" as defined herein.

The term "thiophosphonate" describes a —P(=S)(OR')(OR") end group or a —P(=S)(OR')(O)— linking group, as these phrases are defined hereinabove, with R' and R" as defined herein.

The term "carbonyl" or "carbonate" or "ketone" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxo" as used herein, described a =O end group.

The term "thiooxo" as used herein, described a =S end group.

The term "oxime" describes a =N—OH end group or a =N—O— linking group, as these phrases are defined hereinabove.

The term "hydroxyl" or "hydroxy" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" or "thio" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" or "nitrile" describes a —C≡N group.

The term "isocyanate" describes an —N=C=O group.

The term "nitro" describes an —NO$_2$ group.

The term "carboxylate" as used herein encompasses C-carboxylate and O-carboxylate.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "thiocarboxylate" as used herein encompasses "C-thiocarboxylate and O-thiocarboxylate.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "carbamate" as used herein encompasses N-carbamate and 0-carbamate.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "thiocarbamate" as used herein encompasses N-thiocarbamate and O-thiocarbamate.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "dithiocarbamate" as used herein encompasses N-dithiocarbamate and S-dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "amide" as used herein encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "guanyl" describes a R'R"NC(=N)— end group or a —R'NC(=N)— linking group, as these phrases are defined hereinabove, where R' and R" are as defined herein.

The term "guanidine" describes a —R'NC(=N)—NR"R'" end group or a —R'NC(=N)—NR"— linking group, as these phrases are defined hereinabove, where R', R" and R'" are as defined herein.

The term "hydrazine" describes a —NR'—NR"R'" end group or a —NR'—NR"-linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

For any of the embodiments described herein, the compound described herein may be in a form of a salt thereof, for example, a pharmaceutically acceptable salt thereof, and/or in a form of a prodrug thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be a base addition salt comprising at least one acidic (e.g., phenol and/or carboxylic acid) group of the compound which is in a negatively charged form (e.g., wherein the acidic group is deprotonated), in combination with at least one counter-ion, derived from the selected base, that forms a pharmaceutically acceptable salt.

The base addition salts of the compounds described herein may therefore be complexes formed between one or more acidic groups of the drug and one or more equivalents of a base.

The base addition salts may include a variety of organic and inorganic counter-ions and bases, such as, but not limited to, sodium (e.g., by addition of NaOH), potassium (e.g., by addition of KOH), calcium (e.g., by addition of $Ca(OH)_2$, magnesium (e.g., by addition of $Mg(OH)_2$), aluminum (e.g., by addition of $Al(OH)_3$ and ammonium (e.g., by addition of ammonia). Each of these acid addition salts can be either a mono-addition salt or a poly-addition salt, as these terms are defined herein.

In the context of some of the present embodiments, a pharmaceutically acceptable salt of the compounds described herein may optionally be an acid addition salt comprising at least one base group (e.g., amine or amide group) of the compound which is in a positively charged form (e.g., wherein an —NH— group is protonated), in combination with at least one counter-ion, derived from the selected acid, that forms a pharmaceutically acceptable salt.

The acid addition salts of the compounds described herein may therefore be complexes formed between one or more basic groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

Depending on the stoichiometric proportions between the charged group(s) in the compound and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

As used herein, the term "prodrug" refers to a compound which is converted in the body to an active compound (e.g., the compound of the formula described hereinabove). A prodrug is typically designed to facilitate administration, e.g., by enhancing absorption. A prodrug may comprise, for example, the active compound modified with ester groups, for example, wherein any one or more of the hydroxyl groups of a compound is modified by an acyl group, optionally ($C_{1-4}$)acyl (e.g., acetyl) group to form an ester group, and/or any one or more of the carboxylic acid groups of the compound is modified by an alkoxy or aryloxy group, optionally ($C_{1-4}$)alkoxy (e.g., methyl, ethyl) group to form an ester group.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The compounds described herein can be used as polymorphs and the present embodiments further encompass any isomorph of the compounds and any combination thereof.

The present embodiments further encompass any enantiomers and diastereomers of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers. Each stereo-center (chiral center) gives rise to two different configurations and thus to two different stereoisomers. In the context of the present invention, embodiments of the present invention compounds with multiple chiral centers that occur in any combination of stereoconfiguration, namely any diastereomer.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Materials:

Anti-human IgG-XL665 antibody was obtained from Cisbio Bioassays.

Ficoll Histopaque® 1077 was obtained from Sigma (Israel).

Biotin was obtained from Sigma (Israel).

Biotinylated MIP3a was obtained from Almac Sciences (UK).

Terbium cryptate-conjugated streptavidin (Lumi4®) was obtained from Cisbio Bioassays.

BKT130 was prepared as described in International Application publication WO2010/146584, in which BKT130 is referred to as "BKT-P2-FC". The sequence of BKT130 is also presented therein.

Compound BKT300 was obtained from AnalytiCon Discovery GmbH at 78% purity and at high purity. Using NMR spectroscopy, the high purity sample was determined to have a purity of about 98%, whereas the other sample was confirmed to have about 78% purity.

Chemical syntheses of BKT300-3-c5 and BKT300-11-a5 are described hereinbelow, in Example 6. All reagents were obtained from known vendors.

Migration Assay:

600 µl of RPMI medium was added to the lower chambers of Transwell® transmigration plates, supplemented with 2 µg/ml of MIP3a, 100 ng/ml of SDF-1 or 10 ng/ml of MCP-1. The tested small molecule was added to the lower chambers at the indicated concentration, except in control samples. The MIP3a, SDF-1 or MCP-1 was incubated with the small molecule for 30 minutes at room temperature before the initiation of the migration assay. Following 30 minutes of incubation $2\times10^5$ immune cells were added to the upper chambers of the transmigration plates in a total volume of 100 µl. Cells which migrated within 3 hours to the bottom chamber of the Transwell® plates were counted using a FACScalibur™ flow cytometer.

To evaluate migration toward MIP3a, peripheral blood mononuclear cells (PBMCs) were isolated from heparinized venous blood by centrifugation over Ficoll Histopaque® 1077. CD4+ T cells were further isolated with RosetteSep™ human CD4+ T-cell Enrichment cocktail (StemCell Technologies Inc.), according to the manufacturer's instructions.

To evaluate migration towards SDF-1, Jurkat cells were re-suspended in RPMI medium containing 1% fetal calf serum (FCS).

To evaluate migration towards MCP-1, JTHP-1 cells were re-suspended in RPMI medium containing 1% fetal calf serum (FCS).

Cancer Cells Viability Assays:

The cancer cells were incubated in cell medium with 1% fetal calf serum (FCS) at a concentration of $2\times10^5$ cells/well at a final volume of 250 µl in 96-well plate. The tested small molecule was added to the cells at the indicated concentrations. The cells were incubated for 24 hours and the number of dead and viable cells was then evaluated by fluorescence-activated cell sorting (FACS), using propidium iodide (PI) staining. The IC50 of the small molecule-induced cell death was determined using GraphPad Prism software.

In Vivo Studies:

Protocols of in vivo studies are described in detail in Example 3 hereinbelow.

Example 1

Screening Assay and Activity Assays Identifying Small Molecules which Bind to and Affect Migration of MIP3a A homogeneous time-resolved fluorescence (HTRF) assay was designed as a platform for high-throughput screening (HTS). This assay detected the interaction of BKT130 with MIP3a, using BKT130, biotinylated MIP3a, anti-human IgG-XL665 antibody (which binds to the Fc domain of BKT130) and Lumi4® terbium cryptate-conjugated streptavidin (which binds to the biotin moiety attached to MIP3a).

Biotinylated MIP3a or biotin was diluted in an assay buffer of phosphate buffer saline (PBS) with 0.1% bovine serum albumin (BSA) to a final concentration of 16.7 nM. A detection mix was formed by diluting BKT130, terbium-conjugated streptavidin and anti-human IgG-XL665 antibody in the assay buffer to concentrations of 92.5 nM, 0.01 ng/ml, and 0.9 ng/ml, respectively. 23 µl reactions were incubated in black non-binding 384-well plates (Greiner 784900) at room temperature for 45 minutes, and then read in a PHERAstar FS® high-throughput microplate reader (BMG LABTECH) with a dedicated HTRF laser excitation. HTRF reads are a function of resonant energy transfer from the terbium donor (emitting at a wavelength of 625) to the XL665 acceptor, which becomes excited and emits a fluorescent signal at a wavelength of 665 nm. Only donor/acceptor pairs that are brought into close proximity by binding of MIP3a to BKT130 will result in resonant energy transfer. Binding is expressed as the ratio of the signal at 665 nm to the signal at 625 nm (×10,000).

High-throughput screening (HTS) was performed using an automated workstation with integrated 50 nl pin tool and BioTek™ EL406 dispenser. Compounds from a natural library of about 3,500 natural compounds were maintained in DMSO stock solutions of approximately 10 mM and then transferred to an assay mix containing biotin-MIP3a (or biotin control), and incubated for 15 minutes at room temperature to allow for compound binding. The detection mix was then added, plates were then incubated for a further 45 minutes at room temperature, and then read as described hereinabove.

Compounds with a significant inhibition of binding were selected and picked from the library for repeat assays in serial dilutions to obtain dose response curves.

Analysis of the screen and curve fitting was done using the Genedata Screener® software package.

In the presence of BKT130 and biotinylated-MIP3a without any additional compounds, the signal ratio was 3621 (±409), which corresponded to 0% inhibition of binding (neutral control). In the presence of biotin alone and BKT130, the obtained signal ratio was 763 (±23), corresponding to 100% inhibition of binding (inhibitor control).

Of the 3,500 screened compounds, 32 small molecules inhibited the binding of BKT130 to MIP3a (as expressed by the ratio of the signal at 665 nm to the signal at 625 nm) by more than 40%.

Of these 32 small molecules, 18 small molecules were found to both significantly inhibit the interaction between BKT130 and MIP3a in the high-throughput screening and showed a dose response curve in the serial dilution assay, and were selected for further analysis.

The 18 compounds uncovered by the screening assay were further tested for their ability, at final concentrations of 10 and 50 µg/ml, to inhibit the migration of human CD4+ T-cells toward MIP3a; and to inhibit the migration of immune cells in response to MCP-1 and SDF-1, using the procedures described in the Materials and Methods section hereinabove.

A compound termed BKT300 was identified in these assays as highly potent.

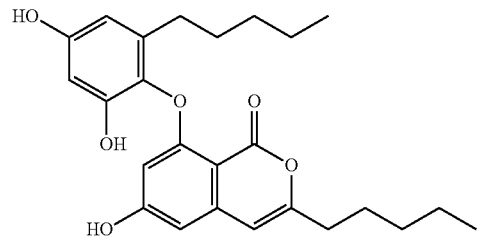

Figure 1:
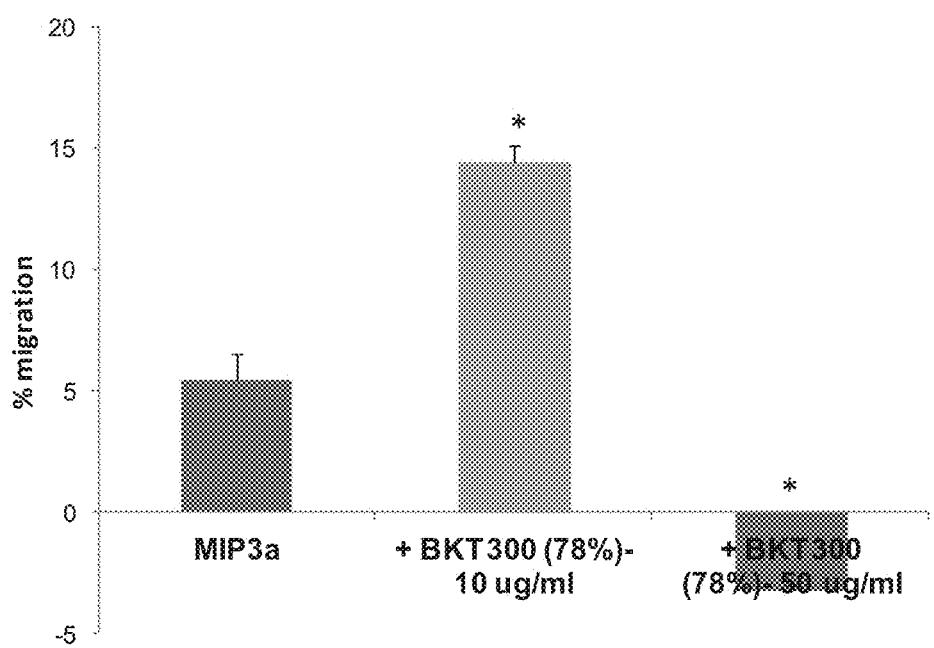

FIG. 1 shows that BKT300 (at 78% purity), at a concentration of 50 µg/ml, completely inhibited CD4+ T-cell migration towards MIP3a, thus indicating that the binding of the compound to MIP3a (as detected in the HTS assay) is associated with inhibition of MIP3a activity.

FIGS. 2A and 2B show that BKT300, at a purity of 78% (FIG. 2A) and of 98% (FIG. 2B) at a concentration of 10 µg/ml, significantly inhibited the migration of lymphocytic Jurkat cells towards SDF-1.

These results indicate that BKT300 is an effective inhibitor of SDF-1 function, and suggest that this compound is effective for treating conditions associated with activity of SDF-1 and CXCR4 (the receptor of SDF-1).

A compound structurally similar to BKT300, termed BKT400, was also found to inhibit the migration of lymphocytic Jurkat cells towards SDF-1, as shown in FIG. 2C.

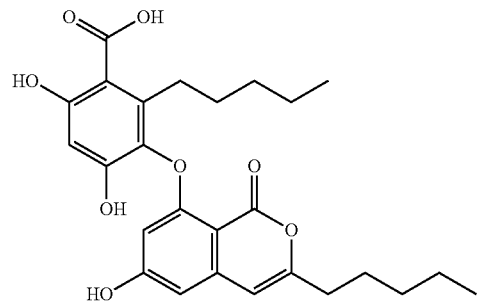

As further shown in FIG. 3, at a concentration of 50 µg/ml, Compound BKT300 (78% purity) exhibited strong inhibition of migration of monocytic THP-1 cells towards MCP-1, but had no apparent effect on migration towards MCP-1 at a concentration of 10 µg/ml.

Taken together, the above results indicate that Compound BKT300 potently inhibit SDF-1 function in a relatively selective manner, with considerably weaker inhibition of MCP-1 and/or MIP3a function (e.g., at a concentration of about 10 µg/ml), and suggest that Compound BKT300 is particularly effective for treating conditions associated with activity of SDF-1 and CXCR4 (the receptor of SDF-1).

Example 2

Effect of BKT300 on Cancer Cells

Additional in vitro and in vivo studies on the effect on cancer cells further confirmed the potential effect of BKT300 on cancer cells.

In order to assess the effect of BKT300 on cancer cells viability, the in vitro effect on MV4-11 human acute myeloid leukemia cells was evaluated. The MV4-11 cancer cells were incubated in RPMI cell medium with 1% fetal calf serum (FCS) at a concentration of $2 \times 10^5$ cells/well at a final volume of 250 μl in 96-well plate. BKT300 was added to the cells at the indicated concentrations. The cells were incubated for 24 hours and the number of dead and viable cells was then evaluated by fluorescence-activated cell sorting (FACS), using propidium iodide (PI) staining. The IC50 of chemokine-induced cell death was determined using GraphPad Prism software.

As shown in FIGS. 4A-4B, BKT300 (at 78% purity) induced cell death of MV4-11 human acute myeloid leukemia cells at concentrations as low as 2 μg/ml (the lowest tested concentration). The $IC_{50}$ for BKT300 (78% purity)-induced death of MV4-11 cells was 2.72 μg/ml.

Induction of cell death by BKT300 was repeated while comparing the effects of a sample of BKT300 at 78% purity with a sample of BKT300 at 98% purity.

As shown in FIGS. 5A-5D, BKT300 at 98% purity was significantly more effective than BKT300 at 78% purity at inducing cell death. For example, BKT300 (at 98% purity) induced a considerably greater degree of cell death at 4.25 μg/ml than did BKT300 at 78% purity.

These results suggest that impurities present in BKT300 (e.g., BKT300 at 78% purity) may reduce the cell death induced by BKT300 per se, and that BKT300 at a high degree of purity (e.g., 98%) is particularly potent in comparison to other compounds described herein.

These results indicate that the chemokine-binding activity of BKT300 is associated with anticancer activity.

The in vitro effect of BKT300 (at 78% purity) on cancer cell viability was further evaluated using a variety of additional cancer cell lines, using procedures as described hereinabove with respect to MV4-11 cells.

As shown in FIGS. 6A and 6B, BKT300 (at 78% purity) induced cell death of RPMI human multiple myeloma cells at concentrations as low as 2 μg/ml (the lowest tested concentration).

As shown in FIGS. 7A and 7B, BKT300 (at 78% purity) induced cell death of Jurkat human acute lymphoblastic leukemia cells at concentrations as low as 2 μg/ml (the lowest tested concentration). The IC50 for BKT300-induced death of Jurkat cells was 3.5 μg/ml.

As shown in FIGS. 8A-9B, BKT300 (at 78% purity) induced cell death of about 30% of Raji (FIGS. 8A and 8B) and Bjab (FIGS. 9A and 9B) human lymphoma cells at a concentration of 8.5 μg/ml, and further induced slight cell death of Raji cells at a concentration of 4.25 μg/ml (FIGS. 8A and 8B).

As shown in FIGS. 10A and 10B, BKT300 (at 78% purity) induced cell death of about 80% of H460 human large cell lung cancer cells at a concentration of 10 μg/ml.

As shown in FIGS. 11A and 11B, BKT300 (at 78% purity) induced cell death of over 90% of H345 human small cell lung cancer cells at a concentration of 8.5 μg/ml.

Example 3

In Vivo Studies

The effect of BKT300 (at 98% purity) on the proliferation of AML cells in vivo was examined by treatment of NOD Scid gamma (NSG) mice transplanted with MV4-11 (FLT3-ITD) cells.

The mice were subjected to irradiation with 300 rad and on the following day were transplanted by IV injection with MV4-11 (FLT3-ITD) cells, $10 \times 10^6$ cells/mouse. 21 days following transplantation, the treated group was injected intraperitoneally with 1 mg/Kg of BKT300 (98% purity) per injection for three consecutive days. On day 25 following transplantation, mice were sacrificed and the survival of the human AML blasts in the blood, spleen and the bone marrow was evaluated using anti human CD45.

Table 1 below presents the study protocol, and some of the results are presented in FIGS. 12A-C.

TABLE 1

| | | Treatments | | | | |
|---|---|---|---|---|---|---|
| Day (−1) | Day 0 | Day 21 | Day 22 | Day 23 | Day 24 | End of Exp. Day 25 |
| Irradiation 300 rad | Cells transplantation $10 \times 10^6$ MV4-11 (IV) 1 mg/Kg/ mouse | + | + | + | + | Mice sacrifice Blood BM spleen |

As shown in FIG. 12B, BKT300 administration dramatically reduced the number and percentage of AML cells in the bone marrow of mice.

FIGS. 12B and 12C present data obtained in a representative FACS analysis showing the presence of human MV4-11 cells with in the bone marrow of untreated mice (FIG. 12C) and of mice treated with BKT300, which further demonstrate the ability of BKT300 to irradicate the leukemic cells.

Example 4

Inhibition of kinase activity by BKT300 In order to further characterize the effect of BKT300 on cell signaling, kinase profiling of BKT300 (at 78% purity) was performed (by the Life Technologies SelectScreen® Biochemical Profiling Lab) using a LanthaScreen® europium kinase binding assay to screen 440 kinases.

The principle of the LanthaScreen® assay is depicted in FIG. 13. Binding of an Alexa Fluor® conjugate or "tracer" to a kinase is detected by addition of a europium (Eu)-labeled anti-tag antibody. Binding of the tracer and antibody to a kinase results in a high degree of FRET, whereas displacement of the tracer with a kinase inhibitor results in a loss of FRET. The kinase tracers are based on ATP-competitive kinase inhibitors, making them suitable for detection of any compounds that bind to the ATP site. Inhibitors that bind the ATP site include both Type I kinase inhibitors, which bind solely to the ATP site, and Type II inhibitors (e.g., imatinib, sorafenib, BIRB-796), which bind to both the ATP site and a second site often referred to as the allosteric site.

Of the 440 screened kinases, BKT300 inhibited 36 kinases by more than 40%. These kinases are presented in Table 2 below.

As shown in Table 2, most of the kinases inhibited by BKT300 were serine/threonine kinases.

Many such kinases are involved in cancer, and some in immune regulation. These results suggest that kinase inhibition by BKT300 can be utilized for treating cancer, particularly by cancer immunotherapy.

TABLE 2

Inhibition of kinases by BKT300

| Kinase | % Inhibition | Kinase Type |
|---|---|---|
| DYRK3 | 47 | ST |
| EPHA8 | 50 | ND |
| GRK4 | 63 | ST |
| GRK5 | 65 | ST |
| MAP4K2 (GCK) | 48 | ND |
| MAP4K4 (HGK) | 40 | ST |
| MELK | 41 | ST |
| PAK7 (KIAA1264) | 40 | ST |
| SGK2 | 43 | ST |
| SRC N1 | 41 | TK |
| ACVRL1 (ALK1) | 47 | ST |
| BMPR1A (ALK3) | 58 | ST |
| CDC7/DBF4 | 53 | ST |
| CDK1/cyclin A2 | 45 | ST |
| CDK11 (Inactive) | 57 | ST |
| CDK8/cyclin C | 64 | ND |
| CLK4 | 73 | ST |
| DAPK2 | 65 | ST |
| DYRK2 | 62 | ST |
| ICK | 41 | ST |
| KIT D820E | 42 | TK* |
| KIT T670E | 51 | TK* |
| MAP4K1 (HPK1) | 45 | ST |
| MAPK10 (JNK3) | 49 | ST |
| MLCK (MLCK2) | 58 | ST |
| MYLK (MLCK) | 63 | ST |
| NUAK2 | 89 | ST |
| STK17A (DRAK1) | 48 | ST |
| STK17B (DRAK2) | 107 | ST |
| STK38 (NDR) | 41 | ST |
| STK38L (NDR2) | 45 | ST |
| TGFBR2 | 43 | ST |
| TTK | 52 | STTK |
| DAPK1 | 43 | ST |
| PIK3CA | 64 | |
| PIK3CD | 77 | |

ST = serine/threonine kinase
TK = tyrosine kinase
STTK = serine/threonine tyrosine kinase
ND = kinase type not determined Example 5

Computational Binding Model of BKT300 to Kinases

All modeling work was performed using the Accelrys software package "Discovery Studio".

Pharmacophore models were constructed manually (not using the automated pharmacophore tools of the package).

All small molecule conformations were generated using the "BEST" conformational search algorithm.

Pharmacophore mapping was performed using the "Pharmacophore mapping" tool of Discovery Studio, with the "flexible" option turned on.

All results of pharmacophore mapping were visually inspected in order to choose best candidate poses.

Design of a Binding Model to Kinases:

As demonstrated in Examples 1-3 hereinabove, BKT300 was identified through a cell-based assay as a promising active agent against leukemia cell lines. As shown in Example 4 hereinabove, in a screen of inhibition against the human Kinome it was shown to inhibit a selection of kinases. Based on this inhibition data, coupled with gene expression data and biological considerations, four kinases were chosen as potential targets that could, possibly in some combination, mediate the anti-leukemia effect of BKT300: MELK, MAP4K4 and two Pi3-kinases (Pik3Cα and Pik3Cδ; also referred to as PIK3CA and PIK3CD), highlighted in Table 2 hereinabove.

Structural analysis of these four kinases was performed using all available structures in the public domain (PDB). For a preliminary construction of pharmacophoric models, the two protein-kinases, MELK and MAP4K4, were selected.

A literature search was performed to identify experimentally-verified "hot spots" (amino acid residues that if mutated result in loss of an order of magnitude or more in activity) for each of the kinases. Two such amino acid residues were identified: Lys40 and Asp150, both positioned within the ATP binding site of the kinases.

The two protein kinases were then aligned so as to achieve the best possible alignment of the ATP binding pocket, and in particular of Lys40 and Asp150. The alignment is shown in FIG. 14.

Inhibitors of these two kinases known in the art were used both to develop a binding model, and to develop a scoring function for ranking potential compounds with respect to their predicted ability to inhibit MELK and MAP4K4.

Two datasets were compiled: (i) a dataset of MELK inhibitors which includes 76 compounds with affinities to the enzyme in the range of from 4.9 to more than 10000 nM; and (ii) a dataset of MAPK4K inhibitors which includes 8 compounds with affinities to the enzyme in the range of from 140 to more than 10000 nM.

Using the crystal structures of available MELK and MAPK4K inhibitors, a binding model that contains a pharmacophore, and overall shape of the ligands were constructed. The pharmacophore was designed such that the bound ligands are required to interact with Lys40 and Asp150.

Validation of the model was performed by mapping the known MELK and MAPK4K inhibitors from the above datasets onto the model. 90% of all of the evaluated MELK inhibitors were successfully mapped to the pharmacophore, whereby the high affinity inhibitors, featuring KD lower than 1000 nM, 100% were successfully mapped onto the model. For the MAPK4K inhibitors, all of the 8 inhibitors were successfully mapped to the model.

These results indicated that the designed binding model is valid and can be used in predicting the binding mode of BKT300.

Predicting the Binding Conformation of BKT300 to Kinases:

BKT300 was mapped to the designed binding model: all low energy conformations of BKT300 were generated, and mapped to the model. All successfully mapped conformers were then docked to the binding site of MELK using the model as a guide, and the docked complex was energetically minimized, allowing the side chains of the protein to adjust to each pose. 165 successful conformations/poses were obtained, and each was visually inspected to evaluate the interaction of the ligand with MELK, to thereby select the most suitable conformation and pose, which is depicted in FIG. 15.

In order to provide additional support for this pose, known crystal structures of MELK inhibitors were screened in order to identify compounds that feature groups that occupy the same positions of the kinase as do the aliphatic groups ("tails") of BKT300, flanking the 3-ring skeleton.

Two such structures were found: N-[3-(4-aminoquinazolin-6-yl)-5-fluorophenyl]-2-(pyrrolidin-1-yl)acetamide (PDB 4OBQ) and 3'-{[(4-bromo-1-methyl-1H-pyrrol-2-yl)carbonyl]amino}-N-[(1S)-1-phenyl-2-(pyrrolidin-1-yl)ethyl]-1',4'-dihydro-5'H-spiro[cyclopropane-1,6'-pyrrolo[3,4-c]pyrazole]-5'-carboxamide (PDB 4BKY). These structures were overlaid on the selected pose of BKT300, as shown in FIG. 16.

It is noted that the chemical nature of the flanking groups ("tails") of these inhibitors differ from the flanking alkyl groups of BKT300, yet occupy the same sub-pockets in the protein kinase. It is further noted that the affinity of BKT300 is relatively low (few tens of µM based on the kinase screening assay summarized in Table 2 hereinabove), whereby the affinities of the overlaid inhibitors is significantly higher (at the nM range).

Example 6

Preparation of BKT300 Analogs

Using the above-described binding model, structural analogs of BKT300 were designed.

The chemical syntheses of exemplary such analogs, denoted herein BKT300-3-c5 and BKT300-11-a5, are as follows.

BKT300-3-c5:

The chemical structure of BKT300-3-c5 can be presented as two tautomers:

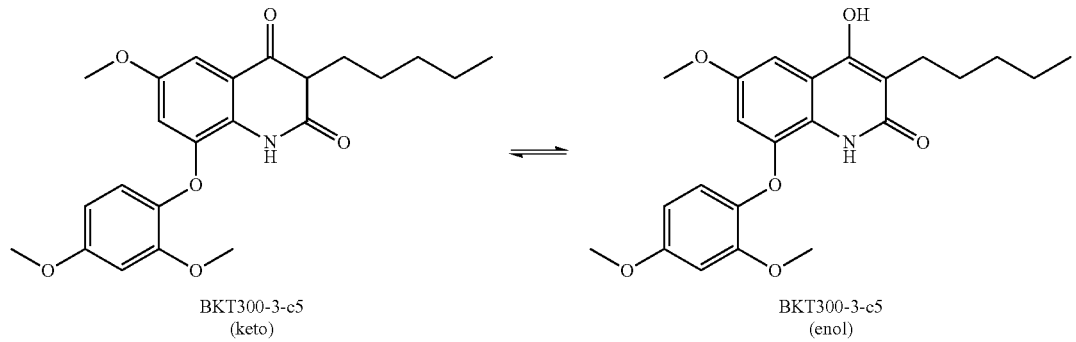 [SMILES: CCCCCC1C(=O)Nc2c(Oc3ccc(OC)cc3OC)cc(OC)cc2C1=O ; CCCCCc1c(O)c2cc(OC)cc(Oc3ccc(OC)cc3OC)c2[nH]c1=O]

BKT300-3-c5 (keto) ⇌ BKT300-3-c5 (enol)

The chemical name of keto tautomer is 8-(2,4-dimethoxyphenoxy)-6-methoxy-3-pentylquinoline-2,4(1H,3H)-dione.

The chemical name of the enol tautomer is 8-(2,4-dimethoxyphenoxy)-4-hydroxy-6-methoxy-3-pentylquinolin-2(1H)-one.

For simplicity, in the following, only the keto tautomer is referred to. However, it is to be noted that the two tautomers can be present, depending on the environmental conditions, either in equilibrium, or as one of the tautomers.

The chemical synthesis of BKT300-3-c5 is depicted in FIG. 17.

Preparation of 2-(2,4-dimethoxyphenoxy)-4-methoxy-1-nitrobenzene (BKT300-3-c1)

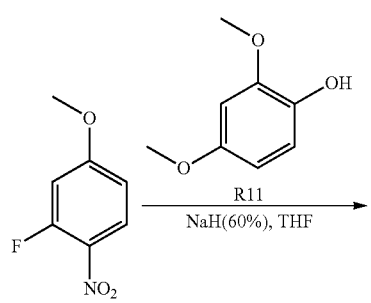

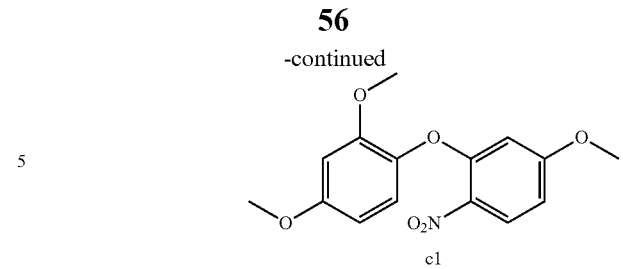

c1

To a solution of 2,4-dimethoxyphenol (R11) (2.0 grams, 13.00 mmol) in THF (50 mL) was added NaH (60%) (450 mg, 26.00 mmol). The reaction mixture was stirred at 0° C. for 30 minutes. Then 2-fluoro-4-methoxy-1-nitrobenzene (2.22 grams, 13.00 mmol) was added at 0° C., and the obtained mixture was stirred at room temperature overnight. Reaction completion was monitored by TLC (EtOAc:Petroleum Ether=1:10). The reaction mixture was poured into ice-water and extracted with EtOAc (2×20 mL). The organic layer was washed with brine (2×50 mL), dried over anhydrous $Na_2SO_4$, and filtered. The filtrate was concentrated in vacuum to give the product 2-(2,4-dimethoxyphenoxy)-4-methoxy-1-nitrobenzene (BKT300-3-c1) (3.04 grams, 76.8% yield) as a yellow oil.

Preparation of 2-(2,4-dimethoxyphenoxy)-4-methoxyaniline (BKT300-3-c2)

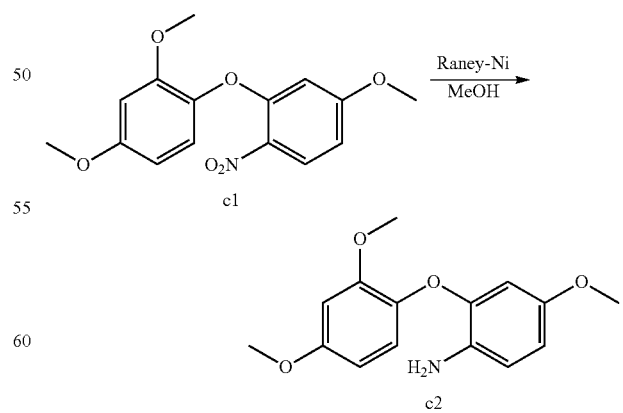

A mixture of 2-(2,4-dimethoxyphenoxy)-4-methoxy-1-nitrobenzene (BKT300-3-c1) (3.04 grams, 10.00 mmol) and Raney-Ni (770 mg) in MeOH (100 mL) was stirred at room temperature for 4 hours. The reaction completion was monitored by LC-MS. The reaction mixture was thereafter filtered, and the filtrate was concentrated in vacuum to give the product 2-(2,4-dimethoxyphenoxy)-4-methoxyaniline (BKT300-3-c2) (2.58 grams, 94.2% yield) as a black oil.

LC-MS: m/z 276.0 (M⁺+H)

Preparation of methyl 2-((2-(2,5-dimethoxyphenoxy)-5-methoxyphenyl)carbamoyl)heptanoate (BKT300-3-c3)

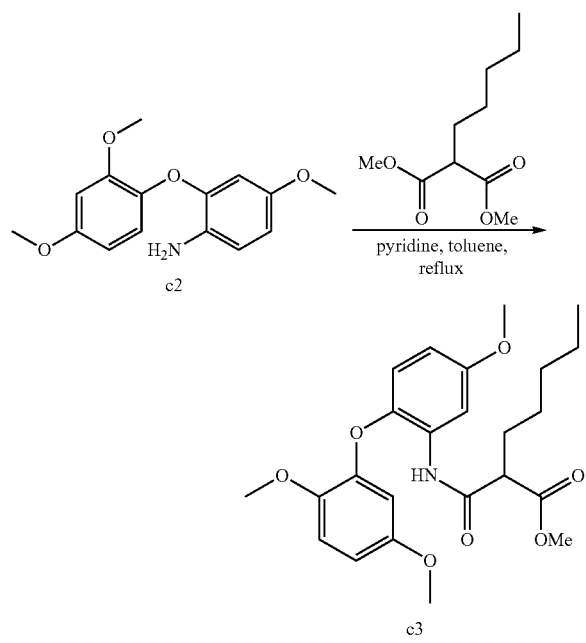

A mixture of 2-(2,4-dimethoxyphenoxy)-4-methoxyaniline (BKT300-3-c2) (3.75 grams, 13.62 mmol), dimethyl 2-pentylmalonate (5.5 grams, 27.2 mmol) and pyridine (2.15 grams, 27.2 mmol) in toluene (40 mL) was stirred at reflux for 40 hours. Reaction completion was monitored by LC-MS. The reaction mixture was thereafter concentrated in vacuum, and the residue was purified by silica gel chromatography eluted with a mixture of EtOAc:Petroleum Ether (1:20~1:10) to give the product methyl 2-((2-(2,5-dimethoxyphenoxy)-5-methoxyphenyl) carbamoyl)heptanoate (BKT300-3-c3) (5.0 grams, 82.45% yield) as a yellow oil.

LC-MS: m/z 446.0 (M⁺+H)

Preparation of 2-((2-(2,4-dimethoxyphenoxy)-5-methoxyphenyl)carbamoyl) heptanoic acid (BKT300-3-c4)

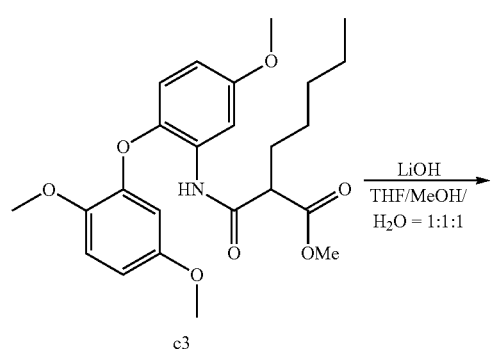

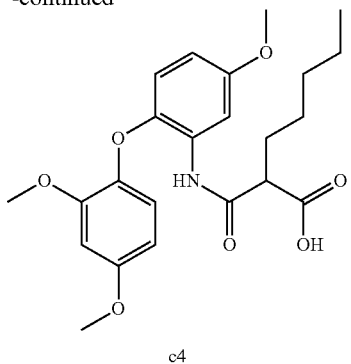

To a solution of methyl 2-((2-(2,5-dimethoxyphenoxy)-5-methoxyphenyl) carbamoyl)heptanoate (BKT300-3-c3) (5.0 grams, 11.23 mmol) in a mixture solution of THF (10 mL), MeOH (10 mL) and H₂O (10 mL) was added LiOH—H₂O (944 mg, 22.46 mmol). The reaction was stirred at room temperature for 16 hours. Reaction completion was monitored by LC-MS. The reaction mixture was thereafter concentrated in vacuum. The residue was dissolved in H₂O (50 mL) and acidified to pH 2-3 using concentrated HCL. The reaction mixture was extracted with EtOAc (2×20 mL), and the organic layer was washed with brine (2×50 mL), dried over anhydrous Na₂SO₄, and filtered. The filtrate was concentrated in vacuum to give the product 2-((2-(2,4-dimethoxyphenoxy)-5-methoxyphenyl)carbamoyl)heptanoic acid (BKT300-3-c4) (4.85 grams, 100% yield) as a yellow solid.

LC-MS: m/z 432.0 (M⁺+H)

Preparation of 8-(2,4-dimethoxyphenoxy)-6-methoxy-3-pentylquinoline-2,4(1H,3H)-dione (BKT300-3-c5)

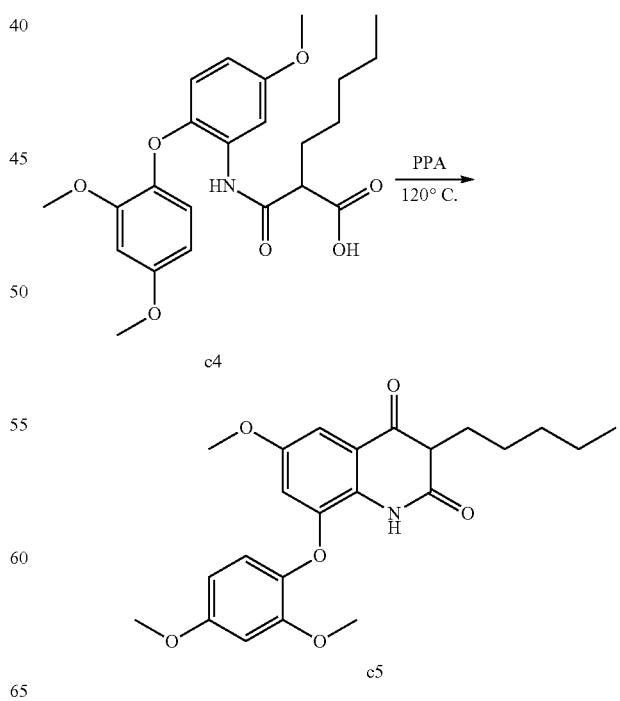

To a PPA solution (8 mL) at 120° C. was added 2-((2-(2, 4-dimethoxyphenoxy)-5-methoxyphenyl)carbamoyl) heptanoic acid (BKT300-3-c4) (2.0 grams, 4.64 mmol) portionwise. The reaction mixture was stirred at 120° C. for 6 hours. The reaction completion was monitored by LC-MS. The reaction mixture was poured into H₂O (100 mL) and extracted with EtOAc (2×20 mL). The organic layer was washed with brine (2×50 mL), dried over anhydrous Na₂SO₄, and filtered. The filtrate was concentrated in vacuum. The residue was purified by silica gel chromatography using a mixture of EtOAc:Petroleum Ether (1:10~1:5) as eluent, to give the product 8-(2,4-dimethoxyphenoxy)-6-methoxy-3-pentylquinoline-2,4(1H,3H)-dione (BKT300-3-c5) (240 mg, 12.5% yield) as a yellow solid.

LC-MS: m/z 414.7 (M⁺+H)

The compound's structure was further verified by ¹H-NMR (using deutorated DMSO as a solvent).

BKT300-11-a5:

The chemical structure of BKT300-11-a5 can be presented as two tautomers:

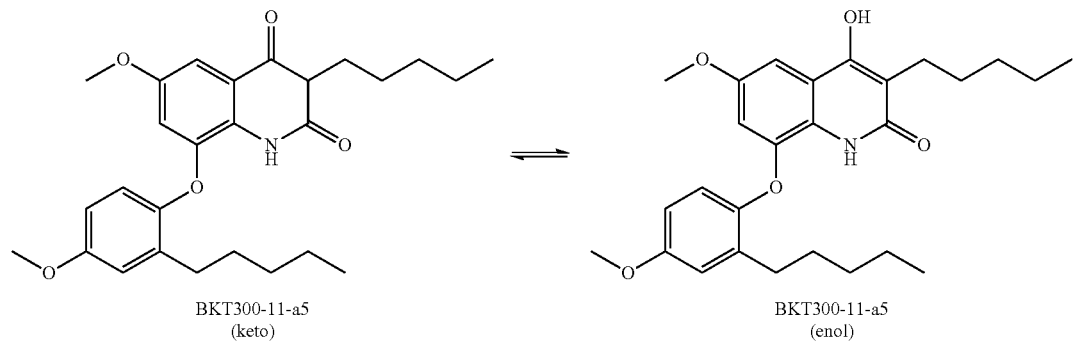 [SMILES: CCCCCc1cc(OC)ccc1Oc1cc(OC)cc2c1NC(=O)C(CCCCC)C2=O ; CCCCCc1cc(OC)ccc1Oc1cc(OC)cc2c(O)c(CCCCC)c(=O)[nH]c12]

BKT300-11-a5 (keto) ⇌ BKT300-11-a5 (enol)

The chemical name of keto tautomer is 6-methoxy-8-(4-methoxy-2-pentylphenoxy)-3-pentylquinoline-2,4(1H,3H)-dione.

The chemical name of the enol tautomer is 4-hydroxy-6-methoxy-8-(4-methoxy-2-pentylphenoxy)-3-pentylquinolin-2(1H)-one.

For simplicity, in the following, only the keto tautomer is referred to. However, it is to be noted that the two tautomers can be present, depending on the environmental conditions, either in equilibrium, or as one of the tautomers.

The chemical synthesis of BKT300-11-a5 is depicted in FIG. 18.

Preparation of 4-methoxy-1-(5-methoxy-2-nitrophenoxy)-2-pentylbenzene (BKT300-11-a1)

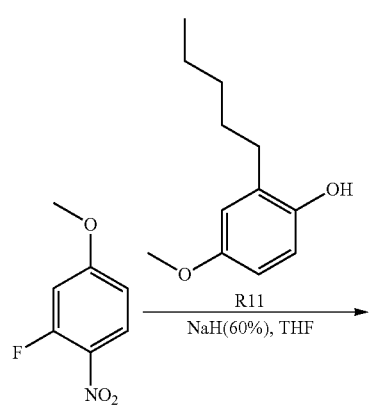

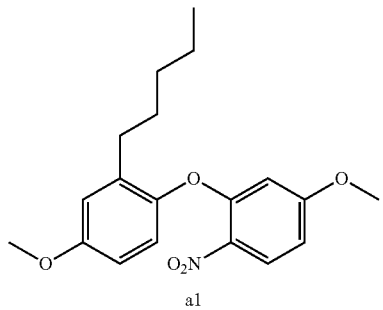

a1

To a solution of 4-methoxy-2-pentylphenol (R11) (2.5 grams, 11.15 mmol) in THF (50 mL) was added NaH (60%) (892 mg, 22.30 mmol). The reaction mixture was stirred at 0° C. for 30 minutes. Then 2-fluoro-4-methoxy-1-nitrobenzene (1.91 grams, 11.15 mmol) was added at 0° C. The reaction mixture was stirred at room temperature overnight. The reaction completion was monitored by TLC (EtOAc: Petroleum Ether 1:10). The reaction mixture thereafter was poured into ice-water and extracted with EtOAc (2×20 mL). The organic layer was washed with brine (2×50 mL), dried over anhydrous Na₂SO₄, and filtered. The filtrate was concentrated in vacuum to give the product 4-methoxy-1-(5-methoxy-2-nitrophenoxy)-2-pentylbenzene (BKT300-11-a1) (3.85 grams, 100% yield) as a yellow oil.

Preparation of 4-methoxy-2-(4-methoxy-2-pentylphenoxy)aniline (BKT300-11-a2)

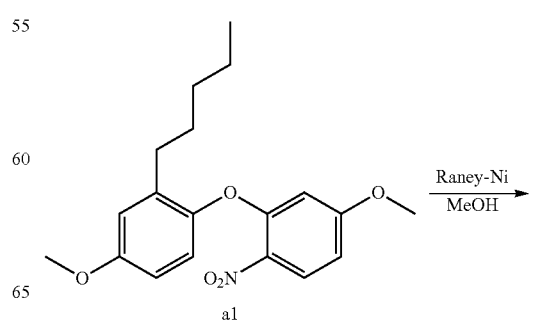

a1

-continued

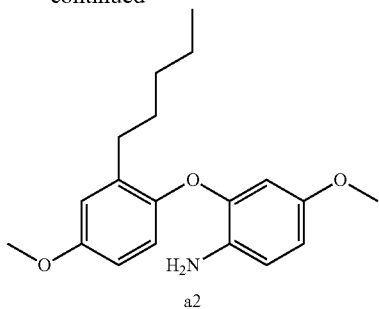

a2

A mixture of 4-methoxy-1-(5-methoxy-2-nitrophenoxy)-2-pentylbenzene (BKT300-11-a1) (3.85 grams, 11.15 mmol, 1.0 eq) and Raney-Ni (770 mg) in MeOH (100 mL) was stirred at room temperature for 4 hours. The reaction completion was monitored by LC-MS. The reaction mixture was thereafter filtered and filtrate was concentrated in vacuum to give the product 4-methoxy-2-(4-methoxy-2-pentyl phenoxy)aniline (BKT300-11-a2) (4.41 grams, 100% yield) as a black oil.

LC-MS: m/z 316.0 (M$^+$+H)

Preparation of methyl 2-((5-methoxy-2-(5-methoxy-2-pentylphenoxy)phenyl)carbamoyl)heptanoate (BKT300-11-a3)

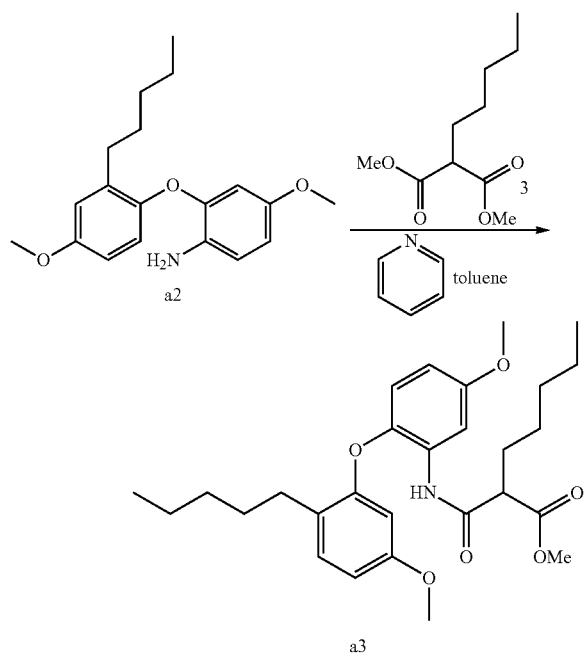

A mixture of 4-methoxy-1-(5-methoxy-2-nitrophenoxy)-2-pentylbenzene (BKT300-11-a1) (4.145 grams, 13.14 mmol), dimethyl 2-pentylmalonate (3.98 grams, 19.71 mmol) and pyridine (2.08 grams, 26.28 mmol) in toluene (80 mL) was stirred at reflux for 40 hours. The reaction completion was monitored by LC-MS. The reaction mixture was concentrated in vacuum, and the residue was purified by silica gel chromatography using a mixture of EtOAc:Petroleum Ether (1:20~1:10) as eluent, to give the product methyl 2-((5-methoxy-2-(5-methoxy-2-pentylphenoxy)phenyl)carbamoyl)heptanoate (BKT300-11-a3) (7.2 grams, 100% yield) as a yellow oil.

LC-MS: m/z 486.0 (M$^+$+H)

Preparation of 2-((5-methoxy-2-(4-methoxy-2-pentylphenoxy)phenyl) carbamoyl)heptanoic acid (BKT300-11-a4)

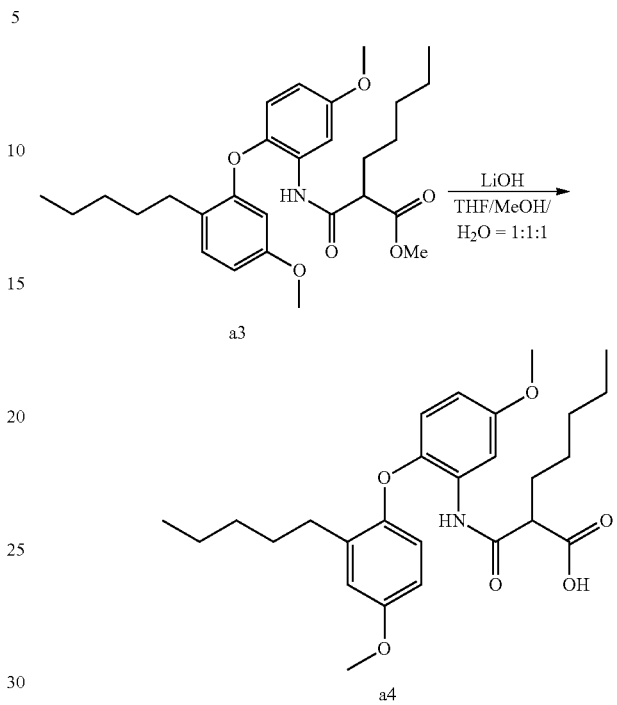

To a solution of methyl 2-((5-methoxy-2-(5-methoxy-2-pentyl phenoxy)phenyl)carbamoyl)heptanoate (BKT300-11-a3) (3.0 grams, 6.19 mmol) in a mixture solution of THF (10 mL), MeOH (10 mL) and H$_2$O (10 mL) was added LiOH—H$_2$O (520 mg, 12.37 mmol). The reaction was stirred at room temperature for 16 hours. The reaction completion was monitored by LC-MS. The reaction mixture was thereafter concentrated in vacuum and the residue was dissolved in H$_2$O (50 mL) and acidified to pH 2-3 using concentrated HCL. The reaction mixture was extracted with EtOAc (2×20 mL). The organic layer was washed with brine (2×50 mL), dried over anhydrous Na$_2$SO$_4$, and filtered. The filtrate was concentrated in vacuum to give the product 2-((5-methoxy-2-(4-methoxy-2-pentylphenoxy)phenyl)carbamoyl)heptanoic acid (BKT300-11-a4) (2.5 grams, 85.6% yield) as a yellow solid.

LC-MS: m/z 472.0 (M$^+$+H)

Preparation of 6-methoxy-8-(4-methoxy-2-pentylphenoxy)-3-pentylquinoline-2,4(1H,3H)-dione (BKT300-11-a5)

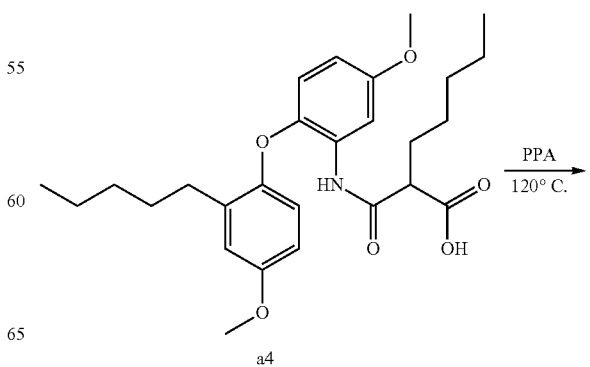

-continued

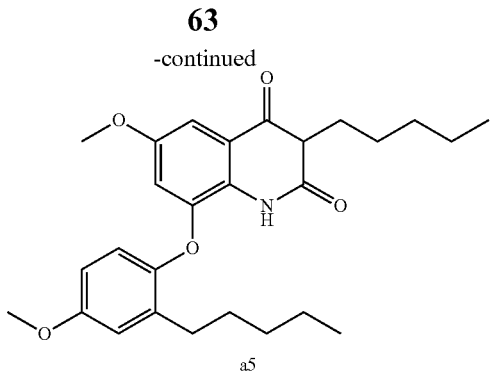

a5

To a PPA solution (8 mL) at 120° C. was added 2-((5-methoxy-2-(4-methoxy-2-pentylphenoxy)phenyl)carbamoyl)heptanoic acid (BKT300-11-a4) (1.0 gRAM, 2.12 mmol) portionwise. The reaction mixture was stirred at 120° C. for 6 hours. The reaction completion was monitored by LC-MS. The reaction mixture was thereafter poured into H$_2$O (100 mL) and extracted with EtOAc (2×20 mL). The organic layer was washed with brine (2×50 mL), dried over anhydrous Na$_2$SO$_4$, and filtered. The filtrate was concentrated in vacuum, and the residue was purified by silica gel chromatography using a mixture of EtOAc:Petroleum Ether (1:10~1:5) as eluent, to give the product 6-methoxy-8-(4-methoxy-2-pentylphenoxy)-3-pentylquinoline-2,4(1H,3H)-dione (BKT300-11-a5) (260 mg, 27.1% yield) as a yellow solid.

LC-MS: m/z 454.7 (M$^+$+H)

$^1$H NMR (400 MHz, DMSO-d$_6$): δ 11.76 (s, 1H), 7.56 (s, 1H), 4.05 (t, J=6.8 Hz, 2H), 1.63-1.56 (m, 2H), 1.36-1.27 (m, 4H), 0.88 (t, J=6.8 Hz, 3H).

Example 7

Activity of BKT300 Analogs

Chemokine-mediated Migration:
The BKT300 analogs were tested in a cell migration assay as described hereinabove, under the "methods" section, so as to determine their effect on a biological activity of the tested chemokines, and hence their activity in treating diseases associated with the chemokine.

FIGS. 19A-B present the effect of BKT300-3-c5 (FIG. 19A) and of BKT300-11-a5 on migration of Jurkat T cells in response to SDF-1, and show modulation of SDF-1 by these compounds, reflected by the inhibition of SDF-1/CXCR4 mediated migration of Jurkat cells.

The effect of BKT300-3-c5 was further tested on migration of Jurkat T cells in response to SDF-1 and of THP-1 in response to MCP-1, was tested and compared to that of IPI-145.

IPI-145 is a small molecule developed by Infinity Pharmaceuticals under the name Duvelisib, and is currently investigated under Phase III clinical trial. IPI-145 is an orally bioavailable inhibitor of the delta and gamma isoforms of phosphoinositide-3 kinase (PI3K), and is said to exhibit potential immunomodulating and antineoplastic activities.

The obtained comparative data is presented in FIG. 20A, for SDF-1, and in FIG. 20B, for MCP-1, and clearly show that BKT300-3-c5 is more effective that IPI-145 in inhibiting both SDF-1/CXCR4 mediated migration of Jurkat cells (TLL) and MCP-1 induced migration of THP-1 (myelomonocytic cells).

Effect on Cancer Cells:
The effect of BKT300-3-c5 on the viability of various cancer cells has been tested, as described under the "method" section hereinabove, and compared to the effect of IPI-145.

FIGS. 21A-B present the effect of BKT300-3-c5 and IPI-145 on the viability of MV4-11 cells (FIG. 21A), and a plot showing the effect of BKT300-3-c5 on the viability of MV4-11 AML cells after 24 hour-treatment, and demonstrating an IC50 value of 0.85 μM for BKT300-3-c5 (FIG. 21B).

FIGS. 22A-B, 23A-B, 24A-B and 25A-B present the effect of BKT300-3-c5 and IPI-145 on various leukemic cells: U937, REH, THP-1 and NB4, respectively.

FIG. 26 presents the effect of BKT300-3-c5 and IPI-145 on prostate cancer PC-3 cells.

FIG. 27 presents the effect of BKT300-3-c5 and IPI-145 on melanoma B16-F10 cells.

It is shown that in all variable tested cell lines, BKT300-3-c5 has a superior effect compared to IPI-145 is reducing the survival of cancer cells.

FIGS. 28A-B present the effect of BKT300-11-a5 on the viability of MV4-11 and show that this BKT300 analog also affect viability of cancer cells.

While further studying the activity of BKT300-3-c5, various cancer cells were incubated with 1 μM BKT300-3-c5, and without it (control), and then stained for 7-ADD.

The obtained data is presented in FIG. 29, and show that in all tested cells, BKT300-3-c5 arrest the growth at the G2M phase of the cell cycle and induce apoptotic cell death. Also shown in FIG. 29 is data obtained for IPI-145 (upper row, right), showing it does not affect growth arrest nor apoptosis.

The effect of BKT300-3-c5 (denoted also as BKT300 (S)) was also demonstrated for additional cell lines from different cancers: Chronic myeloid leukemia (CML), Acute myeloid leukemia (AML), Diffuse large B-cell lymphoma (DLBCL), Myeloma, Ovarian cancer, Neuroblastoma, Lung cancer. The data is presented in Table 3 below.

TABLE 3

| Cell line | Origin | 1.0 Micromolar BKT300 (S) Inhibition of cell growth (%) |
|---|---|---|
| K562 | CML | 71.0 |
| HL60 | AML | 94.9 |
| RPMI8826 | Myeloma | 90.6 |
| SU-DHL-4 | DLBCL | 34 |
| SU-DHL-6 | DLBCL | 50 |
| Farage | DLBCL | 40 |
| Toledo | DLBCL | 4 |
| OVCAR3 | Ovarian | 93.7 |
| SKNBE | Neuroblastoma | 73 |
| H460 | Lung | 78 |

These results further indicate that BKT300 is effective at inducing cell death of a wide variety of cancer cell types.

In further studies, apoptosis induction by BKT300-3-c5 was established by incubating MV4-11 cells with and without BKT300-3-c5 (1 μM) for 24 hours, followed by staining the cells for Annexin-V and Propidium Iodide (PI). The obtained data is presented in FIG. 30, and clearly show reduction in the percentage of viable cells via apoptosis.

In still further studies, the role of caspase-3 (CASP3) in the BKT300-3-c5-induced apoptosis of AML cell lines NB4, U937 and MV4-11 was tested. Cells were incubated with BKT300-3-c5 (1 μM) for 24 hours, and were then tested for the presence of cleaved using mAb against human cleaved caspase 3 by Western blot and Elisa assay to caspase-3.

The CASP3 protein is a member of the cysteine-aspartic acid protease (caspase) family. Sequential activation of caspases plays a central role in the execution-phase of cell apoptosis. Caspases exist as inactive proenzymes that undergo proteolytic processing at conserved aspartic residues to produce two subunits, large and small, that dimerize to form the active enzyme. The active enzyme cleaves and activates caspases 6 and 7, and is processed and activated by caspases 8, 9, and 10.

The obtained data are presented in FIGS. 31A-C, and clearly show that the BKT300-3-c5-induced apoptosis is via caspase-3 activation.

Example 8

Analogs of BKT300-3-c5

Chemical Syntheses:

The following analogs of BKT300-3-c5 were synthesized, similarly to BKT300-3-c5, while modifying the reactants used while preparing c1 and/or c3 (see, FIG. 17) in accordance with the final structure of the analog.

The structures below are presented at their "keto" form, yet, the corresponding "enol" form, and equilibrating forms are also contemplated.

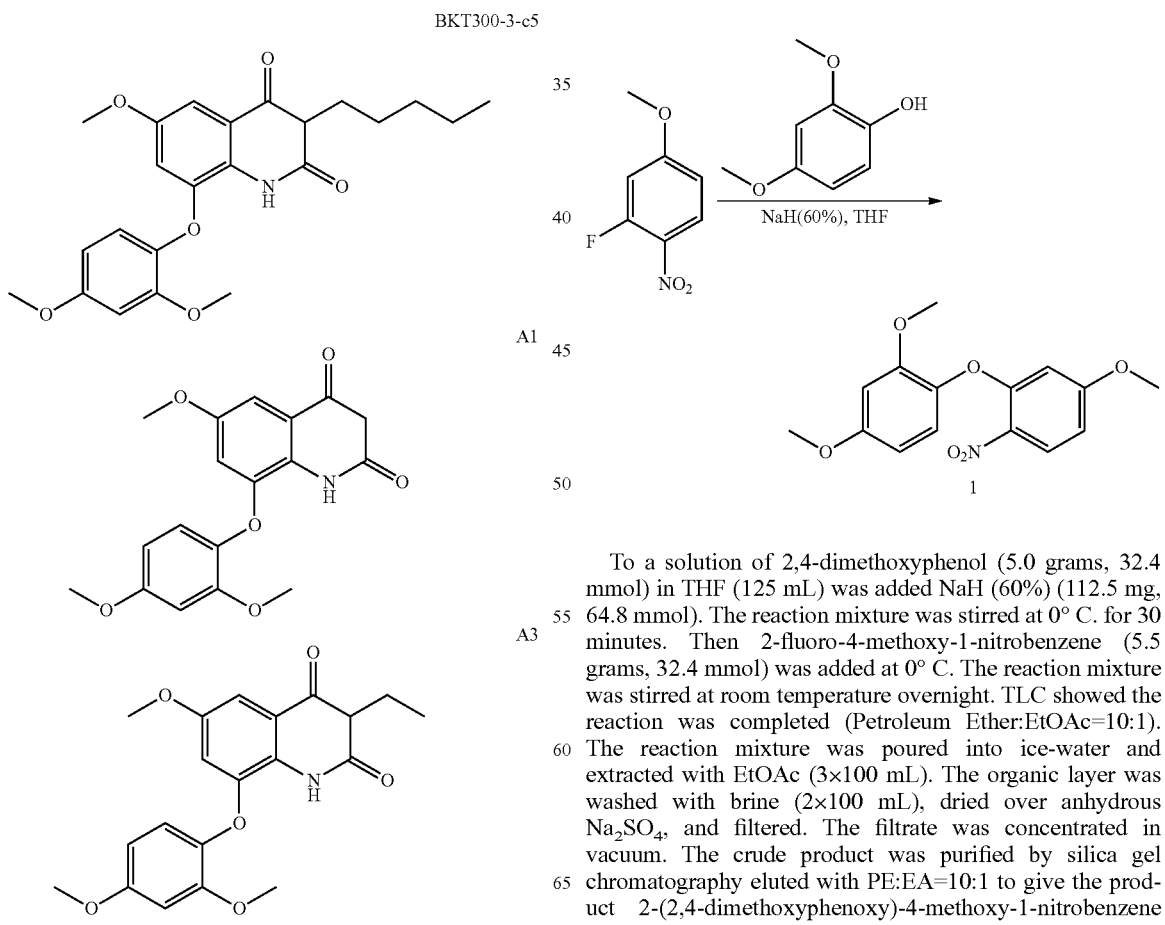

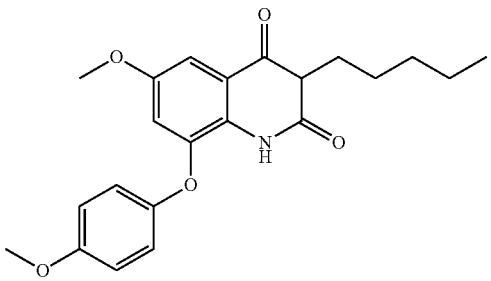

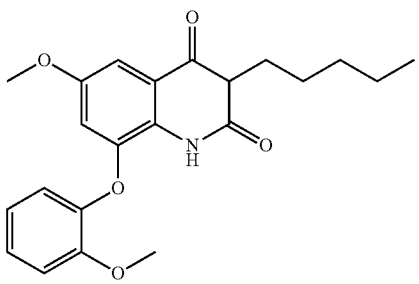

Preparation of Compound A1:

Preparation of 2-(2,4-dimethoxyphenoxy)-4-methoxy-1-nitrobenzene (Compound A1-1)

To a solution of 2,4-dimethoxyphenol (5.0 grams, 32.4 mmol) in THF (125 mL) was added NaH (60%) (112.5 mg, 64.8 mmol). The reaction mixture was stirred at 0° C. for 30 minutes. Then 2-fluoro-4-methoxy-1-nitrobenzene (5.5 grams, 32.4 mmol) was added at 0° C. The reaction mixture was stirred at room temperature overnight. TLC showed the reaction was completed (Petroleum Ether:EtOAc=10:1). The reaction mixture was poured into ice-water and extracted with EtOAc (3×100 mL). The organic layer was washed with brine (2×100 mL), dried over anhydrous Na$_2$SO$_4$, and filtered. The filtrate was concentrated in vacuum. The crude product was purified by silica gel chromatography eluted with PE:EA=10:1 to give the product 2-(2,4-dimethoxyphenoxy)-4-methoxy-1-nitrobenzene (Compound 1) (8.3 grams, 83.8% yield) as a yellow oil.

Preparation of 2-(2,4-dimethoxyphenoxy)-4-methoxyaniline (Compound A1-2)

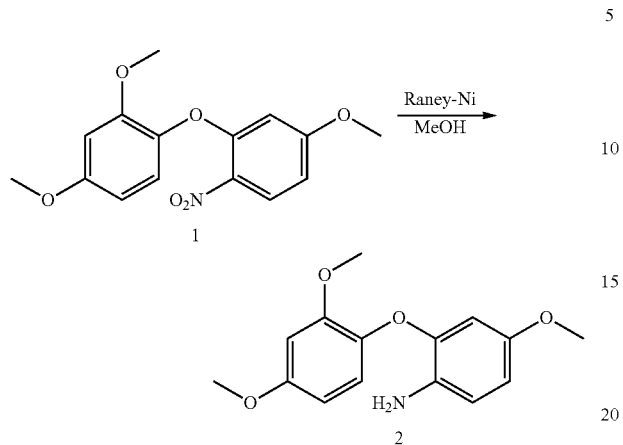

A mixture of 2-(2,4-dimethoxyphenoxy)-4-methoxy-1-nitrobenzene (Compound 1) (8.3 grams, 27.2 mmol) and Raney-Ni (400 mg) in MeOH (300 mL) was stirred at room temperature for overnight. TLC showed the reaction was completed (PE:EA=2:1). The reaction mixture was filtered. The filtrate was concentrated in vacuum to give the product 2-(2,4-dimethoxyphenoxy)-4-methoxyaniline (Compound 2) (8.0 grams, >100% yield) as a black oil, which was used without further purification. LC-MS: m/z 276.0 (M$^+$+H)

Preparation of ethyl 3-((2-(2,5-dimethoxyphenoxy)-4-methoxyphenyl)amino)-3-oxopropanoate (A1-3)

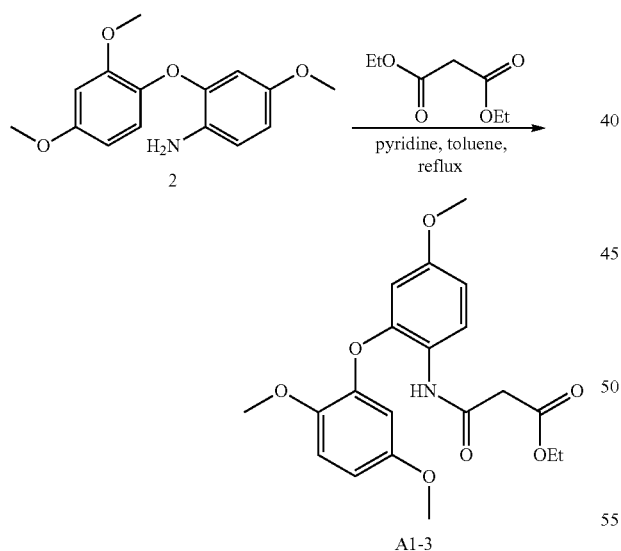

A mixture of 2-(2,4-dimethoxyphenoxy)-4-methoxyaniline (Compound 2) (800 mg, 2.91 mmol), diethyl malonate (960 mg, 5.81 mmol) and pyridine (460 mg, 5.81 mmol) in toluene (20 mL) was stirred at reflux for 24 hours. After the reaction was completed, as monitored by LCMS, the reaction mixture was concentrated in vacuum. The residue was purified by silica gel chromatography eluted with (PE:EA=20:1~10:1) to give the product ethyl 3-((2-(2,5-dimethoxyphenoxy)-4-methoxyphenyl)amino)-3-oxopropanoate (A1-3) (740 mg, 65.3% yield) as a yellow oil. LC-MS: m/z 390 (M$^+$+H)

Preparation of 3-((2-(2,5-dimethoxyphenoxy)-4-methoxyphenyl)amino)-3-oxopropanoic acid (A1-4)

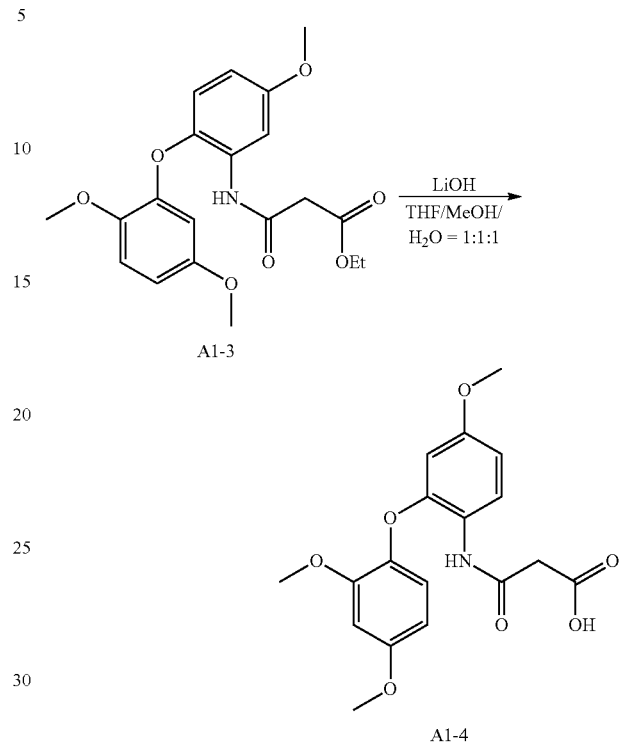

To a solution of ethyl 3-((2-(2,5-dimethoxyphenoxy)-4-methoxyphenyl)amino)-3-oxopropanoate (A1-3) (740 mg, 1.90 mmol) in a mixture solution of THF (15 mL), MeOH (15 mL) and H$_2$O (15 mL) was added LiOH—H$_2$O (798 mg, 19 mmol). The reaction mixture was stirred at room temperature for overnight and was thereafter concentrated in vacuum. The residue was dissolved in H$_2$O (100 mL) and acidified to PH 2-3 using conc. HCl. The reaction mixture was extracted with EtOAc (2×100 mL). The organic layer was washed with brine (2×100 mL), dried over anhydrous Na$_2$SO$_4$, and filtered. The filtrate was concentrated in vacuum to give the product 3-((2-(2,5-dimethoxyphenoxy)-4-methoxyphenyl)amino)-3-oxopropanoic acid (A1-4) (680 mg, 98% yield) as a yellow oil. LC-MS: m/z 362 (M$^+$+H)

Preparation of 8-(2,4-dimethoxyphenoxy)-6-methoxyquinoline-2,4(1H,3H)-dione (A1)

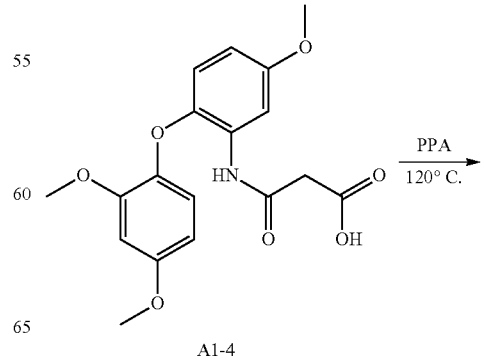

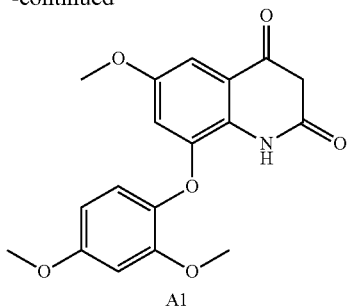

A1

To a PPA solution (30.0 grams) at 120° C. was added 3-((2-(2,5-dimethoxyphenoxy)-4-methoxyphenyl)amino)-3-oxopropanoic acid (A1-4) (680 mg, 1.88 mmol) portionwise. The reaction mixture was stirred at 120° C. for 2 hours. After the reaction was completed, as monitored by LCMS, the reaction mixture was poured into H$_2$O (250 mL) and extracted with EtOAc (3×200 mL). The organic layer was washed with brine (2×100 mL), dried over anhydrous Na$_2$SO$_4$, and filtered. The filtrate was concentrated in vacuum. The residue was purified by silica gel chromatography eluted with (PE:EA=2:1) to give the product 8-(2,4-dimethoxyphenoxy)-6-methoxyquinoline-2,4(1H,3H)-dione (A1) (65 mg, 10% yield) as a yellow solid.

LC-MS: m/z 344.1 (M$^+$+H).

$^1$H NMR (400 MHz, DMSO): δ=11.39 (s, 1H), 10.31 (s, 1H), 7.11 (d, J=8.4 Hz, 1H), 6.89 (d, J=2.4 Hz, 1H), 6.76 (d, J=2.4 Hz, 1H), 6.57 (m, 1H), 6.16 (d, J=2.8 Hz, 1H), 5.81 (s, 1H), 3.79 (s, 3H), 3.76 (s, 3H), 3.73 (s, 3H).

Preparation of Compound A3:

Preparation of 2-(2,4-dimethoxyphenoxy)-4-methoxy-1-nitrobenzene (Compound A3-1)

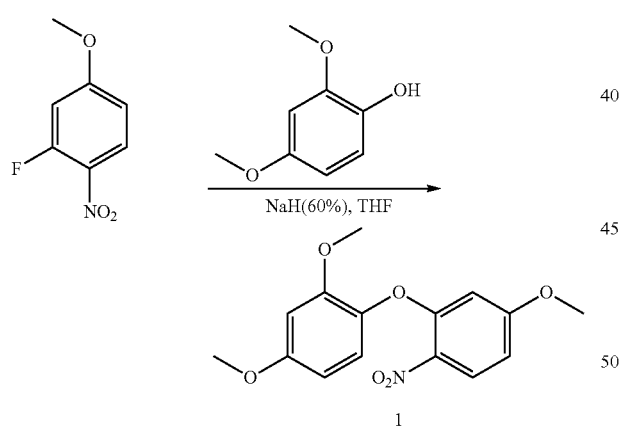

1

To a solution of 2,4-dimethoxyphenol (5.0 grams, 32.4 mmol) in THF (125 mL) was added NaH (60%) (112.5 mg, 64.8 mmol). The reaction mixture was stirred at 0° C. for 30 minutes. Then 2-fluoro-4-methoxy-1-nitrobenzene (5.5 grams, 32.4 mmol) was added at 0° C. The reaction mixture was stirred at room temperature overnight. TLC showed the reaction was completed (Petroleum Ether:EtOAc=10:1). The reaction mixture was poured into ice-water and extracted with EtOAc (3×100 mL). The organic layer was washed with brine (2×100 mL), dried over anhydrous Na$_2$SO$_4$, and filtered. The filtrate was concentrated in vacuum. The crude product was purified by silica gel chromatography eluted with PE:EA=10:1 to give the product 2-(2,4-dimethoxyphenoxy)-4-methoxy-1-nitrobenzene (Compound A3-1) (8.3 grams, 83.8% yield) as a yellow oil.

Preparation of 2-(2,4-dimethoxyphenoxy)-4-methoxyaniline (Compound A3-2)

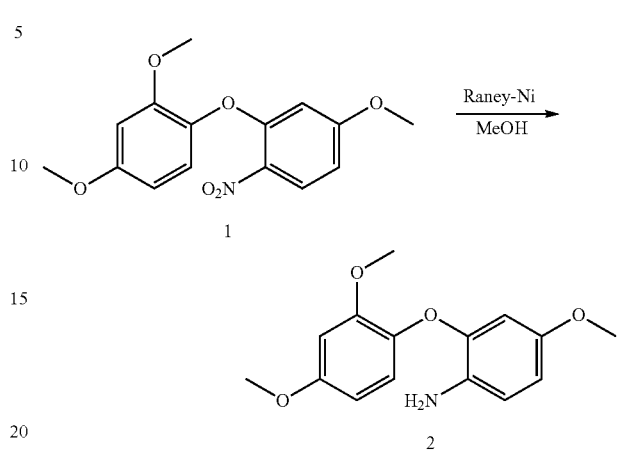

A mixture of 2-(2,4-dimethoxyphenoxy)-4-methoxy-1-nitrobenzene (Compound A3-1) (8.3 grams, 27.2 mmol) and Raney-Ni (400 mg) in MeOH (300 mL) was stirred at room temperature for overnight. TLC showed the reaction was completed (PE:EA=2:1). The reaction mixture was filtered. The filtrate was concentrated in vacuum to give the product 2-(2,4-dimethoxyphenoxy)-4-methoxyaniline (Compound A3-2) (8.0 grams, >100% yield) as a black oil, which was used without further purification. LC-MS: m/z 276.0 (M$^+$+H).

Preparation of ethyl 3-((2-(2,5-dimethoxyphenoxy)-4-methoxyphenyl)amino)-3-oxopropanoate (A3-3)

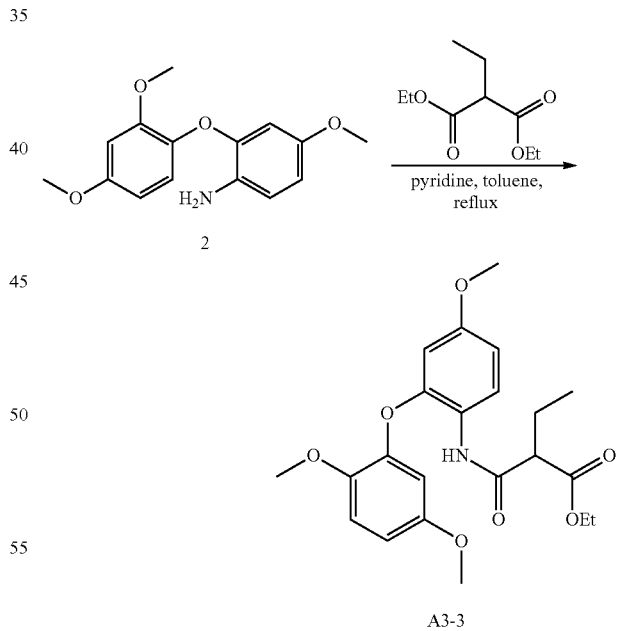

A3-3

A mixture of 2-(2,4-dimethoxyphenoxy)-4-methoxyaniline (Compound A3-2) (800 mg, 2.91 mmol), diethyl 2-ethylmalonate (1.10 gram, 5.81 mmol) and pyridine (460 mg, 5.81 mmol) in toluene (20 mL) was stirred at reflux for 24 hours. After the reaction was completed, as monitored by LCMS, the reaction mixture was concentrated in vacuum. The residue was purified by silica gel chromatography eluted with PE:EA=20:1~10:1 to give the product ethyl 3-((2-(2,5-dimethoxyphenoxy)-4-methoxyphenyl)amino)-

3-oxopropanoate (A3-3) (840 mg, 69.2 v % yield) as a yellow oil. LC-MS: m/z 417 (M⁺+H)

Preparation of 2-((2-(2,4-dimethoxyphenoxy)-4-methoxyphenyl) carbamoyl)butanoic acid (A3-4)

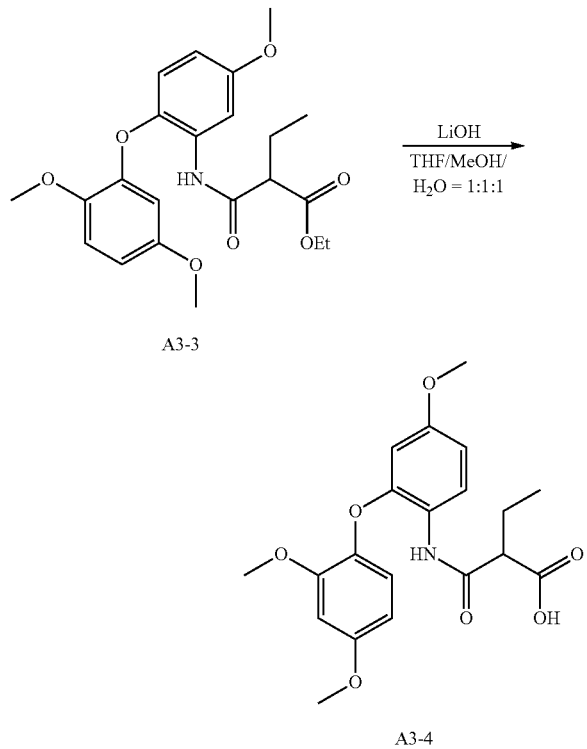

A3-3

A3-4

To a solution of ethyl 3-((2-(2,5-dimethoxyphenoxy)-4-methoxyphenyl)amino)-3-oxopropanoate (A3-3) (840 mg, 2.0 mmol) in a mixture solution of THF (15 mL), MeOH (15 mL) and H₂O (15 mL), was added LiOH—H₂O (798 mg, 19 mmol). The reaction was stirred at room temperature for overnight and was thereafter concentrated in vacuum. The residue was dissolved in H₂O (100 mL) and acidified to pH 2-3 using conc. HCl. The reaction mixture was extracted with EtOAc (2×100 mL). The organic layer was washed with brine (2×100 mL), dried over anhydrous Na₂SO₄, and filtered. The filtrate was concentrated in vacuum to give the product 2-((2-(2,4-dimethoxyphenoxy)-4-methoxyphenyl) carbamoyl)butanoic acid (A3-4) (650 mg, 83% yield) as a yellow oil. LC-MS: m/z 389 (M⁺+H)

Preparation of 8-(2,4-dimethoxyphenoxy)-3-ethyl-6-methoxyquinoline-2,4(1H,3H)-dione (A3)

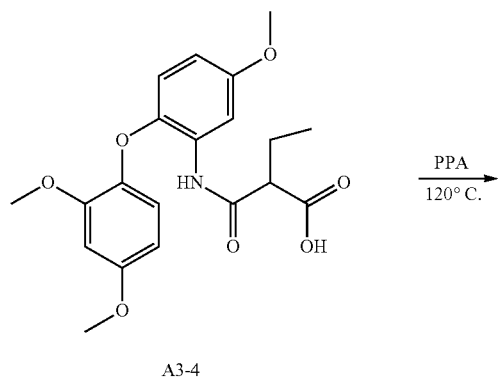

A3-4

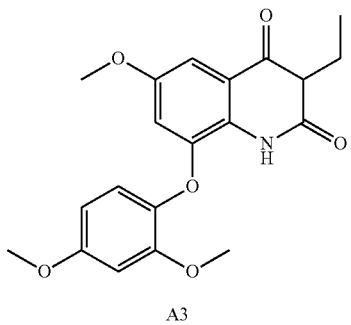

A3

To a PPA solution (30 grams) at 120° C. was added 2-((2-(2,4-dimethoxyphenoxy)-4-methoxyphenyl)carbamoyl)butanoic acid (A3-4) (650 mg, 1.67 mmol) portionwise. The reaction mixture was stirred at 120° C. for 2 hours. After the reaction was completed, as monitored by LCMS, the reaction mixture was poured into H₂O (250 mL) and extracted with EtOAc (3×200 mL). The organic layer was washed with brine (2×100 mL), dried over anhydrous Na₂SO₄, and filtered. The filtrate was concentrated in vacuum. The residue was purified by silica gel chromatography eluted with (PE:EA=2:1) to give the product 8-(2,4-dimethoxyphenoxy)-3-ethyl-6-methoxyquinoline-2,4(1H,3H)-dione (A3) (93 mg, 15% yield) as a yellow solid.

LC-MS: m/z 372.1 (M⁺+H).

¹H NMR (400 MHz, DMSO): δ=10.32 (s, 1H), 10.06 (s, 1H), 7.10 (d, J=4.2 Hz, 1H), 7.03 (d, J=2.4 Hz, 1H), 6.76 (d, J=2.8 Hz, 1H), 6.57 (m, 1H), 6.13 (d, J=2.8 Hz, 1H), 5.81 (s, 1H), 3.79 (s, 3H), 3.73 (s, 3H), 3.69 (s, 3H), 3.26 (m, 2H), 1.03 (m, 3H).

Preparation of Compound B1:

Preparation of Compound B1-1:

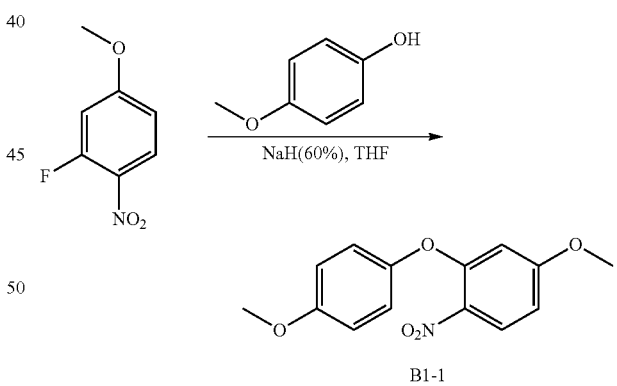

B1-1

To a solution of 4-methoxyphenol (2.3 grams, 18.5 mmol) in THF (30 mL) cooled at 0° C. was added NaH (1.48 grams, 37.09 mmol) slowly. The mixture was stirred at 0° C. for 30 minutes, and then 2-fluoro-4-methoxy-1-nitrobenzene (3.17 grams, 18.5 mmol) was added at 0° C., and thereafter the reaction mixture was allowed to warm to room temperature and maintained for overnight. The reaction mixture was thereafter diluted with water and extracted with EA. The organic layer was washed with brine, dried with NaSO₄, concentrated in vacuum, and purified by flash chromatography, to give compound B1-1 (4-methoxy-2-(4-methoxyphenoxy)-1-nitrobenzene) (4.6 grams, 90.2% yield).

Preparation of Compound B1-2:

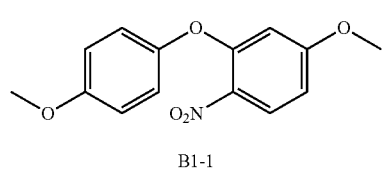

B1-1

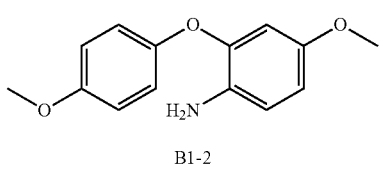

B1-2

Preparation of Compound B1-4:

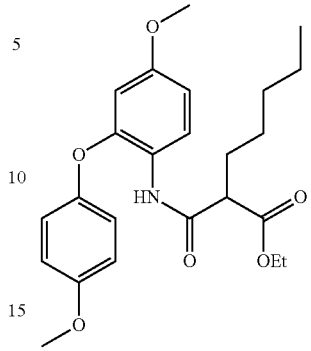

B1-3

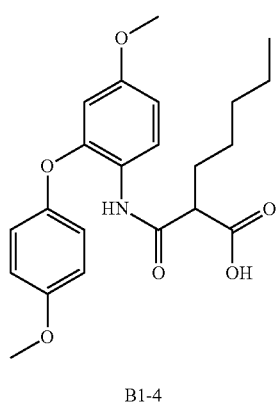

B1-4

To a solution of 4-methoxy-2-(4-methoxyphenoxy)-1-nitrobenzene (4.6 grams, 16.73 mmol) in MeOH was added Pd/C (400 mg) under $H_2$. The reaction mixture was stirred at room temperature for overnight. The mixture was filtered through a glass filter and the filtrate was concentrated in vacuum, purified by flash chromatography to give the product 4-methoxy-2-(4-methoxyphenoxy)aniline (2.3 grams, 56.3% yield).

Preparation of Compound B1-3:

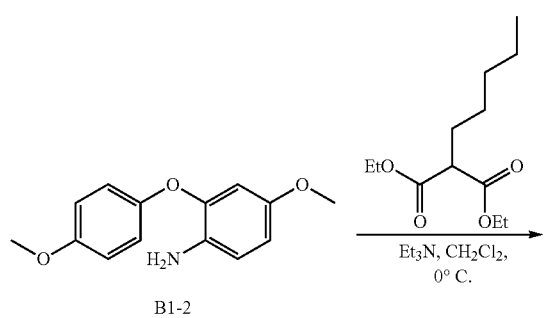

B1-3

A mixture of 4-methoxy-2-(4-methoxyphenoxy)aniline (2.3 grams, 9.39 mmol), dimethyl 2-pentylmalonate (9.48 grams, 46.94 mmol) and pyridine (1.48 grams, 18.78 mmol) in toluene (40 ml) was stirred at reflux for 40 hours. The reaction mixture was thereafter concentrated in vacuum. The residue was purified by flash chromatography to give the product methyl 2-((4-methoxy-2-(4-methoxyphenoxy)phenyl)carbamoyl)heptanoate (2.76 grams, 69.8% yield).

To a solution of methyl 2-((4-methoxy-2-(4-methoxyphenoxy)phenyl) carbamoyl)heptanoate (2.76 grams, 6.43 mmol) in a mixture solution of THF (10 ml), MeOH (10 ml) and $H_2O$ (10 ml), was added LiOH—$H_2O$ (1.08 gram, 25.73 mmol). The reaction mixture was stirred at room temperature for 16 hours and was thereafter concentrated in vacuum. The residue was dissolved in $H_2O$ (50 ml) and acidified to pH 2-3 using conc. HCL. The reaction mixture was extracted with EA (2×20 ml). The organic layer was washed with brine (2×50 ml), dried over anhydrous $Na_2SO_4$, and filtered. The filtrate was concentrated in vacuum to give the product 2-((4-methoxy-2-(4-methoxyphenoxy)phenyl)carbamoyl) heptanoic acid (2.6 grams, 100 percent) which was used without further purification.

Preparation of Compound B1:

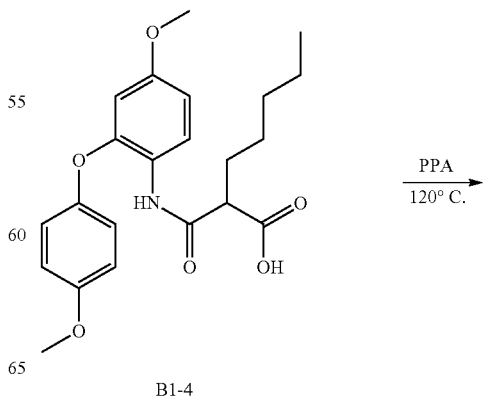

B1-4

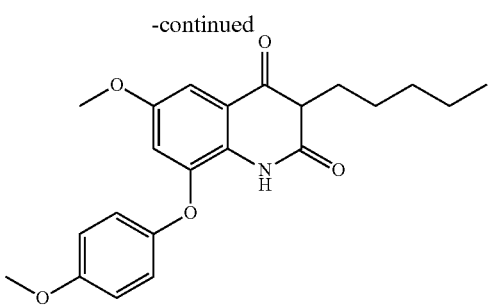

B1

To a PPA solution (8 ml) at 120° C. was added 2-((4-methoxy-2-(4-methoxyphenoxy)phenyl)carbamoyl)heptanoic acid (2.6 grams, 6.48 mmol). The reaction mixture was stirred at 120° C. for 6 hours. The reaction mixture was then poured into $H_2O$ (100 ml) and extracted with EA (2×20 ml). The organic layer was washed with brine (2×50 ml), dried over anhydrous $Na_2SO_4$, and filtered. The filtrate was concentrated in vacuum. The residue was purified by flash chromatography to give the product 6-methoxy-8-(4-methoxyphenoxy)-3-pentylquinoline-2,4(1H,3H)-dione (200 mg, 8.1% yield).

$^1$H NMR (400 MHz, MeOD): δ=7.14 (s, 1H), 7.09-7.06 (d, J=8.8 Hz, 2H), 6.99-6.97 (d, J=8.8 Hz, 2H), 6.41 (s, 1H), 3.81 (s, 3H), 3.77 (s, 3H), 2.68-2.64 (t, J=7.6 Hz, 15.2 Hz, 2H), 1.54 (m, 2H), 1.39 (m, 4H), 0.94-0.90 (m, 3H).

HPLC: purity: at 254 nm=95.76%; at 214 nm=95.07%.
LCMS: m/z [M−1]⁻ 382.2.

Preparation of Compound D1:
Preparation of Compound D1-1:

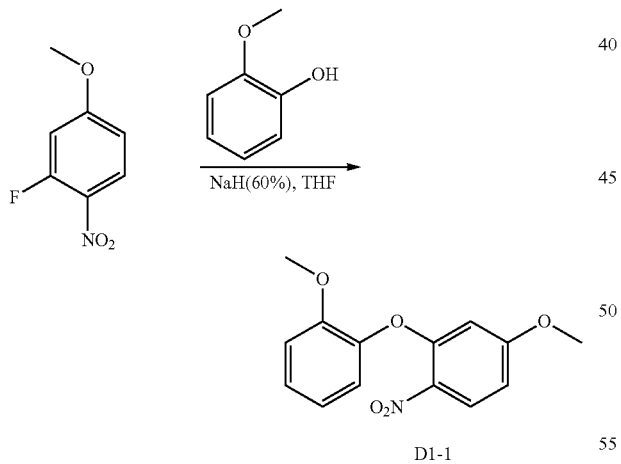

D1-1

To a solution of 2-methoxyphenol (2.3 grams, 18.5 mmol) in THF (30 ml), cooled at 0° C., was added NaH (1.48 grams, 37.09 mmol) slowly. The mixture was stirred at 0° C. for 30 minutes, then 2-fluoro-4-methoxy-1-nitrobenzene (3.17 grams, 18.5 mmol) was added at 0° C., and the reaction mixture was thereafter allowed to warm to room temperature and maintained overnight. The reaction mixture was then diluted with water and extracted with EA. The organic layer was washed with brine, dried with $NaSO_4$, concentrated in vacuum, and purified by flash chromatography, to give compound D1-1 (4-methoxy-2-(2-methoxyphenoxy)-1-nitrobenzene) (4.6 grams, 90.2% yield).

Preparation of Compound D1-2:

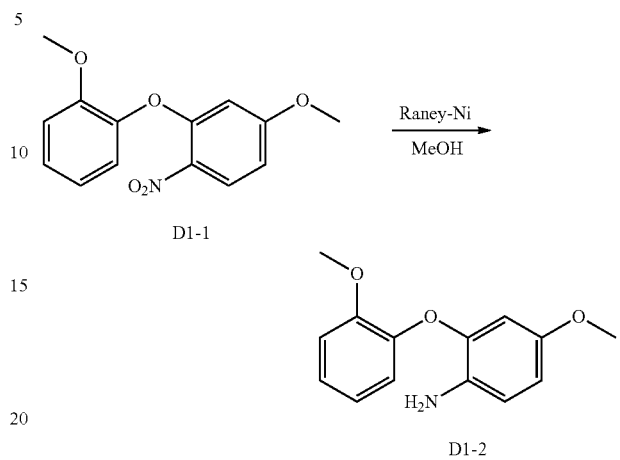

D1-2

To a solution of 4-methoxy-2-(2-methoxyphenoxy)-1-nitrobenzene (2.4 grams, 8.73 mmol) in MeOH was added Pd/C (200 mg) under $H_2$. The reaction mixture was stirred at room temperature for overnight. The mixture was then filtered through a glass filter. The filtrate was concentrated in vacuum, and purified by flash chromatography to give the product 4-methoxy-2-(2-methoxyphenoxy)aniline (1.3 gram, 61.9% yield).

Preparation of Compound D1-3:

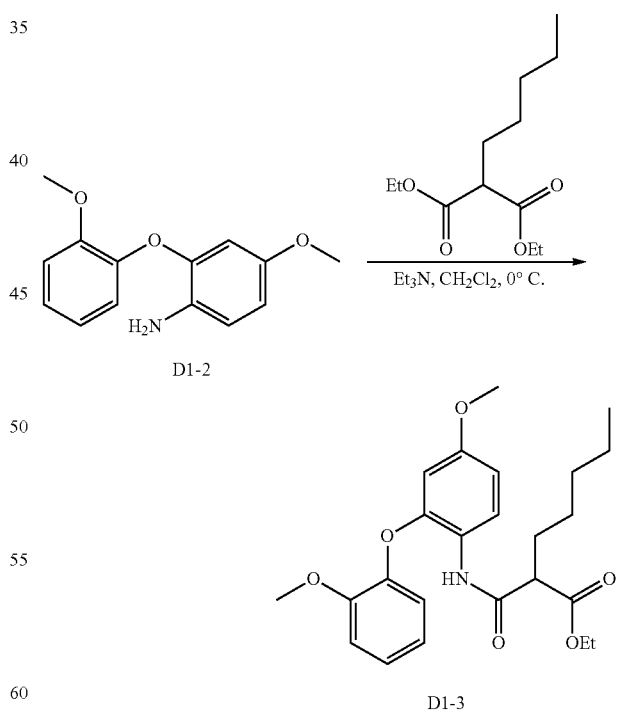

D1-3

A mixture of 4-methoxy-2-(2-methoxyphenoxy)aniline (1.3 gram, 5.31 mmol), dimethyl 2-pentylmalonate (6.1 grams, 26.53 mmol) and pyridine (0.84 gram, 10.61 mmol) in toluene (20 ml) was stirred at reflux for 40 hours. The reaction mixture was concentrated in vacuum. The residue was purified by flash chromatography to give the product methyl 2-((4-methoxy-2-(2-methoxyphenoxy)phenyl)carbamoyl)heptanoate (920 mg, 39.6% yield).

Preparation of Compound D1-4:

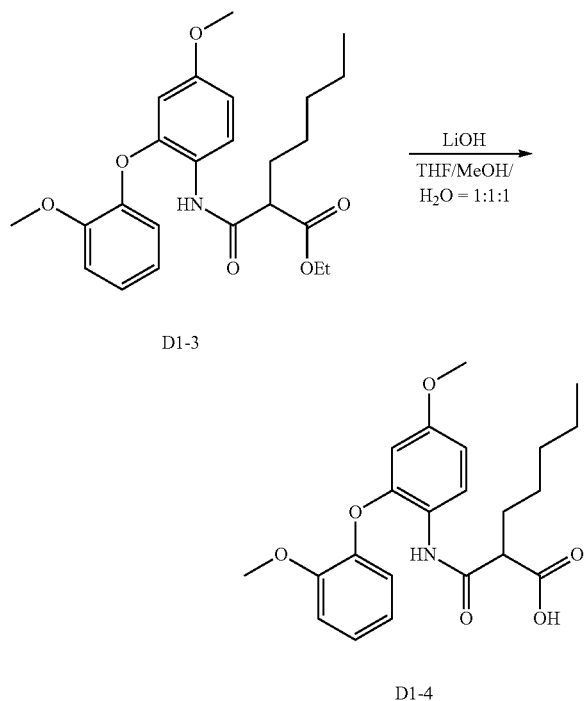

D1-3

D1-4

To a solution of methyl 2-((4-methoxy-2-(2-methoxyphenoxy)phenyl)carbamoyl)heptanoate (920 mg, 2.14 mmol) in a mixture solution of THF (10 ml), MeOH (10 ml) and H$_2$O (10 ml), was added LiOH—H$_2$O (360 grams, 8.58 mmol). The reaction mixture was stirred at room temperature for 16 hours. The reaction mixture was concentrated in vacuum. The residue was dissolved in H$_2$O (50 ml) and acidified to pH 2-3 using conc. HCl. The reaction mixture was extracted with EA (2×20 ml). The organic layer was washed with brine (2×50 ml), dried with Na$_2$SO$_4$, and filtered. The filtrate was concentrated in vacuum to give the product 2-((4-methoxy-2-(2-methoxyphenoxy)phenyl)carbamoyl)heptanoic acid (850 mg, 100% yield) which was used without further purification.

Preparation of Compound D1:

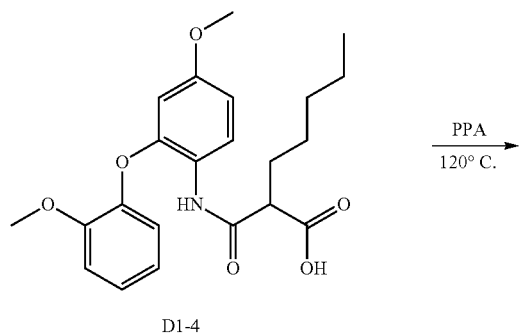

D1-4

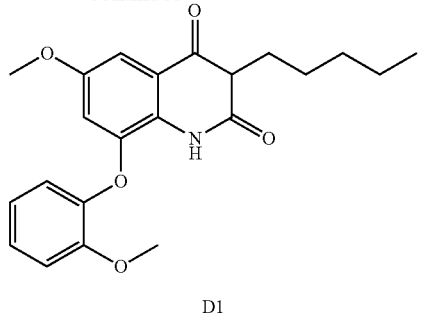

D1

To a PPA solution (5 ml) at 120° C. was added 2-((4-methoxy-2-(2-methoxyphenoxy)phenyl)carbamoyl)heptanoic acid (850 mg, 22.07 mmol). The reaction mixture was stirred at 120° C. for 6 hours. The reaction mixture was then poured into H$_2$O (100 ml) and extracted with EA (2×20 ml). The organic layer was washed with brine (2×50 ml), dried with Na$_2$SO$_4$, and filtered. The filtrate was concentrated in vacuum. The residue was purified by flash chromatography to give the product 6-methoxy-8-(2-methoxyphenoxy)-3-pentylquinoline-2,4(1H,3H)-dione (50 mg, 6.2% yield).

$^1$H NMR (400 MHz, MeOD): δ=7.28 (m, 1H), 7.19-7.16 (m, 2H), 7.12 (s, 1H), 7.05-7.01 (m, 1H), 6.29 (s, 1H), 3.78 (s, 3H), 3.76 (s, 3H), 3.72 (s, 1H), 2.69-2.65 (t, J=7.6 Hz, 15.2 Hz, 2H), 1.55 (m, 2H), 1.39 (m, 4H), 0.94-0.90 (m, 3H).

HPLC: purity: at 254 nm=98.76%, at 214 nm=97.26%.

LCMS: m/z [M−1]$^-$ 382.2.

Activity Assays:

U937 cells were incubated for 24 hours with RPMI medium 1% FCs in the presence of 0.1, 1, and 10 μM of Compounds A1, A3, B1, D1 and BKT300-3-c5, using DMSO as a solvent.

Apoptosis and cell viability were measured using the annexin-V/PI assay.

Cell cycle was measured using the 7-AAD assay.

The data obtained for Compound B1 is presented in FIGS. 32A-C. As shown in FIG. 32A, Compound B1 demonstrates cell cycle arrest at 10 μM, with some effect already observed at a concentration of 1 μM. As shown in FIGS. 32B and 32C, an effect of Compound B1 on cell viability and apoptosis, respectively, was observed at a concentration of 1 μM.

The data obtained for Compound D1 is presented in FIGS. 33A-C. As shown in FIG. 33A, Compound D1 demonstrates cell cycle arrest at 1 μM. As shown in FIGS. 33B and 33C, an effect of Compound D1 on cell viability and apoptosis, respectively, was observed at a concentration of 0.1 μM.

The data obtained for Compound BKT300-3-c5 is presented in FIGS. 34A-C. As shown in FIG. 34A, Compound BKT300-3-c5 demonstrates cell cycle arrest at 0.1 μM. As shown in FIGS. 34B and 34C, an effect of Compound BKT300-3-c5 on cell viability and apoptosis, respectively, was observed at a concentration of 0.1 μM.

The data obtained for Compound A1 is presented in FIGS. 35A-C.

The data obtained for Compound A3 is presented in FIGS. 36A-C.

As shown in FIGS. 35A-C and 36A-C, no effect on both cell cycle and apoptosis was observed for Compounds A1 and A3 in any of the tested concentrations.

No effect was observed when cells were incubated with the solvent (DMSO) only, as shown in FIGS. 37A-C.

These data indicate that the presence of a moderate to long alkyl (as variable A in Formulae Ia and Ib), is essential for the activity of BKT300-3-C5 and structurally related compounds (analogs), possibly due to its role in promoting/facilitating the entrance of the molecule into the cell. Some of the activity is also attributed to the alkoxy groups as variables D, E and G in Formulae Ia and b.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound represented by Formula Ia and/or Ib:

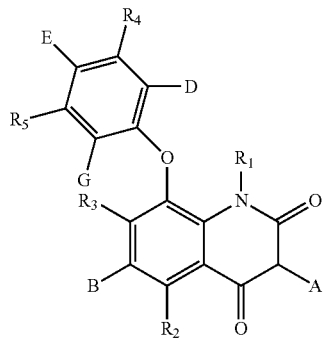

Formula Ia

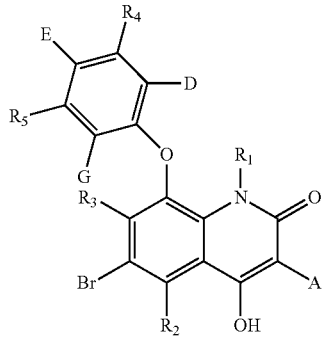

Formula Ib wherein:
A is an alkyl being at least 4 carbon atoms in length;
B is selected from hydroxy and alkoxy;
D, E and G are each independently selected from hydrogen, hydroxy, alkoxy and alkyl, provided that (i) no more than one of D, E and G is said alkyl, (ii) at least one and no more than two of D, E and G are said alkoxy, and (iii) if two of D, E and G are said alkoxy, none of D, E and G is said alkyl;
$R_1$ is selected from hydrogen and alkyl; and
each of $R_2$-$R_5$ is independently selected from hydrogen, hydroxy, halo, alkoxy, thioalkoxy, thiol, thioalkoxy and amine.

2. The compound of claim 1, wherein B is alkoxy.
3. The compound of claim 1, wherein E is alkoxy.
4. The compound of claim 2, wherein E is alkoxy.
5. The compound of claim 1, wherein D is alkoxy.
6. The compound of claim 2, wherein D is alkoxy.
7. The compound of claim 3, wherein D is alkoxy.
8. The compound of claim 4, wherein D is alkoxy.
9. The compound of claim 1, wherein G is alkoxy.
10. The compound of claim 1, wherein G is hydrogen.
11. The compound of claim 1, wherein B is alkoxy, E is alkoxy and G is alkoxy or hydrogen.
12. The compound of claim 11, wherein D is alkoxy.
13. The compound of claim 1, wherein D is said alkyl.
14. The compound of claim 13, wherein G is hydrogen.
15. The compound of claim 13, wherein B is alkoxy.
16. The compound of claim 13, wherein B is alkoxy and E is alkoxy.
17. The compound of claim 1, wherein when one of D, E and G is alkyl, said alkyl is at least 4 carbon atoms in length.
18. The compound of claim 1, being:

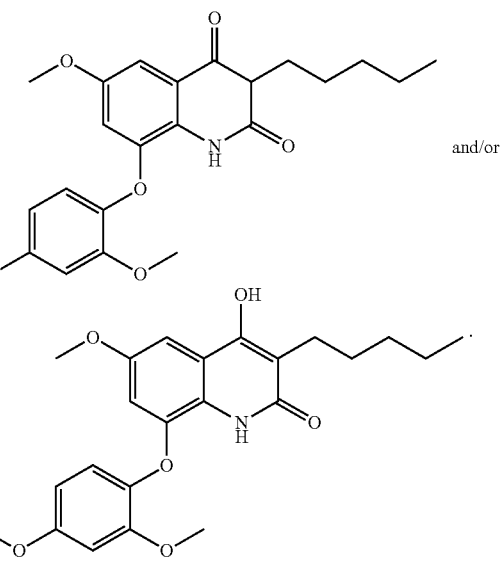

19. The compound of claim 1, being:

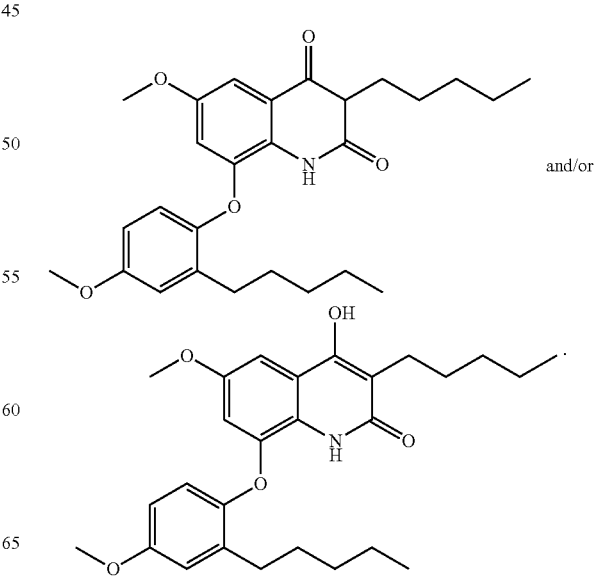

20. The compound of claim 1, being:
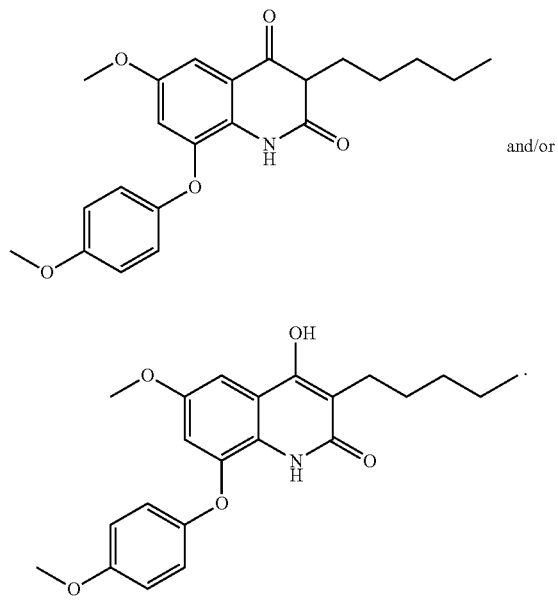
and/or
21. The compound of claim 1, being:
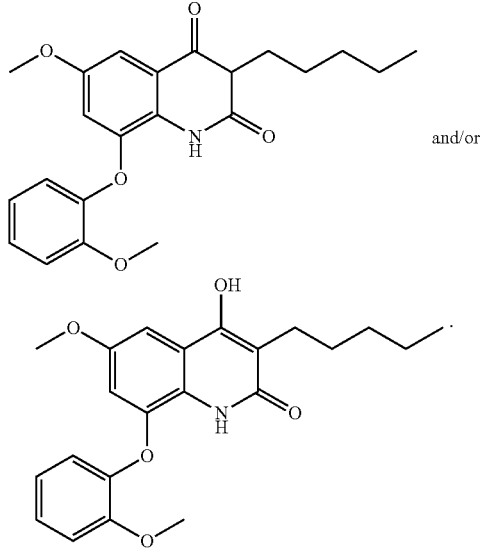
and/or
* * * * *